US010787664B2

(12) United States Patent
Natarajan et al.

(10) Patent No.: US 10,787,664 B2
(45) Date of Patent: Sep. 29, 2020

(54) COMPOUNDS OF CHEMICALLY MODIFIED OLIGONUCLEOTIDES AND METHODS OF USE THEREOF

(71) Applicant: City of Hope, Duarte, CA (US)

(72) Inventors: Rama Natarajan, Duarte, CA (US); Mitsuo Kato, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 15/163,816

(22) Filed: May 25, 2016

(65) Prior Publication Data

US 2016/0348105 A1    Dec. 1, 2016

Related U.S. Application Data

(60) Provisional application No. 62/166,533, filed on May 26, 2015.

(51) Int. Cl.
*C12N 15/113*    (2010.01)

(52) U.S. Cl.
CPC ........ *C12N 15/113* (2013.01); *C12N 2310/10* (2013.01); *C12N 2310/113* (2013.01); *C12N 2310/14* (2013.01); *C12N 2310/20* (2017.05); *C12N 2310/315* (2013.01); *C12N 2310/3231* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,034,506 A | 7/1991 | Summerton et al. | |
| 5,212,162 A | 5/1993 | Missel et al. | |
| 5,235,033 A | 8/1993 | Summerton et al. | |
| 5,403,841 A | 4/1995 | Lang et al. | |
| 6,582,908 B2 * | 6/2003 | Fodor ................... | B01J 19/0046 435/288.3 |
| 2003/0219770 A1 * | 11/2003 | Eshleman ............ | C12Q 1/6869 435/6.14 |
| 2006/0252722 A1 * | 11/2006 | Lollo .................... | C12N 15/111 514/44 A |
| 2007/0123484 A1 * | 5/2007 | Bhat ...................... | C07H 21/02 514/44 A |
| 2011/0178283 A1 * | 7/2011 | Rigoutsos ............... | G06F 19/22 536/24.5 |
| 2016/0251656 A1 * | 9/2016 | Berriel Diaz ........ | C12N 15/113 |

FOREIGN PATENT DOCUMENTS

WO  WO-2005084712 A2 *  9/2005  ........... A61K 31/713
WO  WO 2007/121156    * 10/2007

OTHER PUBLICATIONS

Michlewski et al (Molecular Cell 32, 383-393, Nov. 7, 2008).*
Michlewski et al (Molecular Cell 32, 48 pages, Nov. 7, 2008, Supplemental Data).*
GenBank Accession KC635525 (Jun. 23, 2013) (Year: 2013).*
Simon et al (Structure 19, 172-180, Feb. 9, 2011) (Year: 2011).*
Buck et al. (Biotechniques, 1999, 27:528-536) (Year: 1999).*
Laddha et al (Biology Direct 2013, 8:10) (Year: 2013).*
Chavali et al., Bioinformatics, Oct. 15, 2005, 21(20):3918-25 (Year: 2005).*
Kieleczawa, J Biomol Tech., Jul. 2006, 17(3):207-17 (Year: 2006).*
Kieleczawa (J.Biomol. Tech. 16:220-223, 2005 (Year: 2005).*
Alvarez, M.L. et al. (Oct. 25, 2013). "Role of microRNA 1207-5P and its host gene, the long non-coding RNA Pvt1, as mediators of extracellular matrix accumulation in the kidney: implications for diabetic nephropathy," *PLoS One* 8(10):e77468.
Bartel, D.P. (Jan. 23, 2009). "MicroRNAs: target recognition and regulatory functions," *Cell* 136(2):215-233.
Benetatos, L. et al. (Mar. 2013, e-published Jul. 24, 2012). "The microRNAs within the DLK1-DIO3 genomic region: involvement in disease pathogenesis," *Cell Mol Life Sci* 70(5):795-814.
Berge, S.M. et al. (Jan. 1977). "Pharmaceutical Salts," *Journal of Pharmaceutical Science* 66:1-19.
Chau, B.N. et al. (Feb. 15, 2012). "MicroRNA-21 promotes fibrosis of the kidney by silencing metabolic pathways," *Science Transl Med* 4(121):121ra18.
Croce, C.M. (Oct. 2009). "Causes and consequences of microRNA dysregulation in cancer," *Nat Rev Genet* 10(10):704-714.
Deshpande, S. et al. (Sep. 2013, e-published May 6, 2013). "Transforming growth factor-β-induced cross talk between p53 and a microRNA in the pathogenesis of diabetic nephropathy," *Diabetes* 62(9):3151-62.
Eyles, J.E. et al. (Jul. 1997). "Oral delivery and fate of poly(lactic acid) microsphere-encapsulated interferon in rats," *J. Pharm. Pharmacol.* 49(7):669-674.
Fabian, M.R. et al. (2010). "Regulation of mRNA translation and stability by microRNAs," *Annual Review of Biochemistry* 79:351-379.
Fiore, R. et al. (Mar. 18, 2009, e-published Feb. 5, 2009). "Mef2-mediated transcription of the miR379-410 cluster regulates activity-dependent dendritogenesis by fine-tuning Pumilio2 protein levels," *EMBO J* 28(6):697-710.
Gao, Z.H. et al. (Jun. 1995). "Controlled release of a contraceptive steroid from biodegradable and injectable gel formulations: in vitro evaluation," *Pharm. Res* 12(6):857-863.
Glazov, E.A. et al. (May 2008, e-published Feb. 14, 2008). "Origin, evolution, and biological role of miRNA cluster in DLK-DIO3 genomic region in placental mammals," *Mol Biol Evol* 25(5):939-948.
He, F. et al. (Aug. 2014, e-published Jun. 9, 2014). "MiR-135a promotes renal fibrosis in diabetic nephropathy by regulating TRPC1," *Diabetologia* 57(8):1726-1736.

(Continued)

Primary Examiner — Richard A Schnizer
(74) *Attorney, Agent, or Firm* — Mintz, Levin, Cohn, Ferris, Glovsky and Popeo, P.C.

(57) ABSTRACT

The present disclosure relates to isolated compounds including a nucleic acid sequence capable of hybridizing to an RNA sequence 10 to 270 nucleobases downstream of the transcription start site of a mammalian microRNA-379 transcript; method of treating diabetic nephropathy in a subject with the compounds; and method of inhibiting expression of a mammalian microRNA-379 megacluster with the compounds.

9 Claims, 47 Drawing Sheets
Specification includes a Sequence Listing.

(56) References Cited

OTHER PUBLICATIONS

Hirao, K. et al. (Apr. 7, 2006, e-published Jan. 23, 2006). "EDEM3, a soluble EDEM homolog, enhances glycoprotein endoplasmic reticulum-associated degradation and mannose trimming," *J Biol Chem* 281(14):9650-9658.

Jin, W. et al. (May 4, 2012, e-published Mar. 19, 2012). "Small Rna sequencing reveals microRNAs that modulate angiotensin II effects in vascular smooth muscle cells," *J Biol Chem* 287(19):15672-15683.

Kanwar Y.S. et al. (2011). "A glimpse of various pathogenetic mechanisms of diabetic nephropathy," *Annual Review of Pathology* 6:395-423.

Kato, M. et al. (Feb. 27, 2007, e-published Feb. 20, 2007). "MicroRNA-192 in diabetic kidney glomeruli and its function in TGF-beta-induced collagen expression via inhibition of E-box repressors," *PNAS USA* 104(9):3432-3437.

Kato, M. et al. (Jul. 2009, e-published Jun. 21, 2009). "TGF-beta activates Akt kinase through a microRNA-dependent amplifying circuit targeting PTEN," *Nat Cell Biol* 11(7):881-889.

Kato, M. et al. (Aug. 2011). "A microRNA circuit mediates transforming growth factor-β1 autoregulation in renal glomerular mesangial cells," *Kidney Int* 80(4):358-368.

Kato, M. et al. (Jun. 4, 2013). "TGF-β induces acetylation of chromatin and of Ets-1 to alleviate repression of miR-192 in diabetic nephropathy," *Sci Signal* 6(278):ra43.

Kato, M. et al. (Sep. 2014, e-published Jul. 8, 2014). "Diabetic nephropathy—emerging epigenetic mechanisms," *Nat Rev Nephrol* 10(9):517-530.

Kato, M. et al. (Sep. 2015 e-published Apr. 15, 2015). "MicroRNAs in diabetic nephropathy: functions, biomarkers, and therapeutic targets," *Ann NY Acad Sci* 1353:72-88.

Kriegel, a.J. et al. (Dec. 2010, e-published Aug. 16, 2010). "MicroRNA-target pairs in human renal epithelial cells treated with transforming growth factor beta 1: a novel role of miR-382," *Nucleic Acids Res* 38(22):8338-8347.

Krüztfeldt, J. et al. (Dec. 1, 2005, e-published Oct. 30, 2005). "Silencing of microRNAs in vivo with antagomirs," *Nature* 438(7068):685-689.

Lan, F. et al. (Aug. 9, 2007). "Recognition of unmethylated histone H3 lysine 4 links BHC80 to LSD1-mediated gene repression," *Nature* 448(7154):718-722.

Lee, J.E. et al. (Mar. 13, 2012, e-published Feb. 27, 2012). "RNase H-mediated degradation of toxic RNA in myotonic dystrophy type 1," *PNAS USA* 109(11):4221-4226.

Liang, X.H. et al. (Jul. 2014, e-published May 26, 2014). "TCP1 complex proteins interact with phosphorothioate oligonucleotides and can co-localize in oligonucleotide-induced nuclear bodies in mammalian cells," *Nucleic Acids Res* 42(12):7819-7832.

Lindenmeyer, M.T. et al. (Nov. 2008, e-published Sep. 5, 2008). "Proteinuria and hyperglycemia induce endoplasmic reticulum stress," *J Am Soc Nephrol* 19(11):2225-2236.

Lindow, M. et al. (Oct. 29, 2012). "Discovering the first microRNA-targeted drug," *J Cell Biol* 199(3):407-412.

Long, J. et al. (Apr. 1, 2011, e-published Feb. 10, 2011). "MicroRNA-29c is a signature microRNA under high glucose conditions that targets Sprouty homolog 1, and its in vivo knockdown prevents progression of diabetic nephropathy," *J Biol Chem* 286(13):11837-11848.

López De Silanes, I. et al. (Mar. 2, 2004, e-published Feb. 23, 2004). "Identification of a target RNA motif for RNA-binding protein HuR," *PNAS USA* 101(9):2987-2992.

Massagué, J. (Jun. 28, 1996). "TGFbeta signaling: receptors, transducers, and Mad proteins," *Cell* 85(7):947-50.

Michalik, K.M. et al. (Apr. 25, 2014, e-published Mar. 6, 2014). "Long noncoding RNA MALAT1 regulates endothelial cell function and vessel growth," *Circulation Research* 114(9):1389-1397.

Mukhopadhyay, D. et al. (Jan. 2003). "Coupled mRNA stabilization and translational silencing of cyclooxygenase-2 by a novel RNA binding protein, CUGBP2," *Mol Cell* 11(1):113-126.

Novoa, I. et al. (May 2010, e-published Apr. 4, 2010). "Mitotic cell-cycle progression is regulated by CPEB1 and CPEB4-dependent translational control," *Nat Cell Biol* 12(5):447-456.

Park, J.T. et al. (Aug. 2, 2013, e-published Jun. 20, 2013). "FOG2 protein down-regulation by transforming growth factor-β1-induced microRNA-200b/c leads to Akt kinase activation and glomerular mesangial hypertrophy related to diabetic nephropathy," *J Biol Chem* 288(31):22469-22480.

Putta, S. et al. (Mar. 2012, e-published Jan. 5, 2012). "Inhibiting microRNA-192 ameliorates renal fibrosis in diabetic nephropathy," *J Am Soc Nephrol* 23(3):458-69.

Rao. K.P. (1995). "Recent developments of collagen-based materials for medical applications and drug delivery systems," *J. Biomater Sci. Polym. Ed.* 7(7):623-645.

Reidy, K. et al. (Jun. 2014, e-published Jun. 2, 2014). "Molecular mechanisms of diabetic kidney disease," *The Journal of Clinical Investigation* 124(6):2333-2340.

Roberts, A.B. et al. (Mar. 1992). "TGF-beta: regulation of extracellular matrix," *Kidney Int* 41(3):557-559.

Salmena, L. et al. (May 2, 2008). "Tenets of PTEN tumor suppression," *Cell* 133(3):403-414.

Sharma, K. et al. (Oct. 1995). "Hyperglycemia and diabetic kidney disease. The case for transforming growth factor-beta as a key mediator," *Diabetes* 44(10):1139-46.

Smale, S.T. et al. (Apr. 7, 1989). "The "initiator" as a transcription control element," *Cell* 57(1):103-113.

Subramanian, A. et al. (Oct. 25, 2005, e-published Sep. 30, 2005). "Gene set enrichment analysis: a knowledge-based approach for interpreting genome-wide expression profiles," *PNAS USA* 102(43):15545-15550.

Trionfini, P. et al. (Jan. 2015, Nov. 11, 2014). "MicroRNAs in kidney physiology and disease," *Nat Rev Nephrol* 11(1):23-33.

Tritschler, F. et al. (May 2010, e-published Apr. 9, 2010). "Role of GW182 proteins and PABPC1 in the miRNA pathway: a sense of déjà vu," *Nature Reviews* 11(5):379-384.

Van Rooij, E. et al. (Jul. 2014). "Development of microRNA therapeutics is coming of age," *EMBO Mol Med* 6(7):851-864.

Wang, Q. et al. (Dec. 2008, e-published Aug. 20, 2008). "MicroRNA-377 is up-regulated and can lead to increased fibronectin production in diabetic nephropathy," *FASEB J* 22(12):4126-4135.

Wu, J. et al. (May 2010, e-published Apr. 2, 2010). "Induction of diabetes in aged C57B6 mice results in severe nephropathy: an association with oxidative stress, endoplasmic reticulum stress, and inflammation," *The American Journal of Pathology* 176(5):2163-2176.

Yamamoto,T. et al. (Mar. 1, 1993). "Expression of transforming growth factor beta is elevated in human and experimental diabetic nephropathy," *PNAS USA* 90(5):1814-1818.

Zhang, Y. et al. (Sep. 12, 1996). "Receptor-associated Mad homologues synergize as effectors of the TGF-beta response," *Nature* 383(6596):168-172.

Zhong, X. et al. (Mar. 2013, e-published). "miR-21 is a key therapeutic target for renal injury in a mouse model of type 2 diabetes," *Diabetologia* 56(3):663-674.

Ziyadeh, F.N. et al. (Jul. 5, 2000). "Long-term prevention of renal insufficiency, excess matrix gene expression, and glomerular mesangial matrix expansion by treatment with monoclonal antitransforming growth factor-beta antibody in db/db diabetic mice," *PNAS USA* 97(14):8015-8020.

* cited by examiner

GGTTCCTGAAGAGATGGTAGACTATGGAACGTAGGCGTTATGTGTTTTTGACCTATGTAACATGGTCCACTAACTGTCAGTATCCAATCCATCCTCG

S1 →  S2 →  S3 →
← AS1  ← AS2

Mature miR-379
*Precursor miR-379*

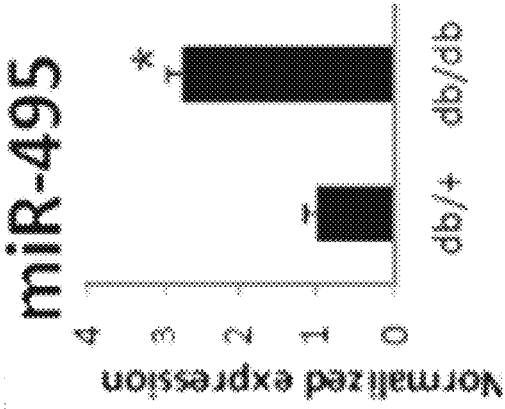
FIG. 12A  FIG. 12B
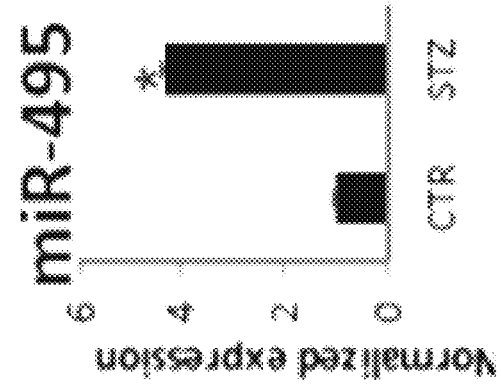
FIG. 12C  FIG. 12D
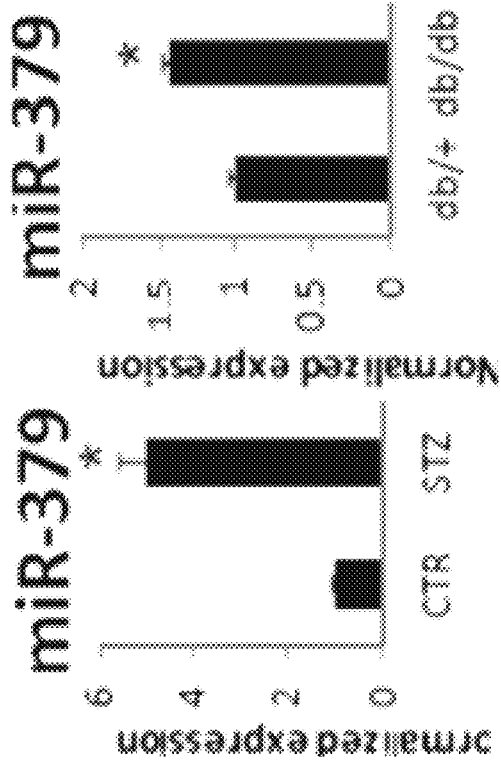
FIG. 12E  FIG. 12F
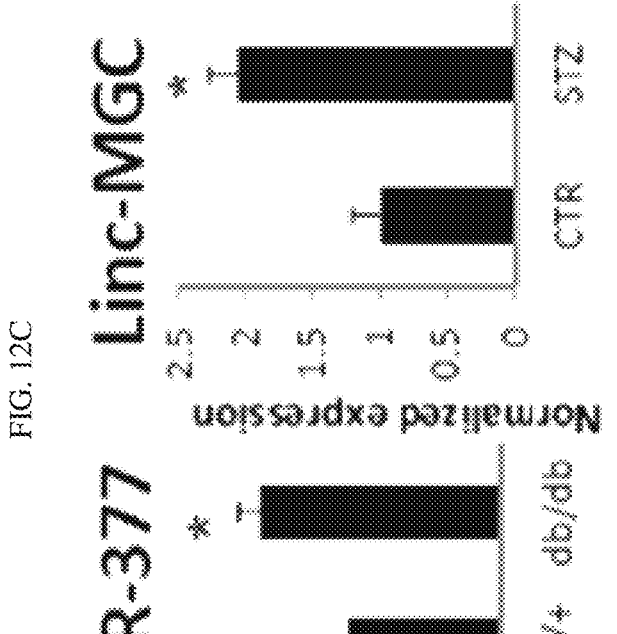
FIG. 12G
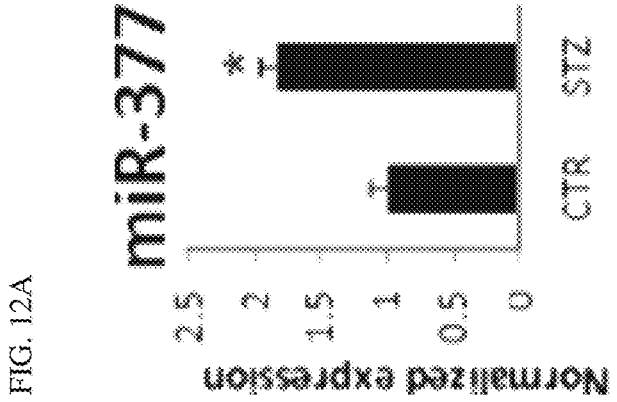

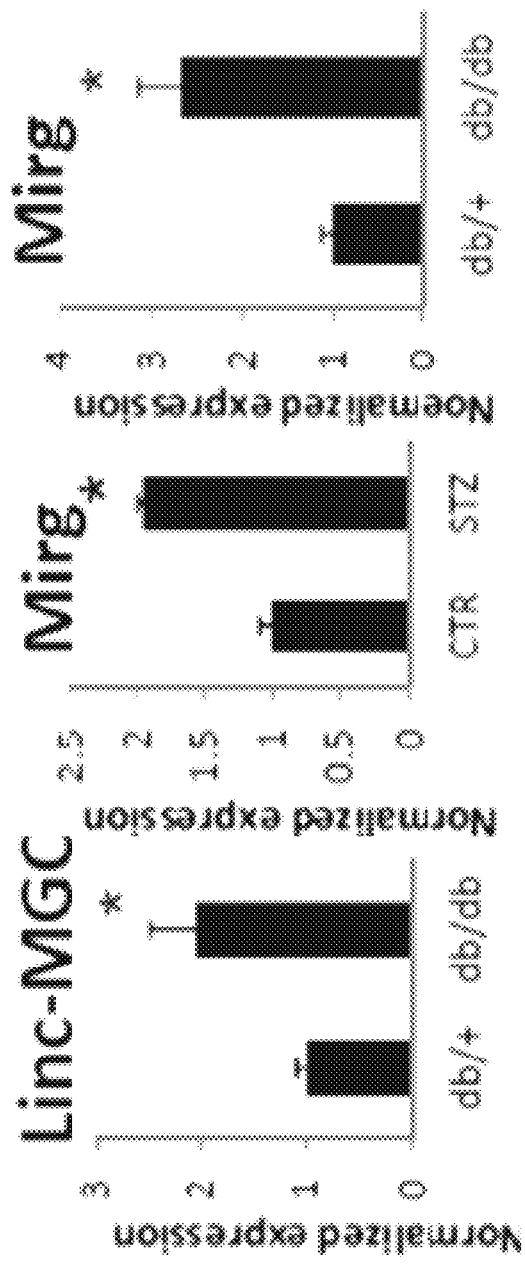
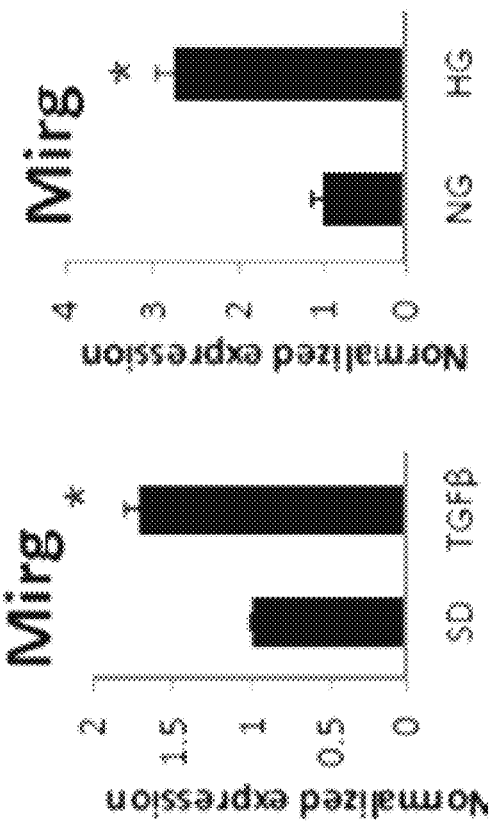
FIG. 12H  FIG. 12I  FIG. 12J  FIG. 12K  FIG. 12L

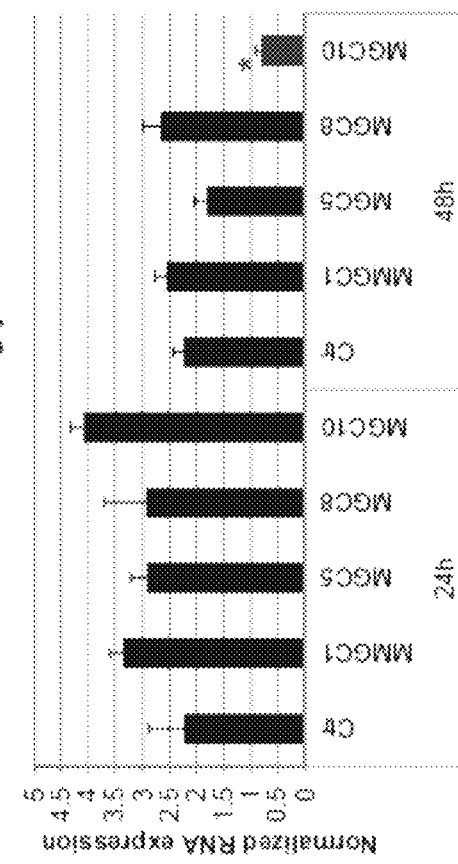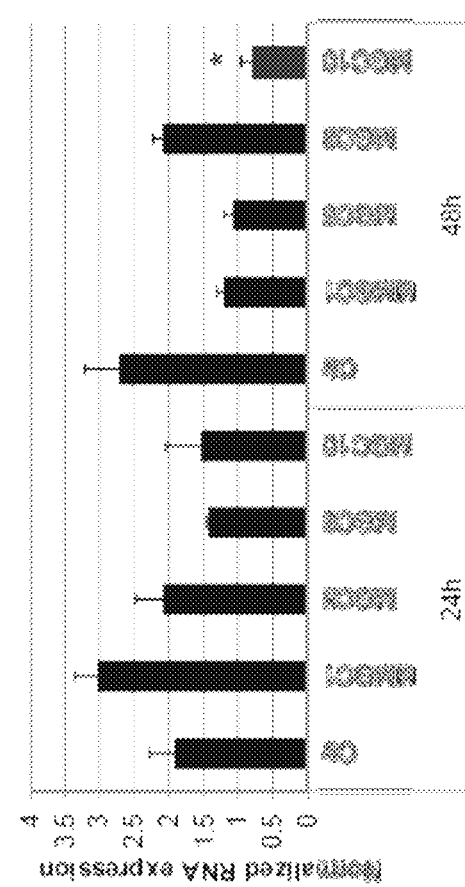

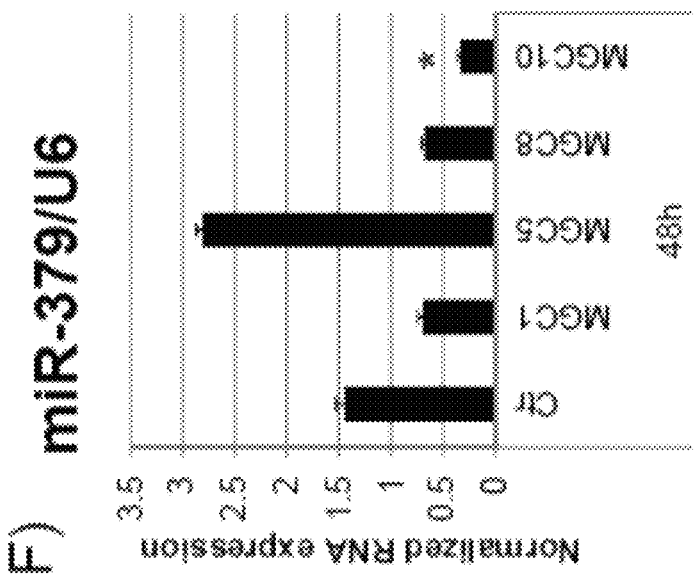
FIG. 16E
FIG. 16F

FIG. 20A

GGTTCCTGAAGAGATGGTAG—36bp deletion—AACATGGTCCACTAACTCTCAGTATCCAATCCATCCTCG

FIG. 20B

GGTTCCTGAAGAGATGGTAGACTATGGAACGTAGGCGTTATGTTTTGACCTATGTAACATGGTCCACTAACTCTCAGTATC
CAATCCATCCTCG

FIG. 20C

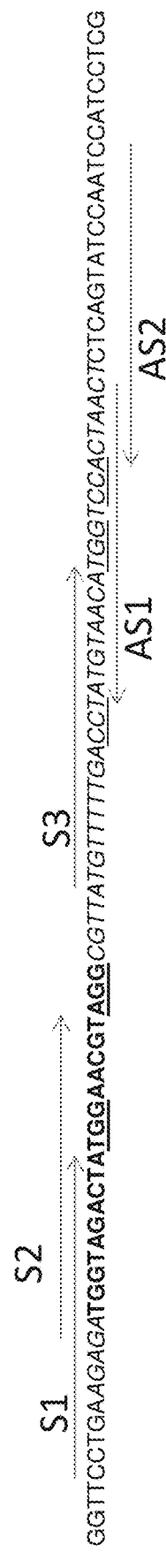

S1 →
S2 →
GGTTCCTGAAGAGATGGTAGACTATGGAACGTAGGCGTTATGTTTTGACCTATGTAACATGGTCCACTAACTCTCAGTATCCAATCCATCCTCG
                                        S3 →                    ← AS1
                                                                          ← AS2

Mature miR-379
*Precursor miR-379*

FIG. 20D

GGTTCCTGAAGAGTGGTAGA—36bp deletion—AACATGGTCCACTAACTCTCAGTATCCAATCCATCCTCG

Protein expression of EDEM3

SEQUENCE LISTING

```
<160> NUMBER OF SEQ ID NOS: 127

<210> SEQ ID NO 1
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 1
tgaaggccac actaac                                                   16

<210> SEQ ID NO 2
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 2
atgaaggcca cactaa                                                   16

<210> SEQ ID NO 3
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 3
gaaggccaca ctaac                                                    15

<210> SEQ ID NO 4
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 4
cacggtgctg aaagag                                                   16

<210> SEQ ID NO 5
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 5
acggtgctga aagaga                                                   16

<210> SEQ ID NO 6
<211> LENGTH: 15
<212> TYPE: DNA
<213> ORGANISM: Artificial Sequence
```

<220> FEATURE:
<223> OTHER INFORMATION: Synthetic polynucleotide

<400> SEQUENCE: 6
cggtgctgaa agaga                                                    15

<210> SEQ ID NO 7
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 7
tccttgaatg gttgca                                                   16

<210> SEQ ID NO 8
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 8
ttgaatggtt gcacgg                                                   16

<210> SEQ ID NO 9
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 9
cggtgctgaa agagag                                                   16

<210> SEQ ID NO 10
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 10
atttggcagt gggaag                                                   16

<210> SEQ ID NO 11
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 11
tttggcagtg ggaagc                                                   16

<210> SEQ ID NO 12
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 12
ttggcagtgg gaagca                                                   16

<210> SEQ ID NO 13
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 13
tcaaaaacat aacgcc                                                     16

<210> SEQ ID NO 14
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 14
gtcaaaaaca taacgc                                                     16

<210> SEQ ID NO 15
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 15
ggtcaaaaac ataacgc                                                    17

<210> SEQ ID NO 16
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 16
ggtcaaaaac ataacg                                                     16

<210> SEQ ID NO 17
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 17
aggtcaaaaa cataac                                                     16

<210> SEQ ID NO 18
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 18
aggtcaaaaa cataacg                                                    17

<210> SEQ ID NO 19
<211> LENGTH: 15
<212> TYPE: DNA
<213> ORGANISM: Artificial Sequence
<220> FEATURE:
<223> OTHER INFORMATION: Synthetic polynucleotide

```
<400> SEQUENCE: 19
taggtcaaaa acata                                                     15

<210> SEQ ID NO 20
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 20
caaaaacata acgcc                                                     15

<210> SEQ ID NO 21
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 21
gatttggcat tggaag                                                    16

<210> SEQ ID NO 22
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 22
ggaaggccat gtcaac                                                    16

<210> SEQ ID NO 23
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 23
ggcattgatg ggggaa                                                    16

<210> SEQ ID NO 24
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 24
tcagaaatca taacgcc                                                   17

<210> SEQ ID NO 25
<211> LENGTH: 287
<212> TYPE: DNA
<213> ORGANISM: Mus musculus

<400> SEQUENCE: 25 attttttctga gttagtgtgg ccttcatctg gtaatgtact acctgagggg ggaggtgccg    60
cctctctttc agcaccgtgc aaccattcaa ggagggtgtg ttgttcacca catctgcttc   120
ccactgccaa atcaggcctc agaaaagctt tctggaagtg acgccagctt cagggacaag   180
```

```
gcccaagttt ctaggggtca acaccgttcc atggttcctg aagagatggt agactatgga    240
acgtaggcgt tatgttttg acctatgtaa catggtccac taactct                   287
```

<210> SEQ ID NO 26
<211> LENGTH: 291
<212> TYPE: DNA
<213> ORGANISM: Homo sapiens

<400> SEQUENCE: 26

```
agtctttcca agttgacatg gccttcctgg aggaattacc acttagggta gaggcacccc    60
ttcccccatc aatgccactg ccccacattg gaggagggt tgtttatgtt caccatgtgc    120
ctgcttccaa tgccaaatcc agcctcagaa agctttctgg aagtgacgcc aacttcaggg    180
gcaaggccct ggttctgggg tcagcaccat tccgtggttc ctgaagagat ggtagactat    240
ggaacgtagg cgttatgatt tctgacctat gtaacatggt ccactaactc t             291
```

<210> SEQ ID NO 27
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 27

```
cctgaagaga tggtagacta tgg                                             23
```

<210> SEQ ID NO 28
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 28

```
caccgcctga agagatggta gacta                                           25
```

<210> SEQ ID NO 29
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 29

```
aaactagtct accatctctt caggc                                           25
```

<210> SEQ ID NO 30
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 30

```
gatggtagac tatggaacgt agg                                             23
```

<210> SEQ ID NO 31
<211> LENGTH: 25
<212> TYPE: DNA
<213> ORGANISM: Artificial Sequence
<220> FEATURE:
<223> OTHER INFORMATION: Synthetic polynucleotide

```
<400> SEQUENCE: 31
caccggatgg tagactatgg aacgt                                         25

<210> SEQ ID NO 32
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 32
aaacacgttc catagtctac catcc                                         25

<210> SEQ ID NO 33
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 33 tgttttgac ctatgtaaca tgg                                            23

<210> SEQ ID NO 34
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 34
caccgtgttt ttgacctatg taaca                                         25

<210> SEQ ID NO 35
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 35
aaactgttac ataggtcaaa aacac                                         25

<210> SEQ ID NO 36
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 36
cctatgtaac atggtccact aac                                           23

<210> SEQ ID NO 37
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 37
caccggttag tggaccatgt tacat                                         25
```

```
<210> SEQ ID NO 38
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 38
aaacatgtaa catggtccac taacc                                          25

<210> SEQ ID NO 39
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 39
ccactaactc tcagtatcca atc                                            23

<210> SEQ ID NO 40
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 40
caccggattg gatactgaga gttag                                          25

<210> SEQ ID NO 41
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 41
aaacctaact ctcagtatcc aatcc                                          25

<210> SEQ ID NO 42
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 42
ttaatacgac tcactatagg gatggtagac tatggaacgt                          40

<210> SEQ ID NO 43
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 43
ttaatacgac tcactatagg gttagtggac catgttacat                          40

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide
```

```
<400> SEQUENCE: 44
aaaagcaccg actcggtgcc                                                  20

<210> SEQ ID NO 45
<211> LENGTH: 95
<212> TYPE: DNA
<213> ORGANISM: Mus musculus

<400> SEQUENCE: 45
ggttcctgaa gagatggtag actatggaac gtaggcgtta tgttttttgac ctatgtaaca     60 tggtccacta actctcagta tccaatccat cctcg                                 95

<210> SEQ ID NO 46
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 46
ggttcctgaa gagatggtag aacatggtcc actaactctc agtatccaat ccatcctcg      59

<210> SEQ ID NO 47
<211> LENGTH: 95
<212> TYPE: DNA
<213> ORGANISM: Mus musculus

<400> SEQUENCE: 47
ggttcctgaa gagatggtag actatggaac gtaggcgtta tgttttttgac ctatgtaaca     60 tggtccacta actctcagta tccaatccat cctcg                                 95

<210> SEQ ID NO 48
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 48
ggttcctgaa gagtggtaga aacatggtcc actaactctc agtatccaat ccatcctcg      59

<210> SEQ ID NO 49
<211> LENGTH: 287
<212> TYPE: DNA
<213> ORGANISM: Mus musculus

<400> SEQUENCE: 49
atttttctga gttagtgtgg ccttcatctg gtaatgtact acctgagggg ggaggtgccg      60
cctctctttc agcaccgtgc aaccattcaa ggagggtgtg ttgttcacca catctgcttc    120
ccactgccaa atcaggcctc agaaaagctt tctggaagtg acgccagctt cagggacaag    180
gcccaagttt ctagggggtca acaccgttcc atggttcctg aagagatggt agactatgga   240
acgtaggcgt tatgttttttg acctatgtaa catggtccac taactct                  287

<210> SEQ ID NO 50
<211> LENGTH: 291
<212> TYPE: DNA
<213> ORGANISM: Homo sapiens
```

<400> SEQUENCE: 50

```
agtctttcca agttgacatg gccttcctgg aggaattacc acttagggta gaggcacccc    60
ttcccccatc aatgccactg ccccacattg gaggaggggt tgtttatgtt caccatgtgc   120
ctgcttccaa tgccaaatcc agcctcagaa agctttctgg aagtgacgcc aacttcaggg   180
gcaaggccct ggttctgggg tcagcaccat tccgtggttc ctgaagagat ggtagactat   240
ggaacgtagg cgttatgatt tctgacctat gtaacatggt ccactaactc t            291
```

<210> SEQ ID NO 51
<211> LENGTH: 297
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue is a or absent
<220> FEATURE:
<221> NAME/KEY: misc_feature
<222> LOCATION: (27)..(27)
<223> OTHER INFORMATION: Residue is a or absent
<220> FEATURE:
<221> NAME/KEY: misc_feature
<222> LOCATION: (28)..(28)
<223> OTHER INFORMATION: Residue is t or absent
<220> FEATURE:
<221> NAME/KEY: misc_feature
<222> LOCATION: (69)..(69)
<223> OTHER INFORMATION: Residue is c or absent
<220> FEATURE:
<221> NAME/KEY: misc_feature
<222> LOCATION: (80)..(80)
<223> OTHER INFORMATION: Residue is a or absent
<220> FEATURE:
<221> NAME/KEY: misc_feature
<222> LOCATION: (87)..(87)
<223> OTHER INFORMATION: Residue is a or absent
<220> FEATURE:
<221> NAME/KEY: misc_feature
<222> LOCATION: (107)..(107)
<223> OTHER INFORMATION: Residue is t or absent
<220> FEATURE:
<221> NAME/KEY: misc_feature
<222> LOCATION: (108)..(108)
<223> OTHER INFORMATION: Residue is a or absent
<220> FEATURE:
<221> NAME/KEY: misc_feature
<222> LOCATION: (109)..(109)
<223> OTHER INFORMATION: Residue is t or absent
<220> FEATURE:
<221> NAME/KEY: misc_feature
<222> LOCATION: (121)..(121)
<223> OTHER INFORMATION: Residue is g or absent
<220> FEATURE:
<221> NAME/KEY: misc_feature
<222> LOCATION: (122)..(122)
<223> OTHER INFORMATION: Residue is c or absent
<220> FEATURE:
<221> NAME/KEY: misc_feature
<222> LOCATION: (133)..(133)
<223> OTHER INFORMATION: Residue is c or absent
<220> FEATURE:
<221> NAME/KEY: misc_feature
<222> LOCATION: (155)..(155)
<223> OTHER INFORMATION: Residue is a or absent
<220> FEATURE:
<221> NAME/KEY: misc_feature
<222> LOCATION: (199)..(199)
<223> OTHER INFORMATION: Residue is t or absent
<220> FEATURE:
<221> NAME/KEY: misc_feature
<222> LOCATION: (202)..(202)
<223> OTHER INFORMATION: Residue is a or absent

```
<220> FEATURE:
<221> NAME/KEY: misc_feature
<222> LOCATION: (268)..(268)
<223> OTHER INFORMATION: Residue is c or absent

<400> SEQUENCE: 51
nrtytttcyr agttrryrtg gccttcnnct ggwrrwrtwm ymmctkaggg krgaggyrcc      60
scytcycynw tcaryrccrn tgcmmcncat tsraggaggg kktgttnnng ttcaccayrt    120
nnctgcttcc mantgccaaa tcmrgcctca gaaangcttt ctggaagtga cgccarcttc    180
agggrcaagg cccwrgttnc tngggtcar caccrttccr tggttcctga agagatggta    240
gactatggaa cgtaggcgtt atgwtttntg acctatgtaa catggtccac taactct      297

<210> SEQ ID NO 52
<211> LENGTH: 225
<212> TYPE: DNA
<213> ORGANISM: Mus musculus

<400> SEQUENCE: 52
tatagtcagc acagtggttc attttctga gttagtgtgg ccttcatctg gtaatgtact     60
acctgagggg ggaggtgccg cctctctttc agcaccgtgc aaccattcaa ggagggtgtg   120
ttgttcacca catctgcttc ccactgccaa atcaggcctc agaaaagctt tctggaagtg   180
acgccagctt cagggacaag gcccaagttt ctaggggtca acacc                   225

<210> SEQ ID NO 53
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 53
cttcccactg ccaaat                                                    16

<210> SEQ ID NO 54
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 54
atttggcagt gggaag                                                    16

<210> SEQ ID NO 55
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(16)
<223> OTHER INFORMATION: Residues modified with phosphorothioate
<220> FEATURE:
<221> NAME/KEY: modified_base
<222> LOCATION: (1)..(3)
<223> OTHER INFORMATION: Residues are LNA
<220> FEATURE:
<221> NAME/KEY: modified_base
<222> LOCATION: (14)..(16)
<223> OTHER INFORMATION: Residues are LNA
```

```
<400> SEQUENCE: 55
tcaaaaacat aacgcc                                              16

<210> SEQ ID NO 56
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(16)
<223> OTHER INFORMATION: Residues modified with phosphorothioate
<220> FEATURE:
<221> NAME/KEY: modified_base
<222> LOCATION: (1)..(3)
<223> OTHER INFORMATION: Residues are LNA
<220> FEATURE:
<221> NAME/KEY: modified_base
<222> LOCATION: (14)..(16)
<223> OTHER INFORMATION: Residues are LNA

<400> SEQUENCE: 56
cacggtgctg aaagag                                              16

<210> SEQ ID NO 57
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(16)
<223> OTHER INFORMATION: Residues modified with phosphorothioate
<220> FEATURE:
<221> NAME/KEY: modified_base
<222> LOCATION: (1)..(3)
<223> OTHER INFORMATION: Residues are LNA
<220> FEATURE:
<221> NAME/KEY: modified_base
<222> LOCATION: (14)..(16)
<223> OTHER INFORMATION: Residues are LNA

<400> SEQUENCE: 57
tgaaggccac actaac                                              16

<210> SEQ ID NO 58
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(16)
<223> OTHER INFORMATION: Residues modified with phosphorothioate
<220> FEATURE:
<221> NAME/KEY: modified_base
<222> LOCATION: (1)..(3)
<223> OTHER INFORMATION: Residues are LNA
<220> FEATURE:
<221> NAME/KEY: modified_base
<222> LOCATION: (14)..(16)
<223> OTHER INFORMATION: Residues are LNA

<400> SEQUENCE: 58
atttggcagt gggaag                                              16
```

```
<210> SEQ ID NO 59
<211> LENGTH: 25
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(24)
<223> OTHER INFORMATION: Residue is DNA
<220> FEATURE:
<221> NAME/KEY: misc_feature
<222> LOCATION: (25)..(25)
<223> OTHER INFORMATION: Residue is DNA

<400> SEQUENCE: 59
caucugcuuc ccacugccaa aucag                                            25

<210> SEQ ID NO 60
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 60
cugauuuggc agugggaagc agaugug                                          27

<210> SEQ ID NO 61
<211> LENGTH: 25
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(24)
<223> OTHER INFORMATION: Residue is DNA
<220> FEATURE:
<221> NAME/KEY: misc_feature
<222> LOCATION: (25)..(25)
<223> OTHER INFORMATION: Residue is DNA

<400> SEQUENCE: 61
ucagcaccgu gcaaccauuc aagga                                            25

<210> SEQ ID NO 62
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 62
uccuugaaug guugcacggu gcugaaa                                          27

<210> SEQ ID NO 63
<211> LENGTH: 25
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(24)
<223> OTHER INFORMATION: Residue is DNA
<220> FEATURE:
<221> NAME/KEY: misc_feature
<222> LOCATION: (25)..(25)
<223> OTHER INFORMATION: Residue is DNA
```

```
<400> SEQUENCE: 63
cuucaucugg uaauguacua ccuga                                         25

<210> SEQ ID NO 64
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 64
ucagguagua cauuaccaga ugaaggc                                       27

<210> SEQ ID NO 65
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 65
ggaugcaagg uaucagaugg u                                             21

<210> SEQ ID NO 66
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 66
uagguuaucc guguugccuu cg                                            22

<210> SEQ ID NO 67
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 67
gaaguuguuc gugguggauu cg                                            22

<210> SEQ ID NO 68
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 68
uucaccuaca aggagauacu a                                             21

<210> SEQ ID NO 69
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 69
cucuaaccgg uacauuauga gu                                            22
```

```
<210> SEQ ID NO 70
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 70
agguuacccg agcaacuuug cau                                            23

<210> SEQ ID NO 71
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 71
uucuucacgu ggcgcuuaca aa                                             22

<210> SEQ ID NO 72
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 72
gtcctttcct aataaaatga ggaaattgca tcgcattgtc tgagtaggtg tc            52

<210> SEQ ID NO 73
<211> LENGTH: 198
<212> TYPE: DNA
<213> ORGANISM: Artificial Sequence
<220> FEATURE:
<223> OTHER INFORMATION: Synthetic polynucleotide

<400> SEQUENCE: 73
aagtgacgcc agcttcaggg acaaggccca agtttctagg ggtcaacacc gttccatggt   60
tcctgaagag agtcctttcc taataaaatg aggaaattgc atcgcattgt ctgagtaggt  120
gtcgacatgt aacatggtcc actaactctc agtatccaat ccatcctcgg agggcacccc  180
ggaggtgtta ccaacagc                                                198

<210> SEQ ID NO 74
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 74
uguuuucaac ggaaacacac ua                                             22

<210> SEQ ID NO 75
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 75
uauguaguau gguccacauc uu                                             22
```

```
<210> SEQ ID NO 76
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 76
uucuucacgu gguacaaaca aa                                              22

<210> SEQ ID NO 77
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 77 agggacccccg agggagggca gg                                             22

<210> SEQ ID NO 78
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 78
ugcccccucc aggaagccuu cu                                              22

<210> SEQ ID NO 79
<211> LENGTH: 77
<212> TYPE: DNA
<213> ORGANISM: Artificial Sequence
<220> FEATURE:
<223> OTHER INFORMATION: Synthetic polynucleotide

<400> SEQUENCE: 79
ttccgtggtt cctgaagaga tggtagacta tggaacgtag gcgttatgat ttctgaccta    60
tgtaacatgg tccacta                                                   77

<210> SEQ ID NO 80
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 80
ttccgtggtt cctgaagaga tgg                                             23

<210> SEQ ID NO 81
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 81
ccgtggttcc tgaagagatg gta                                             23

<210> SEQ ID NO 82
<211> LENGTH: 23
<212> TYPE: DNA
<213> ORGANISM: Artificial Sequence
```

```
<220> FEATURE:
<223> OTHER INFORMATION: Synthetic polynucleotide

<400> SEQUENCE: 82
gatttctgac ctatgtaaca tgg                                              23

<210> SEQ ID NO 83
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 83
ugcaccuaaa aggagauacu a                                                21

<210> SEQ ID NO 84
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 84 uauguggau gguaaaccgc uu                                                22

<210> SEQ ID NO 85
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 85
ugcaccuuaa aggagauaca a                                                21

<210> SEQ ID NO 86
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 86
uguccgguag acacaauaua a                                                21

<210> SEQ ID NO 87
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 87
cuccaaaggg cacauacaaa gu                                               22

<210> SEQ ID NO 88
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 88
augguugacc auagaacaug cg                                               22
```

<210> SEQ ID NO 89
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 89
aauaauacau gguugaucuu u                                              21

<210> SEQ ID NO 90
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 90
ucucucucag acggaacau au                                              22

<210> SEQ ID NO 91
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 91
aaaggauucu gcugucgguc ccacu                                          25

<210> SEQ ID NO 92
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 92
uuucuccaau ugguccacac aa                                             22

<210> SEQ ID NO 93
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 93
ugucucucga acgggaacau au                                             22

<210> SEQ ID NO 94
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 94
gcaugcgaua ugccagauga u                                              21

<210> SEQ ID NO 95
<211> LENGTH: 22
<212> TYPE: RNA
<213> ORGANISM: Artificial Sequence
<220> FEATURE:
<223> OTHER INFORMATION: Synthetic polynucleotide

```
<400> SEQUENCE: 95 gggagacca guuggucagu gu                                           22

<210> SEQ ID NO 96
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 96
ggaugcaagg uaucagaugg u                                           21

<210> SEQ ID NO 97
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 97
uagguuaucc guguugccuu cg                                          22

<210> SEQ ID NO 98
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 98
gaaguuguuc gugguggauu cg                                          22

<210> SEQ ID NO 99
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 99
uuguaccuaa aaggagauac ua                                          22

<210> SEQ ID NO 100
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 100
cucuaaccgg uacauuauga gu                                          22

<210> SEQ ID NO 101
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 101
agguuacccg agcaacuuug cau                                         23
```

```
<210> SEQ ID NO 102
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 102
uucuucacgu ggcgcuuaca aa                                              22

<210> SEQ ID NO 103
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 103
uguuuucaac ggaaacacac ua                                              22

<210> SEQ ID NO 104
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 104
uauguaauau gguccacauc uu                                              22

<210> SEQ ID NO 105
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 105
uucuucacgu gguacaaaca aa                                              22

<210> SEQ ID NO 106
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 106
uauguggaau gguaaaccgc uu                                              22

<210> SEQ ID NO 107
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 107
ugcacuuuaa aggagauaca a                                               21

<210> SEQ ID NO 108
<211> LENGTH: 21
<212> TYPE: RNA
<213> ORGANISM: Artificial Sequence
<220> FEATURE:
<223> OTHER INFORMATION: Synthetic polynucleotide
```

```
<400> SEQUENCE: 108
uguccgguag acacaauaua a                                              21

<210> SEQ ID NO 109
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 109
cuccaaaggg cacauacaaa gu                                             22

<210> SEQ ID NO 110
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 110
augguugacc auagaacaug cg                                             22

<210> SEQ ID NO 111
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 111
aauaauacau gguugaucuu u                                              21

<210> SEQ ID NO 112
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 112
aagggauucu gauguugguc acacu                                          25

<210> SEQ ID NO 113
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 113
uuuuuccaau cgacccacac aa                                             22

<210> SEQ ID NO 114
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 114
ugucucucga acgggaacau au                                             22
```

```
<210> SEQ ID NO 115
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 115
gcaugcgaua ugccagauga u                                              21

<210> SEQ ID NO 116
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 116
uguuuucaac ggaaacacac ua                                             22

<210> SEQ ID NO 117
<211> LENGTH: 169
<212> TYPE: DNA
<213> ORGANISM: Artificial Sequence
<220> FEATURE:
<223> OTHER INFORMATION: Synthetic polynucleotide

<400> SEQUENCE: 117
ggtcaacacc gttccatggt tcctgaagag aggttcctga agagatggta gactatggaa    60
cgtaggcgtt atgtttttga cctatgtaac atggtccact aactctcagt atccaatcca   120
tcctcgatgt aacatggtcc actaactctc agtatccaat ccatcctcg               169

<210> SEQ ID NO 118
<211> LENGTH: 287
<212> TYPE: RNA
<213> ORGANISM: Mus musculus

<400> SEQUENCE: 118
auuuuucuga guuagugugg ccuucaucug guaauguacu accugagggg ggaggugccg    60
ccucucuuuc agcaccgugc aaccauucaa ggagggugug uuguuccacca caucugcuuc  120 ccacugccaa aucaggccuc agaaaagcuu ucuggaagug acgccagcuu cagggacaag   180
gcccaaguuu cuaggggguca acaccguucc auguuccug aagagauggu agacuaugga   240
acguaggcgu uauguuuuug accauaguaa caugguccac uaacucu                 287

<210> SEQ ID NO 119
<211> LENGTH: 291
<212> TYPE: RNA
<213> ORGANISM: Homo sapiens

<400> SEQUENCE: 119
agucuuucca aguugacaug gccuuccugg aggaauuacc acuuagggua gaggcacccc    60 uuccccauc aaugccacug ccccacauug gaggaggggu uguuuauguu caccaugugc    120
cugcuuccaa ugccaaauccc agccucagaa agcuuucugg aagugacgcc aacuucaggg   180
gcaaggcccu gguucugggg ucagcaccau uccgugguuc cugaagagau gguagacuau   240
ggaacguagg cguuauugauu ucugaccuau guaacauggu ccacuaacuc u            291
```

```
<210> SEQ ID NO 120
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 120
caccgttccg tggttcctga agaga                                    25

<210> SEQ ID NO 121
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 121
aaactctctt caggaaccac ggaac                                    25

<210> SEQ ID NO 122
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 122
caccggattt ctgacctatg taaca                                    25

<210> SEQ ID NO 123
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 123
aaactgttac ataggtcaga aatcc                                    25

<210> SEQ ID NO 124
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 124
caccgtacca tctcttcagg aacca                                    25

<210> SEQ ID NO 125
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 125
aaactggttc ctgaagagat ggtac                                    25

<210> SEQ ID NO 126
<211> LENGTH: 25
<212> TYPE: DNA
<213> ORGANISM: Artificial Sequence
<220> FEATURE:
<223> OTHER INFORMATION: Synthetic polynucleotide
```

```
<400> SEQUENCE: 126
caccgccata gtctaccatc tcttc                                         25

<210> SEQ ID NO 127
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 127
aaacgaagag atggtagact atggc                                         25
```

COMPOUNDS OF CHEMICALLY MODIFIED OLIGONUCLEOTIDES AND METHODS OF USE THEREOF

CROSS-REFERENCE TO RELATED APPLICATIONS

This application claims the benefit of priority under 35 U.S.C. § 119(e) to U.S. Provisional Application No. 62/166,533, filed May 26, 2015 which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. NIH R01 DK081705 awarded by the National Institute of Diabetes and Digestive and Kidney Diseases (NIDDK). The Government has certain rights to this invention.

SEQUENCE SUBMISSION

The present application is being filed along with a Sequence Listing in electronic format. The Sequence Listing is entitled 48440-565001US_ST25.txt, was created on May 23, 2016, and is 30,720 bytes in size. The information in the electronic format of the Sequence Listing is part of the present application and is incorporated herein by reference in its entirety.

BACKGROUND OF THE DISCLOSURE

Diabetic nephropathy (DN) is one of the most common complications of diabetes and a major cause of renal failure, which requires painful dialysis. Although key therapeutic interventions have been implemented to treat DN, diabetic patients continue to reach end-stage renal disease at alarming proportions. It is therefore imperative to identify new targets. Key features of DN include the expansion and hypertrophy of glomerular mesangial cells (MCs), increased accumulation of extracellular matrix (ECM) proteins such as collagen 1 alpha1 (Col1α1), Col1α2, Col4α1 and fibronectin, and tubulointerstitial fibrosis, podocyte dysfunction and proteinuria.

BRIEF SUMMARY OF THE DISCLOSURE

The current disclosure provides, inter alia, an isolated compound including a nucleic acid sequence capable of hybridizing to an RNA sequence 10 to 270 nucleobases downstream of the transcription start site of a mammalian microRNA-379 transcript; method of treating diabetic nephropathy in a subject with the compound; method of inhibiting expression of a mammalian microRNA-379 megacluster with the compound.

In embodiments, the compound includes a nucleic acid sequence having a nucleobase analog. In embodiments, the nucleic acid sequence includes Locked Nucleic Acid (LNA), 2'-O-alkyl, 2' O-Methyl, 2'-deoxy-2'fluoro, 2'-deoxy, a universal base, 5-C-methyl, an inverted deoxy abasic residue incorporation, or any combination thereof. In embodiments, the nucleic acid sequence may include analogs with positive backbones; non-ionic backbones, modified sugars, and non-ribose backbones (e.g. phosphorodiamidate morpholino oligos).

The current disclosure provides an isolated compound including a nucleic acid sequence having at least 90% sequence identity with a continuous 10 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24. The current disclosure further provides a pharmaceutical composition including a compound of this disclosure, and a pharmaceutically acceptable diluent, carrier, salt or adjuvant.

Other features and advantages of the disclosure will be apparent from the following detailed description and claims.

Unless noted to the contrary, all publications, references, patents and/or patent applications reference herein are hereby incorporated by reference in their entirety for all purposes.

BRIEF DESCRIPTION OF THE DRAWINGS

FIG. 2A is a diagram showing the mega cluster of microRNAs (miRNAs) and their upstream promoter region. FIG. 2B depicts bar graphs showing up-regulation of cluster miRNAs and the host long noncoding RNA (lnc-RNA) in glomerular mesangial cells (MC) obtained from glomeruli of diabetic and control mice.

FIGS. 12A-12F are bar graphs of normalized expression of microRNAs in the Lnc-MGC, the host of microRNA-379 cluster, under normal (CTR, db/+) and diabetic conditions (db/db or streptozotocin (STZ)). FIGS. 12G-12J are bar graphs of normalized expression of Linc-MGC, Mirg (another lncRNA located in the locus of miRNA-379 cluster) under normal (CTR, db/+) and diabetic conditions (db/db or streptozotocin (STZ)). FIGS. 12K-12L are bar graphs of Mirg expression under when treated with normal glucose (NG), serum depletion (SD), TGFβ, or high glucose (HG) conditions.

FIGS. 16C-16L are bar graphs of normalized RNA expression. MGC10 transfection inhibited expression of lnc-MGC significantly at 48 hours after MGC10 transfection. MCG10 also reduced the expression of lnc-MGC even after TGFβ treatment. Some miRNAs in miR-379 cluster were reduced by MCG10 in MMC. Several targets (EDEME3, Tnrc6b, and Phf21a) of miR-379 cluster were also upregulated by MGC10, suggesting that downregulation of miR-379 cluster restores the target expression.

FIG. 17A is a diagram of mouse receiving subcutaneous injection of 5 mg/kg MGC10. FIGS. 17B-17F are bar graphs of normalized RNA expression after subcutaneous injection of 5 mg/kg MGC10, which consistently inhibited the expression of lnc-MGC in kidney cortex at 24-72 hours after injection. Three mice in each group were injected. The expression of lnc-MGC (FIG. 17B) and miRNAs in the miR-379 cluster, miR-379 (FIG. 17C), miR-495 (FIG. 17D), miR-377 (FIG. 17E) were inhibited by subcutaneous injection of 5 mg/kg MGC10, while miR-882 outside of the cluster was not (FIG. 17F). Three mice were injected for each condition and each time point. Gene expression quantified in cortical samples are shown. Results are mean+SE in triplicate PCRs from each mouse, *, P<0.05. These results suggest that MGC10 is effective to reduce the expression of lnc-MGC and miR-379 cluster miRNAs.

FIGS. 19A and 19B depict Human homologue of lnc-MGC (hlnc-MGC) and its inhibition by HMGC10 in human MC. Significant increase of hlnc-MGC, miR-379, miR-494, miR495, miR-377 in human MC (HMC) treated with TGF-β1 (FIG. 19A) or HG (FIG. 19B) relative to respective controls (SD or NG), but not miR-882 (outside of miR-379 cluster). These increases were significantly reduced in HMC transfected with HMGC10 compared to control oligo. FIG. 19C depicts HMGC10 mediated restoration of miR-370 cluster targets, EDEM3, ATF3, CUGBP2 and CPEB4 which were inhibited by TGF-β1 in HMC. FIG. 19D depicts significant increase of pro-fibrotic genes, TGF-β1, COL1A2, COL4A1, F1 and CTGF in HMC treated with TGF-B1 and their significant inhibition ion HMC transfected with HMGC10. FIG. 19E depicts HMGC10 mediated restoration of miR-379 cluster targets, EDEM3, ATF3, CGBP2 and CPEB4 which were inhibited by HG in HMC. FIG. 19F depicts significant increase of pro-fibrotic genes, TGF-β1, COL1A2, COL4A1, FN1 and CTGF in HMC treated with HG which was significantly inhibited by HMGC10. Result are mean+SE in triplicate PCRs from three-four independent culture experiments. *, P<0.05.

FIGS. 20A-20D are depictions of genomic region of mouse with a 36 base pair deletion in the miR-379 locus, generated using the CRISPR/CAS9 system as described in FIG. 11. FIG. 20A represents SEQ ID NO: 46; FIG. 20B represents SEQ ID NO: 47; FIG. 20C represents SEQ ID NO: 47 with the guide RNAs; and FIG. 20D represents SEQ ID NO: 48.

FIG. 21A depicts relative expression of miR-379 in kidney mesangial cells from three miR-379KO mice compared to wild type mice. FIG. 21B depicts relative protein expression of EDEM3 (western blot (left panel) and bar graph (right panel)), a target of miR-379, from miR-379KO mice compared to wild type mice.

DETAILED DESCRIPTION OF THE DISCLOSURE

Figure 1:
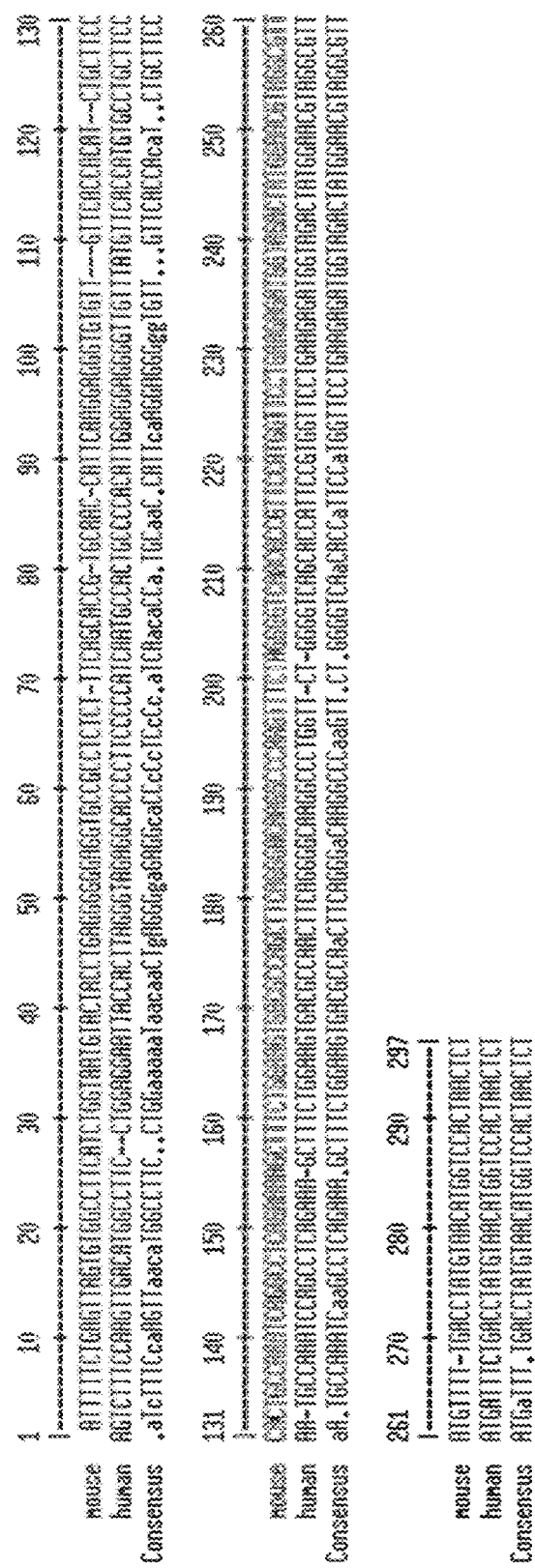
FIG. 1 depicts an alignment of the upstream sequences of mouse and human microRNA-379 region. Sequence legend: mouse (SEQ ID NO:49); human (SEQ ID NO:50); consensus (SEQ ID NO:51). The transcript of mouse miR-379 is SEQ ID NO: 118, and that of human miR-379 is SEQ ID NO: 119.

Provided herein is, inter alia, an isolated compound including a nucleic acid sequence capable of hybridizing to an RNA sequence 10 to 270 nucleobases downstream of the transcription start site of a mammalian microRNA-379 transcript; method of treating diabetic nephropathy in a subject with the compound; method of inhibiting expression of a mammalian microRNA-379 megacluster.

In embodiments, the compound includes a nucleic acid sequence having a nucleobase analog. In embodiments, the nucleic acid sequence includes Locked Nucleic Acid (LNA), 2'-O-alkyl, 2' O-Methyl, 2'-deoxy-2'fluoro, 2'-deoxy, a universal base, 5-C-methyl, an inverted deoxy abasic residue incorporation, or any combination thereof. In embodiments, the nucleic acid sequence may include analogs with positive backbones; non-ionic backbones, modified sugars, and non-ribose backbones (e.g. phosphorodiamidate morpholino oligos).

The current disclosure provides an isolated compound including a nucleic acid sequence having at least 90% sequence identity with a continuous 10 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24. The current disclosure further provides a pharmaceutical composition including a compound of this disclosure, and a pharmaceutically acceptable diluent, carrier, salt or adjuvant.

The following definitions are included for the purpose of understanding the present subject matter and for constructing the appended patent claims. Abbreviations used herein have their conventional meaning within the chemical and biological arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

"Nucleic acid" or "oligonucleotide" or "polynucleotide" or grammatical equivalents used herein means at least two nucleotides covalently linked together. The term "nucleic acid" includes single-, double-, multiple-stranded or branched DNA, RNA and analogs (derivatives) thereof.

The term "modified internucleotide linkage" or "internucleotide linkage analogue" and the like refers, in the usual and customary sense, to a non-physiologic linkage between nucleotides. For example, the term "phosphorothioate nucleic acid" refers to a nucleic acid in which one or more internucleotide linkages are through a phosphorothioate moiety (thiophosphate) moiety. The phosphorothioate moiety may be a monothiophosphate ($-P(O)_3(S)^{3-}-$) or a dithiophosphate ($-P(O)_2(S)_2^{3-}-$). In embodiments, one or more of the nucleosides of a phosphorothioate nucleic acid are linked through a phosphorothioate moiety (e.g. monothiophosphate) moiety, and the remaining nucleosides are linked through a phosphodiester moiety ($-P(O)_4^{3-}-$). In embodiments, one or more of the nucleosides of a phosphorothioate nucleic acid are linked through a phosphorothioate moiety (e.g. monothiophosphate) moiety, and the remaining nucleosides are linked through a methylphosphonate linkage. In embodiments, all the nucleosides of a phosphorothioate nucleic acid are linked through a phosphorothioate moiety (e.g. a monothiophosphate) moiety.

As used herein, phosphorothioate oligonucleotides (phosphorothioate nucleic acids) are from about 5, 6, 7, 8, 9, 10, 11, 12, 13, 14, 15, 16, 17, 18, 19, 20, 21, 22, 23, 24, 25, 26, 27, 28, 29, or 30 nucleotides in length. In embodiments, the phosphorothioate nucleic acids herein contain one or more phosphodiester bonds. In other embodiments, the phosphorothioate nucleic acids include alternate backbones (e.g., mimics or analogs of phosphodiesters as known in the art, such as, boranophosphate, methylphosphonate, phosphoramidate, or O-methylphosphoroamidite linkages (see Eckstein, Oligonucleotides and Analogues: A Practical Approach, Oxford University Press).

In embodiments, the phosphorothioate nucleic acids may include one or more nucleic acid analog monomers known in the art, such as, peptide nucleic acid monomer or polymer, locked nucleic acid monomer or polymer, morpholino monomer or polymer, glycol nucleic acid monomer or polymer, or threose nucleic acid monomer or polymer. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. Phosphorothioate nucleic acids and phosphorothioate polymer backbones can be linear or branched. For example, the branched nucleic acids are repetitively branched to form higher ordered structures such as dendrimers and the like.

The terms "analog," "nucleobase analog" and the like, in the context of nucleic acid bases refer, in the usual and customary sense, to chemical moieties that can substitute for normal (i.e., physiological) nucleobases (i.e., A, T, G, C and U) in nucleic acids. Nucleobase analogs can be categorized as purine analogs and pyrimidine analogs. Purine analogs have a core purine ring structure which is substituted to form a purine analog. Pyrimidine analogs have a core pyrimidine ring structure which is substituted to form a pyrimidine analog. Substitution may be endocyclic (i.e., within the purine or pyrimidine ring structure) or exocyclic (i.e., attached to the purine or pyrimidine ring structure). Exemplary nucleobase analogs include, but are not limited to: 1,5-dimethyluracil, 1-methyluracil, 2-amino-6-hydroxyaminopurine, 2-aminopurine, 3-methyluracil, 5-(hydroxymethyl)cytosine, 5-bromouracil, 5-carboxycytosine, 5-fluoroorotic acid, 5-fluorouracil, 5-formylcytosine, 5-formyluracil, 6-azathymine, 6-azauracil, 8-azaadenine, 8-azaguanine, N6-carbamoylmethyladenine, N6-hydroxyadenine, allopurinol, hypoxanthine, thiouracil, locked nucleic acid (LNA), 2'-O-alkyl nucleobase, 2'-Fluoro nucleobase, and 2'-OMe nucleobase.

As used herein, locked nucleic acid (LNA) is a modified RNA nucleotide. LNAs are RNA molecules which possess an extra bridge connecting the 2' oxygen and 4' carbon of the ribose moiety. The ribose becomes locked in the 3'-endo (North) conformation. Base stacking and backbone pre-organization are enhanced by the locked ribose conformation. In embodiments, LNA modification has several advantages, including reduced toxicity, lower dosing, higher affinity and efficient targeting.

As used herein the term "nucleobases" refers to the naturally occurring compounds, which form the differentiating component of nucleotides; five bases occur in nature, three of which are common to RNA and DNA (uracil replaces thymine in RNA). Bases are divided into two groups, purines and pyrimidines, based on their chemical structure. Purines are larger, double-ring molecules comprising adenine and guanine, whereas pyrimidines have only a single-ring structure and comprise cytosine and thymine/uracil. Because of the different size of the two types of nucleobases, purines can only base pair with pyrimidines in order to preserve the DNA molecule's constant width. More specifically, the only base pairs that will fit the structure of the particular molecule are adenine-thymine and cytosine-guanine.

The term "cell" as used herein also refers to individual cells, cell lines, or cultures derived from such cells. A "culture" refers to a composition comprising isolated cells of the same or a different type.

Diabetic nephropathy (DN) is typically defined by macroalbuminuria—that is, a urinary albumin excretion of more than 300 mg in a 24-hour collection—or macroalbuminuria and abnormal renal function as represented by an abnormality in serum creatinine, calculated creatinine clearance, or glomerular filtration rate (GFR). Clinically, diabetic nephropathy is characterized by a progressive increase in proteinuria and decline in GFR, hypertension, and a high risk of cardiovascular morbidity and mortality.

As used herein, "early stage DN" or "incipient DN" is characterized by microalbuminuria, which is defined as levels of albumin ranging from 30 to 300 mg in a 24-h urine collection. Microalbuminuria progresses to overt nephropathy. Renal disease is suspected to be secondary to diabetes in the clinical setting of long-standing diabetes. This is supported by the history of diabetic retinopathy, particularly in type 1 diabetics, in whom there is a strong correlation. The natural history of diabetic nephropathy is a process that progresses gradually over years.

Renal biopsy findings consistent with diabetic nephropathy in the early stages of DN are mesangial expansion and glomerular basement membrane thickening. Eventual progression of diabetic nephropathy can lead to nodular glomerulosclerosis, also referred to as Kimmelstiel-Wilson disease.

Early diabetes is heralded by glomerular hyperfiltration and an increase in GFR. This is believed to be related to increased cell growth and expansion in the kidneys, possibly mediated by hyperglycemia itself. Microalbuminuria typically occurs after 5 years in type 1 diabetes. Overt nephropathy, with urinary protein excretion higher than 300 mg/day, often develops after 10 to 15 years. ESRD develops in 50% of type 1 diabetics, with overt nephropathy within 10 years.

Type 2 diabetes has a more variable course. Patients often present at diagnosis with microalbuminuria because of delays in diagnosis and other factors affecting protein excretion. Fewer patients with microalbuminuria progress to advanced renal disease. Without intervention, approximately 30% progress to overt nephropathy and, after 20 years of nephropathy, approximately 20% develop ESRD. Because of the high prevalence of type 2 compared with type 1 diabetes, however, most diabetics on dialysis are type 2 diabetics.

Long-standing hyperglycemia is known to be a significant risk factor for the development of diabetic nephropathy. Hyperglycemia may directly result in mesangial expansion and injury by an increase in the mesangial cell glucose concentration. The glomerular mesangium expands initially by cell proliferation and then by cell hypertrophy. Increased mesangial stretch and pressure can stimulate this expansion, as can high glucose levels. Transforming growth factor β (TGF-β) is particularly important in the mediation of expansion and later fibrosis via the stimulation of collagen and fibronectin. Glucose can also bind reversibly and eventually irreversibly to proteins in the kidneys and circulation to form advanced glycosylation end products (AGEs). AGEs can form complex cross-links over years of hyperglycemia and can contribute to renal damage by stimulation of growth and fibrotic factors via receptors for AGEs. In addition, mediators of proliferation and expansion, including platelet-derived growth factor, TGF-β, and vascular endothelial growth factor (VEGF) that are elevated in diabetic nephropathy can contribute to further renal and microvascular complications.

Proteinuria, a marker and potential contributor to renal injury, accompanies diabetic nephropathy. Increased glomerular permeability will allow plasma proteins to escape into the urine. Some of these proteins will be taken up by the proximal tubular cells, which can initiate an inflammatory response that contributes to interstitial scarring eventually leading to fibrosis. Tubulointerstitial fibrosis is seen in advanced stages of diabetic nephropathy and is a better predictor of renal failure than glomerular sclerosis. Hyperglycemia, angiotensin II, TGF-β, and likely proteinuria itself all play roles in stimulating this fibrosis. There is an epithelial-mesenchymal transition that takes place in the tubules, with proximal tubular cell conversion to fibroblast-like cells. These cells can then migrate into the interstitium and produce collagen and fibronectin.

In diabetic nephropathy, the activation of the local renin-angiotensin system occurs in the proximal tubular epithelial cells, mesangial cells, and podocytes. Angiotensin II (ATII) itself contributes to the progression of diabetic nephropathy. ATII is stimulated in diabetes despite the high-volume state typically seen with the disease, and the intrarenal level of ATII is typically high, even in the face of lower systemic concentrations. ATII preferentially constricts the efferent arteriole in the glomerulus, leading to higher glomerular capillary pressures. In addition to its hemodynamic effects, ATII also stimulates renal growth and fibrosis through ATII type 1 receptors, which secondarily upregulate TGF-β and other growth factors.

Control of hypertension has clearly shown to be an important and powerful intervention in decreasing the progression of diabetic nephropathy. In diabetics who have disordered autoregulation at the level of the kidney, systemic hypertension can contribute to endothelial injury. Human studies of type 2 diabetics have shown that blood pressure lowering, regardless of the agent used, retards the onset and progression of diabetic nephropathy. In animal studies, the degree and severity of the diabetic nephropathy were strongly linked to systemic blood pressure.

The fact that most types 1 and 2 diabetics do not develop diabetic nephropathy (DN) suggests that other factors may be involved. Genetic factors clearly play a role in the predisposition to diabetic nephropathy in family members who have DN, and linkage to specific areas on the human genome is evolving. The theory of a reduction in nephron number at birth indicates that individuals born with a reduced number of glomeruli may be predisposed to subsequent renal injury and progressive nephropathy. This has been shown in animal studies in which the mother was exposed to hyperglycemia at the time of pregnancy. If this linkage is true in humans, that would have important implications concerning the role of maternal factors in the eventual development of kidney disease.

Diabetic nephropathy (DN) include the expansion and hypertrophy of glomerular mesangial cells (MCs), increased accumulation of extracellular matrix (ECM) proteins such as collagen 1alpha1 (Col1α1), Col1α2, Col4α1 and fibronectin, and tubulointerstitial fibrosis, podocyte dysfunction and proteinuria. Levels of transforming growth factor-beta1 (TGF-β1) are increased in MCs and other renal cells in diabetics and TGF-β1 mediates many of the adverse effects. Several biochemical mechanisms of action have been reported for TGF-β1. Factors relevant to the pathogenesis of DN such as angiotensin II, and high glucose (HG), increase TGF-β1 expression in MCs in vitro and in vivo. Signals from the activated TGF-β1 receptor complex are transduced to the nucleus by Smad proteins, including Smad2/3/4, which regulate TGF-β-induced genes, including PAI-1, collagen and p21cip1/waf1. However, the molecular mechanisms by which diabetic conditions and TGF-β1 regulate the genes that increase the hypertrophy, protein synthesis and fibrosis associated with DN are not fully clear. A few microRNAs (miRNAs or miRs, in short) are involved in mediating the pro-fibrotic effects of TGF-β1 in MCs in vitro and diabetic conditions in vivo.

microRNAs (miRNA) are endogenously produced, short single-stranded non-coding RNAs (~20-23 nucleotides) that play key roles in post-transcriptional regulation of gene expression to silence genes by repressing the translation or inducing the degradation of target mRNAs. There are more than 1000 mammalian miRNAs that can target nearly 60% of mRNAs in the genome, and therefore, they regulate many key cellular functions. The terms microRNA, miRNA, and miR are interchangeable.

Long ncRNAs (lncRNAs) are long transcripts that range from >200 nucleotides up to ~100 kb, and are similar to messenger RNAs (mRNAs) but lack protein coding (translation) potential. LncRNAs can regulate the expression of local and distal genes by various mechanisms that include recruiting histone modifying complexes and modulating the activities of transcription factors (TFs). LncRNAs also serve as hosts for miRNAs and/or a miRNA megacluster. LncRNAs have cell-specific expression, and function in various biological processes including transcription, differentiation, and the immune response.

As used herein, the microRNA megacluster is a region of the genome where more than 10 microRNA genes are encoded. In embodiments, 35-60 microRNAs are encoded in the region. In embodiments, some of these clustered miRNA genes may be encoded by a single-copy DNA sequence. Alternatively, the miRNA genes may be arranged in tandem arrays of closely related sequences.

As used herein, the microRNA-379 transcript is a RNA sequence transcribed from a microRNA-379 gene of a mammalian genome, e.g., a human genome. In its ordinary meaning, a "transcript" in molecular biology or similar context is a product of transcription. miRNAs are transcribed as much larger primary transcripts (pri-miRNAs). The vast majority of mature miRNAs are produced from primary transcripts of microRNAs (pri-miRNAs) by a multi-step pathway. In mammals, miRNAs are first transcribed as longer primary transcripts called primary miRNA (pri-miRNA). The transcript may contain multiple miRNA stem loops and is capped at the 5' end through polyadenylation. Drosha, a nuclear RNase III, is recruited to crop the pri-miRNA transcript into a hairpin-shaped structure, about 70 nt long, known as precursor-miRNA (pre-miRNA). This cleavage event is critical and site-specific, as it determines the mature miRNA sequence. The pre-miRNA is then exported out of the nucleus for further cleavage into a 22 nt duplex. The complementary strand becomes degraded leaving one fully mature miRNA strand. Mature miRNA then associate with several members of the Argonaute protein family to form the RNA-induced silencing complex which then binds to specific protein-coding mRNA transcripts, directing mRNA inactivation by translational repression, deadenylation, or degradation.

As used herein, plasminogen activator inhibitor-1 (PAI-1) is an endothelial plasminogen activator inhibitor or serpin E1 is a protein that in humans is encoded by the SERPINE1 gene. PAI-1 is a serine protease inhibitor (serpin) that functions as the principal inhibitor of tissue plasminogen activator (tPA) and urokinase (uPA), the activators of plasminogen and hence fibrinolysis (the physiological breakdown of blood clots). It is a serine protease inhibitor (serpin) protein (SERPINE1). Other PAI, plasminogen activator inhibitor-2 (PAI-2) is secreted by the placenta and only present in significant amounts during pregnancy. In addition, protease nexin acts as an inhibitor of tPA and urokinase. PAI-1, however, is the main inhibitor of the plasminogen activators.

As used herein, connective-tissue growth factor (CTGF) is a secreted protein implicated in multiple cellular events including angiogenesis, skeletogenesis and wound healing.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

"Patient," "subject," "patient in need thereof," and "subject in need thereof" are herein used interchangeably and refer to a living organism suffering from or prone to a disease or condition that can be treated by administration using the methods and compositions provided herein. Non-limiting examples include humans, other mammals, bovines, rats, mice, dogs, monkeys, goat, sheep, cows, deer, and other non-mammalian animals. In some embodiments, a patient is human. Tissues, cells and their progeny of a biological entity obtained in vitro or cultured in vitro are also contemplated.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

The term "inhibiting" also means reducing an effect (disease state or expression level of a gene/protein/mRNA) relative to the state in the absence of a compound or composition of the present disclosure.

A "test compound" as used herein refers to an experimental compound used in a screening process to identify activity, non-activity, or other modulation of a particularized biological target or pathway.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Disease" or "condition" refer to a state of being or health status of a patient or subject capable of being treated with the compounds or methods provided herein. In some instances, "disease" or "condition" refers to diabetes nephropathy (DN).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture. In some embodiments contacting includes allowing a compound described herein to interact with a protein or enzyme.

The terms "phenotype" and "phenotypic" as used herein refer to an organism's observable characteristics such as onset or progression of disease symptoms, biochemical properties, or physiological properties.

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.1-18.88). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "promoter" and the like in the usual and customary sense, is a region of DNA that initiates transcription of a particular gene. Promoters are located near the transcription start sites of genes, on the same strand and upstream on the DNA (towards the 5' region of the sense strand). Upstream and downstream in the usual and customary sense both refer to a relative position in DNA or RNA. Each strand of DNA or RNA has a 5' end and a 3' end, so named for the carbon position on the deoxyribose (or ribose) ring. By convention, upstream and downstream relate to the 5' to 3' direction in which RNA transcription takes place. Upstream is toward the 5' end of the RNA molecule and downstream is toward the 3' end. When considering double-stranded DNA, upstream is toward the 5' end of the coding strand for the gene in question and downstream is toward the 3' end. Due to the anti-parallel nature of DNA, this means the 3' end of the template strand is upstream of the gene and the 5' end is downstream.

The term "an amount of" in reference to a polynucleotide or polypeptide, refers to an amount at which a component or element is detected. The amount may be measured against a control, for example, wherein an increased level of a particular polynucleotide or polypeptide in relation to the control, demonstrates enrichment of the polynucleotide or polypeptide. The term refers to quantitative measurement of the enrichment as well as qualitative measurement of an increase or decrease relative to a control.

Throughout the description and claims of this specification the word "comprise" and other forms of the word, such as "comprising" and "comprises," means including but not limited to, and is not intended to exclude, for example, other components.

"Analog," "analogue," or "derivative" is used in accordance with its plain ordinary meaning within Chemistry and Biology and refers to a chemical agent that is structurally similar to another agent (i.e., a so-called "reference" agent) but differs in composition, e.g., in the replacement of one atom by an atom of a different element, or in the presence of a particular functional group, or the replacement of one functional group by another functional group, or the absolute stereochemistry of a chiral center of the reference agent. In some embodiments, a derivative may be a conjugate with a pharmaceutically acceptable agent, for example, phosphate or phosphonate.

As used herein, the term "salt" refers to acid or base salts of the agents used herein. Illustrative but non-limiting examples of acceptable salts are mineral acid (hydrochloric acid, hydrobromic acid, phosphoric acid, sulfuric acid, and the like) salts, organic acid (acetic acid, propionic acid, glutamic acid, citric acid, and the like) salts, and quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, which is combined with buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

An "adjuvant" (from Latin, adiuvare: to aid) is a pharmacological and/or immunological agent that modifies the effect of other agents.

A "diluent" (also referred to as a filler, dilutant or thinner) is a diluting agent. Certain fluids are too viscous to be pumped easily or too dense to flow from one particular point to the other. This can be problematic, because it might not be economically feasible to transport such fluids in this state. To ease this restricted movement, diluents are added. This decreases the viscosity of the fluids, thereby also decreasing the pumping/transportation costs.

The terms "administration" or "administering" refer to the act of providing an agent of the current embodiments or pharmaceutical composition including an agent of the current embodiments to the individual in need of treatment.

By "co-administer" it is meant that a composition described herein is administered at the same time, just prior to, or just after the administration of additional therapies. The compound or the composition of the disclosure can be administered alone or can be co-administered to the patient. Co-administration is meant to include simultaneous or sequential administration of the compound individually or in combination (more than one compound or agent). The preparations can also be combined, when desired, with other active substances (e.g. to reduce metabolic degradation).

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and. Other modes of delivery include, but are not limited to, the use of liposomal formulations, intravenous infusion, transdermal patches, etc.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Bioniater Sci. Polym. Ed.* 7:623-645, 1995; as biodegradable and injectable gel formulations (see, e.g., Gao *Phann. Res.* 12:857-863, 1995); or, as microspheres for oral administration (see, e.g., Eyles, *J. Phann. Pharmacol.* 49:669-674, 1997).

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

Pharmaceutical compositions may include compositions wherein the therapeutic drug (e.g., agents described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of therapeutic drug effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and agents of this disclosure. Adjustment and manipulation of established dosages (e.g., frequency and duration) are well within the ability of those skilled in the art.

For any therapeutic agent described herein, the therapeutically effective amount can be initially determined from cell culture assays. Target concentrations will be those concentrations of therapeutic drug(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring agent's effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the therapeutic drug being employed. The dose administered to a patient should be sufficient to effects a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the agent. Thereafter, the dosage is increased by small increments until the optimum effect under circumstances is reached. Dosage amounts and intervals can be adjusted individually to provide levels of the administered agent effective for the particular clinical indication being treated. This will provide a therapeutic regimen that is commensurate with the severity of the individual's disease state.

A weight percent of a component, unless specifically stated to the contrary, is based on the total weight of the formulation or composition in which the component is included.

"Excipient" is used herein to include any other agent that may be contained in or combined with a disclosed agent, in which the excipient is not a therapeutically or biologically active agent/agent. As such, an excipient should be pharmaceutically or biologically acceptable or relevant (for example, an excipient should generally be non-toxic to the individual). "Excipient" includes a single such agent and is also intended to include a plurality of excipients. For the purposes of the present disclosure the term "excipient" and "carrier" are used interchangeably in some embodiments of the present disclosure and said terms are defined herein as, "ingredients which are used in the practice of formulating a safe and effective pharmaceutical composition."

The term "about" refers to any minimal alteration in the concentration or amount of an agent that does not change the efficacy of the agent in preparation of a formulation and in treatment of a disease or disorder. The term "about" with respect to concentration range of the agents (e.g., therapeutic/active agents) of the current disclosure also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Compound

The present disclosure includes an isolated compound including a nucleic acid sequence capable of hybridizing to an RNA sequence 10 to 270 nucleobases downstream of the transcription start site of a mammalian microRNA-379 transcript or a microRNA-379 megacluster transcript. In embodiments, the present disclosure includes an isolated compound including a nucleic acid sequence capable of hybridizing to at least one nucleic acid base of a downstream region of the transcription start site of a mammalian microRNA-379 transcript or a microRNA-379 megacluster transcript. In embodiments, the transcript is as exists immediately after transcription, e.g., primary transcript mRNA or pre-mRNA. In embodiments, the compound includes a nucleic acid sequence having a nucleobase analog or modified internucleotide linkage.

In embodiments, the compound includes a nucleic acid sequence having a nucleobase analog. In embodiments, the nucleic acid sequence includes Locked Nucleic Acid (LNA), 2'-O-alkyl, 2' O-Methyl, 2'-deoxy-2'fluoro, 2'-deoxy, a universal base, 5-C-methyl, an inverted deoxy abasic residue incorporation, or any combination thereof. In embodiments, the nucleic acid sequence may include analogs with positive backbones; non-ionic backbones, modified sugars, and non-ribose backbones (e.g. phosphorodiamidate morpholino oligos), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids.

In embodiments, the nucleic acid sequence includes at least one nucleic acid analog. In embodiments, the nucleic acid sequence includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In embodiments, a nucleic acid sequence includes or is DNA. In embodiments, a nucleic acid sequence includes or is RNA. In embodiments, a nucleic acid sequence includes or is a nucleic acid having internucleotide linkages selected from phosphodiesters and phosphodiester derivatives (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof). In embodiments, a nucleic acid sequence consists of a nucleic acid having internucleotide linkages selected from phosphodiesters and phosphorothioates. In embodiments, a nucleic acid sequence includes or is a nucleic acid having backbone linkages selected from phosphodiesters and phosphorodithioates. In embodiments, a nucleic acid sequence includes or is a nucleic acid having phosphodiester backbone linkages. In embodiments, a nucleic acid sequence includes or is a nucleic acid having phosphorothioate backbone linkages. In embodiments, a nucleic acid sequence includes or is a nucleic acid having phosphorodithioate backbone linkages.

In embodiments, a nucleic acid sequence in the compound includes a nucleic acid analog (e.g. LNA, 2'-O-alkyl, 2'-Fluoro, or 2' O-Methyl (2'-OMe)) at 1, 2, 3, 4, 5, 6, 7, 8, 9, or 10 nucleobases. In embodiments, the compound includes a nucleic acid sequence capable of hybridizing to an RNA sequence 10 to 270 nucleobases downstream of the transcription start site of a mammalian microRNA-379 transcript, where the nucleic acid sequence has an analog (e.g., LNA, 2'-O-alkyl, 2'-Fluoro, or 2' O-Methyl (2'-OMe)) at 1, 2, 3, 4, 5, 6, 7, 8, 9, or 10 nucleobases. In embodiments, the compound includes a nucleic acid sequence with an analog (e.g., LNA, 2'-O-alkyl, 2'-Fluoro, or 2' O-Methyl (2'-OMe)) at 3 nucleobases.

In embodiments, the nucleobase analog is at the 5'-end or the 3'-end of the nucleic acid sequence. In embodiments, the nucleobase analog (e.g., LNA, 2'-O-alkyl, 2'-Fluoro, or 2' O-Methyl (2'-OMe)) is at the 5'-end or the 3'-end of the nucleic acid sequence. In embodiments, the nucleobase analog (e.g., LNA, 2'-O-alkyl, 2'-Fluoro, or 2'-OMe) is at the 5'-end and the 3'-end of the nucleic acid sequence.

In embodiments, the nucleic acid sequence includes three, four or five nucleobase analogs (e.g., LNA, 2'-O-alkyl, 2'-Fluoro, or 2' O-Methyl (2'-OMe)) at the 5'-end or the 3'-end of the nucleic acid sequence. In embodiments, the nucleic acid sequence includes three, four or five nucleobase analogs (e.g., LNA, 2'-O-alkyl, 2'-Fluoro, or 2' O-Methyl (2'-OMe)) at the 5'-end and the 3'-end of the nucleic acid sequence. In embodiments, the nucleic acid sequence includes three nucleobase analogs (e.g., LNA, 2'-O-alkyl, 2'-Fluoro, or 2' O-Methyl (2'-OMe)) at the 5'-end or the 3'-end of the nucleic acid sequence. In embodiments, the nucleic acid sequence includes three nucleobase analogs (e.g., LNA, 2'-O-alkyl, 2'-Fluoro, or 2' O-Methyl (2'-OMe)) at the 5'-end and the 3'-end of the nucleic acid sequence In embodiments, the compound includes a nucleic acid sequence with a modified internucleotide linkage. In embodiments, the modified internucleotide linkage is a phosphorothioate (also known as phosphothioate) linkage. In other embodiments, nucleic acid analogs are included that may have alternate backbones (e.g. phosphodiester derivatives), including, e.g., phosphoramidate, phosphorodiamidate, phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, the compound includes a nucleic acid sequence with internal modified internucleotide linkage between nucleobases at one or more positions. In embodiments, the compound includes a nucleic acid sequence with internal modified internucleotide linkage between nucleobases at one or more positions, and one, two, three, or four nucleobase analogs at the 5'- or the 3'-ends of the nucleic acid sequence. In embodiments, the compound includes a nucleic acid sequence with internal internucleotide phosphorothioate linkage between nucleobases at one or more positions, and one, two, three, or four nucleobase LNA analogs at the 5'- or the 3'-ends of the nucleic acid sequence. In embodiments, the compound includes a nucleic acid sequence with internal modified internucleotide linkage between nucleobases at one or more positions, and one, two, three, or four nucleobase analogs at the 5'- and the 3'-ends of the nucleic acid sequence. In embodiments, the compound includes a nucleic acid sequence with internal internucleotide phosphorothioate linkage between nucleobases at one or more positions, and one, two, three, or four nucleobase LNA analogs at the 5'- and the 3'-ends of the nucleic acid sequence.

Structures of exemplary molecules for internucleotide analogyes, such as an LNA monomer, and internucleotide linkages, such as phosphodiester linkage and phosphorothioate linkage, are depicted below.

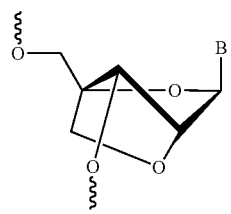

LNA monomer

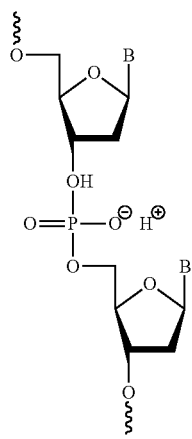

5'-3' Phosphodiester linkage

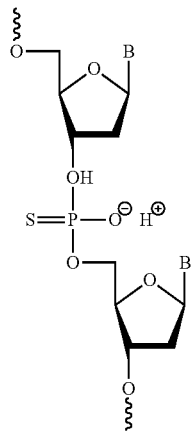

5'-3' Phosphorothioate linkage

In embodiments, the RNA sequence to which a nucleic acid sequence of the present disclosure hybridizes to includes 11 to 27, 61 to 93, 115 to 139, or 246 to 265 nucleobases downstream of the transcription start site of the gene. In embodiments, the target site on the RNA sequence to which a nucleic acid sequence of the present disclosure hybridizes to is listed in Table 1. The target site range listed in Table 1 (middle column) reflects the nucleobase positions counting from the transcription start site at +1 of a target RNA.

TABLE 1

| Nucleic Acid Identity | Target site | Nucleic acid sequence |
|---|---|---|
| MGC8 | +11 to +26 | TGAAGGCCACACTAAC (SEQ ID NO: 1) |
| MGC12 | +12 to +27 | ATGAAGGCCACACTAA (SEQ ID NO: 2) |
| MGC15 | +11 to +25 | GAAGGCCACACTAAC (SEQ ID NO: 3) |

TABLE 1-continued

| Nucleic Acid Identity | Target site | Nucleic acid sequence |
|---|---|---|
| MGC5 | +64 to +79 | CACGGTGCTGAAAGAG (SEQ ID NO: 4) |
| MGC6 | +63 to +78 | ACGGTGCTGAAAGAGA (SEQ ID NO: 5) |
| MGC13 | +63 to +77 | CGGTGCTGAAAGAGA (SEQ ID NO: 6) |
| MGC14 | +78 to +93 | TCCTTGAATGGTTGCA (SEQ ID NO: 7) |
| MGC18 | +75 to +90 | TTGAATGGTTGCACGG (SEQ ID NO: 8) |
| MGC20 | +62 to +77 | CGGTGCTGAAAGAGAG (SEQ ID NO: 9) |
| MGC10 | +117 to +132 | ATTTGGCAGTGGGAAG (SEQ ID NO: 10) |
| MGC17 | +116 to +131 | TTTGGCAGTGGGAAGC (SEQ ID NO: 11) |
| MGC19 | +115 to +130 | TTGGCAGTGGGAAGCA (SEQ ID NO: 12) |
| MGC1 | +246 to +261 | TCAAAAACATAACGCC (SEQ ID NO: 13) |
| MGC2 | +247 to +262 | GTCAAAAACATAACGC (SEQ ID NO: 14) |
| MGC3 | +248 to +262 | GGTCAAAAACATAACGC (SEQ ID NO: 15) |
| MGC4 | +248 to +263 | GGTCAAAAACATAACG (SEQ ID NO: 16) |
| MGC7 | +249 to +264 | AGGTCAAAAACATAAC (SEQ ID NO: 17) |
| MGC9 | +249 to +263 | AGGTCAAAAACATAACG (SEQ ID NO: 18) |
| MGC11 | +251 to +265 | TAGGTCAAAAACATA (SEQ ID NO: 19) |
| MGC16 | +246 to +260 | CAAAAACATAACGCC (SEQ ID NO: 20) |
| HMGC10 | +124 to +139 | GATTTGGCATTGGAAG (SEQ ID NO: 21) |
| HMGC8 | +12 to +27 | GGAAGGCCATGTCAAC (SEQ ID NO: 22) |
| HMGC5 | +61 to +76 | GGCATTGATGGGGGAA (SEQ ID NO: 23) |
| HMGC1 | +249 to +265 | TCAGAAATCATAACGCC (SEQ ID NO: 24) |

In embodiments, compound includes, e.g., GATTTGGCATTGGAAG (SEQ ID NO: 21) with internal internucleotide phosphorothioate linkage between one or more nucleobases, and one, two, three, or four nucleobase LNA analogs at the 5'- and/or the 3'-ends of the nucleic acid sequence. The LNA analogs at the 5' and/or the 3'-ends of the sequence are underlined, e.g., GATTTGGCATTGGAAG (SEQ ID NO: 21). In embodiments, the remaining internal internucleotide linkages between nucleobases (italicized in the above sequence) are phosphorothioate linkages. In embodiments, a compound is, e.g., GATTTGGCATTGGAAG (SEQ ID NO: 21), with internal internucleotide phosphorothioate linkage between one or more nucleobases.

In embodiments, the compound includes a nucleic acid that binds to the mouse miR-379 transcript including the upstream region of mouse miR-379 and the mouse miR-379 sequence. The sequence of the mouse miR-379 transcript including the upstream region of mouse miR-379 and the mouse miR-379 sequence is shown in SEQ ID NO: 118. The nucleic acid sequences of SEQ ID NOs: 1-20 hybridize to a region of mouse miR-379 transcript of SEQ ID NO: 25 (the transcription start site indicated with "+1"), i.e., SEQ ID NO: 118; in SEQ ID NO: 118, a uracil ("U") replaces each thymine ("T") of SEQ ID NO: 25.

+1
(SEQ ID NO: 25)
ATTTTTCTGAGTTAGTGTGGCCTTCATCTGGTAATGTACTACCTGAG

GGGGGAGGTGCCGCCTCTCTTTCAGCACCGTGCAACCATTCAAGGA

GGGTGTGTTGTTCACCACATCTGCTTCCCACTGCCAAATCAGGCCT

CAGAAAAGCTTTCTGGAAGTGACGCCAGCTTCAGGGACAAGGCCC

AAGTTTCTAGGGGTCAACACCGTTCCATGGTTCCTGAAGAGATGGT

AGACTATGGAACGTAGGCGTTATGTTTTTGACCTATGTAACATGGT

CCACTAACTCT

+1
(SEQ ID NO: 118)
AUUUUUCUGAGUUAGUGUGGCCUUCAUCUGGUAAUGUACUACCU

GAGGGGGGAGGUGCCGCCUCUCUUUCAGCACCGUGCAACCAUUC

AAGGAGGGUGUGUUGUUCACCACAUCUGCUUCCCACUGCCAAAU

CAGGCCUCAGAAAAGCUUUCUGGAAGUGACGCCAGCUUCAGGGA

CAAGGCCCAAGUUUCUAGGGGUCAACACCGUUCCAUGGUUCCUG

-continued
AAGAGAUGGUAGACUAUGGAACGUAGGCGUUAUGUUUUUG

ACCUAUGUAACAUGGUCCACUAACUCU

In embodiments, the compound includes a nucleic acid that binds to the human miR-379 transcript including the upstream region of human miR-379 and the human miR-379 sequence. The sequence of the human miR-379 transcript including the upstream region of human miR-379 and the human miR-379 sequence is shown in SEQ ID NO: 119. The nucleic acid sequences of SEQ ID NOs: 21-24 hybridize to a region of human miR-379 transcript of SEQ ID NO: 26 (the transcription start site indicated with "+1"), i.e., SEQ ID NO: 119; in SEQ ID NO: 119, a uracil ("U") replaces each thymine ("T") of SEQ ID NO: 26.

In embodiments, a nucleic acid sequence having 90-91%, 91-92%, 92-93%, 93-94%, 94-95%, 95-96%, 96-97%, 97-98%, or 98-99% sequence identity with a continuous 10 nucleobase sequence of SEQ ID NO: 1, 2, 3, 4, 5, 6, 7, 8, 9, 10, 11, 12, 13, 14, 15, 16, 17, 18, 19, or 20 hybridizes to a region of human miR-379 transcript of SEQ ID NO: 26, i.e., SEQ ID NO: 119; in SEQ ID NO: 119, a uracil ("U") replaces each thymine ("T") of SEQ ID NO: 26.

+1
(SEQ ID NO: 26)
AGTCTTTCCAAGTTGACATGGCCTTCCTGGAGGAATTACCACTTAG

GGTAGAGGCACCCCTTCCCCCATCAATGCCACTGCCCCACATTGGA

GGAGGGGTTGTTTATGTTCACCATGTGCCTGCTTCCAATGCCAAAT

CCAGCCTCAGAAAGCTTTCTGGAAGTGACGCCAACTTCAGGGGCA

AGGCCCTGGTTCTGGGGTCAGCACCATTCCGTGGTTCCTGAAGAGA

TGGTAGACTATGGAACGTAGGCGTTATGATTTCTGACCTATGTAAC

ATGGTCCACTAACTCT.

+1
(SEQ ID NO: 119)
AGUCUUUCCAAGUUGACAUGGCCUUCCUGGAGGAAUUACCACUU

AGGGUAGAGGCACCCCUUCCCCCAUCAAUGCCACUGCCCCACAUU

GGAGGAGGGGUUGUUUAUGUUCACCAUGUGCCUGCUUCCAAUGC

CAAAUCCAGCCUCAGAAAGCUUUCUGGAAGUGACGCCAACUUCA

GGGGCAAGGCCCUGGUUCUGGGGUCAGCACCAUUCCGUGGUUCC

UGAAGAGAUGGUAGACUAUGGAACGUAGGCGUUAUGAUUUCUG

ACCUAUGUAACAUGGUCCACUAACUCU

The consensus sequence of the mouse and human miR-379 transcript corresponds to a transcript of the consensus sequence provided in SEQ ID NO: 51.

In embodiments, the compound includes a nucleic acid sequence that is 10 to 30 nucleobases in length. In embodiments, the compound includes a nucleic acid sequence capable of hybridizing at least 5, 6, 7, 8, 9, 10, 11, 12, 13, 14, 15, 16, 17, 18, 19, 20, 21, 22, 23, 24, 25, 26, 27, 28, 29, or 30 nucleobases within a RNA sequence 10 to 270 nucleobases downstream of the transcription start site of a mammalian microRNA-379 transcript. In embodiments, the mammalian microRNA-379 transcript is a human microRNA-379 transcript. In embodiments, the compound includes a nucleic acid sequence capable of hybridizing at least 5, 6, 7, 8, 9, 10, 11, 12, 13, 14, 15, 16, 17, 18, 19, 20, 21, 22, 23, 24, 25, 26, 27, 28, 29, or 30 nucleobases within the sequence of SEQ ID NO: 118 or 119. In embodiments, the compound includes a nucleic acid sequence capable of hybridizing at least 5, 6, 7, 8, 9, 10, 11, 12, 13, 14, 15, 16, 17, 18, 19, 20, 21, 22, 23, 24, 25, 26, 27, 28, 29, or 30 nucleobases within 10-20, 10-30, 20-40, 20-50, 40-60, 40-70, 60-80, 60-90, 80-100, 80-110, 100-120, 100-130, 120-140, 120-150, 140-160, 140-170, 160-180, 160-190, 180-200, 180-210, 200-220, 200-230, 220-240, 220-230, 240-260, or 240-270 nucleobases downstream of the transcription start site (indicated with "+1") of the transcript sequence of SEQ ID NO: 25 or 26 (i.e., transcript sequence SEQ ID NO: 118 or 119), a sequence including the transcript of SEQ ID NO: 25 or 26 (i.e., transcript sequence SEQ ID NO: 118 or 119), or a variation thereof. In embodiments, the compound includes a nucleic acid sequence capable of hybridizing at least 5 nucleobases within the sequence of 10-20, 10-30, 20-40, 20-50, 40-60, 40-70, 60-80, 60-90, 80-100, 80-110, 100-120, 100-130, 120-140, 120-150, 140-160, 140-170, 160-180, 160-190, 180-200, 180-210, 200-220, 200-230, 220-240, 220-230, 240-260, or 240-270 nucleobases downstream of the transcription start site (indicated with "+1") of the transcript of SEQ ID NO: 25 or 26 (i.e., transcript sequence SEQ ID NO: 118 or 119).

In embodiments, the compound includes a nucleic acid sequence capable of hybridizing at least 5 nucleobases within a RNA sequence 10 to 270 nucleobases downstream of the transcription start site of a mammalian microRNA-379 transcript. In embodiments, the compound includes a nucleic acid sequence capable of hybridizing at least 5 nucleobases within a RNA sequence 10-20, 10-30, 20-40, 20-50, 40-60, 40-70, 60-80, 60-90, 80-100, 80-110, 100-120, 100-130, 120-140, 120-150, 140-160, 140-170, 160-180, 160-190, 180-200, 180-210, 200-220, 200-230, 220-240, 220-230, 240-260, or 240-270 nucleobases downstream of the transcription start site of a mammalian microRNA-379 transcript.

In embodiments, the present disclosure includes a compound including a nucleic acid sequence having 90-91%, 91-92%, 92-93%, 93-94%, 94-95%, 95-96%, 96-97%, 97-98%, 98-99%, or 99-100% sequence identity with a continuous 10 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, or analogues or derivatives thereof.

In embodiments, the compound includes a nucleic acid sequence having 90-91%, 91-92%, 92-93%, 93-94%, 94-95%, 95-96%, 96-97%, 97-98%, 98-99%, or 99-100% sequence identity with a continuous 10 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal modified internucleotide linkage between nucleobases and/or terminal nucleobase analogs at the 5'- and/or the 3'-ends of the nucleic acid sequence.

In embodiments, the compound includes a nucleic acid sequence having 90-91%, 91-92%, 92-93%, 93-94%, 94-95%, 95-96%, 96-97%, 97-98%, 98-99%, or 99-100% sequence identity with a continuous 10 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or terminal nucleobase LNA analogs at the 5'- and/or the 3'-ends of the nucleic acid sequence. In embodiments, the nucleobase analogs at the 5'- and/or the 3' ends may be 2'-O-alkyl nucleobase, 2'-Fluoro nucleobase, or 2'-OMe nucleobase.

In embodiments, the present disclosure includes a compound including a nucleic acid sequence having at least 90% sequence identity with a continuous 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24.

In embodiments, the compound includes a nucleic acid sequence having at least 90% sequence identity with a continuous 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal modified internucleotide linkage between nucleobases and/or terminal nucleobase analogs at the 5'- and/or the 3'-ends of the nucleic acid sequence.

In embodiments, the compound includes a nucleic acid sequence having at least 90% sequence identity with a continuous 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or nucleobase LNA analogs at the 5'- and/or the 3'-ends of the nucleic acid sequence. In embodiments, the nucleobase analogs at the 5'- and the 3' ends may be 2'-O-alkyl nucleobase, 2'-Fluoro nucleobase, or 2'-OMe nucleobase, and any combination thereof.

In embodiments, the present disclosure includes a compound including a nucleic acid sequence having 90-91%, 91-92%, 92-93%, 93-94%, 94-95%, 95-96%, 96-97%, 97-98%, 98-99%, or 99-100% sequence identity with a continuous 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24.

In embodiments, the compound includes a nucleic acid sequence having 90-91%, 91-92%, 92-93%, 93-94%, 94-95%, 95-96%, 96-97%, 97-98%, 98-99%, or 99-100% sequence identity with a continuous 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal modified internucleotide linkage between nucleobases and/or terminal nucleobase analogs at the 5'- and/or the 3'-ends of the nucleic acid sequence.

In embodiments, the compound includes a nucleic acid sequence having 90-91%, 91-92%, 92-93%, 93-94%, 94-95%, 95-96%, 96-97%, 97-98%, 98-99%, or 99-100% sequence identity with a continuous 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or nucleobase LNA analogs at the 5'- and/or the 3'-ends of the nucleic acid sequence. In embodiments, the nucleobase analogs at the 5'- and/or the 3' ends may be 2'-O-alkyl nucleobase, 2'-Fluoro nucleobase, or 2'-OMe nucleobase, and any combination thereof.

Complex

In embodiments, the present disclosure provides a complex of a compound including a nucleic acid sequence described in this disclosure hybridized to an RNA sequence 10 to 270 nucleobases downstream of the transcription start site of a mammalian microRNA-379 transcript or a microRNA-379 megacluster transcript.

In embodiments, the present disclosure includes a nucleic acid sequence of SEQ ID NOs: 1-20 hybridized to a region of mouse miR-379 transcript of SEQ ID NO: 25 (i.e., transcript sequence SEQ ID NO: 118) to form a complex. In embodiments, the present disclosure includes a nucleic acid sequence of SEQ ID NOs: 21-24 hybridized to a region of human miR-379 transcript of SEQ ID NO: 26 (i.e., transcript sequence SEQ ID NO: 119) to form a complex. In embodiments, the present disclosure includes a nucleic acid sequence having 90-91%, 91-92%, 92-93%, 93-94%, 94-95%, 95-96%, 96-97%, 97-98%, or 98-99% sequence identity with a continuous 10 nucleobase sequence of SEQ ID NO: 1, 2, 3, 4, 5, 6, 7, 8, 9, 10, 11, 12, 13, 14, 15, 16, 17, 18, 19, or 20, or analogues thereof, hybridized to a region of human miR-379 transcript of SEQ ID NO: 26 (i.e., transcript sequence SEQ ID NO: 119) to form a complex.

In embodiments, the present disclosure includes a complex of a nucleic acid sequence having 90-91%, 91-92%, 92-93%, 93-94%, 94-95%, 95-96%, 96-97%, 97-98%, 98-99%, or 99-100% sequence identity with a continuous 10, 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or nucleobase LNA analogs at the 5'- and/or the 3'-ends of the nucleic acid sequence, hybridized to a RNA sequence 10 to 270 nucleobase downstream of the transcription start site of microRNA-379 transcript.

In embodiments, the present disclosure includes a complex of a nucleic acid sequence having 90-91%, 91-92%, 92-93%, 93-94%, 94-95%, 95-96%, 96-97%, 97-98%, 98-99%, or 99-100% sequence identity with a continuous 10, 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or nucleobase LNA analogs at the 5'- and/or the 3'-ends of the nucleic acid sequence, hybridized to a RNA sequence transcript at 10-20, 10-30, 20-40, 20-50, 40-60, 40-70, 60-80, 60-90, 80-100, 80-110, 100-120, 100-130, 120-140, 120-150, 140-160, 140-170, 160-180, 160-190, 180-200, 180-210, 200-220, 200-230, 220-240, 220-230, 240-260, or 240-270 nucleobases downstream of the transcription start site of microRNA-379.

Method of Treatment or Use

The present disclosure provides a method of treating diabetic nephropathy in a subject in need thereof, the method including administering to the subject an effective amount of a compound of the present disclosure. The present disclosure includes a method of treating diabetic nephropathy in a subject by administering to the subject about 0.001 mg/kg to about 100 mg/kg of a compound of the present disclosure. In embodiments, a compound of the present disclosure inhibits renal glomerular podocyte death, glomerular mesangial expansion, glomerular hypertrophy, glomerular extracellular matrix accumulation, thereby treating DN.

In embodiments, the method of treating diabetic nephropathy in a subject includes administering to the subject a compound or a pharmaceutical composition including a nucleic acid sequence having 90-91%, 91-92%, 92-93%, 93-94%, 94-95%, 95-96%, 96-97%, 97-98%, 98-99%, or 99-100% sequence identity with a continuous 10, 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, or analogues thereof.

In embodiments, the method of treating diabetic nephropathy in a subject includes administering to the subject a compound or a pharmaceutical composition including a nucleic acid sequence having a nucleobase analog. In embodiments, the nucleic acid sequence includes Locked Nucleic Acid (LNA), 2'-O-alkyl, 2' O-Methyl, 2'-deoxy-2'fluoro, 2'-deoxy, a universal base, 5-C-methyl, an inverted deoxy abasic residue incorporation, or any combination thereof. In embodiments, the nucleic acid sequence may include analogs with positive backbones; non-ionic backbones, modified sugars, and non-ribose backbones (e.g. phosphorodiamidate morpholino oligos).

In embodiments, the present disclosure includes a method of treating diabetic nephropathy by administering a compound to a subject in need of such treatment, where the compound inhibits expression of a long non-coding RNA (lncMGC) in the subject. The method of treating diabetic nephropathy is by administering a compound to a subject in need of such treatment, where the compound inhibits expression of a long non-coding RNA (lncMGC) in the subject, which includes microRNA-376a, microRNA-299, microRNA-376c, microRNA-410, microRNA-494, microRNA-380-5p, microRNA-369-3p, microRNA-300, microRNA-541, microRNA-329, microRNA-381, microRNA-411, microRNA-134, microRNA-379, microRNA-154, microRNA-382, microRNA-376b, microRNA-496, microRNA-409-5p, microRNA-543, microRNA-377, microRNA-380-3p, and/or microRNA-495.

In embodiments, the present disclosure includes a method of treating diabetic nephropathy by administering a compound to a subject, where the compound inhibits expression of a microRNA gene cluster. In embodiments, expression of the microRNA gene cluster that is inhibited for treating diabetic nephropathy is microRNA-379 gene cluster. In embodiments, the microRNA gene cluster expression of which is inhibited expresses microRNAs such as microRNA-376a, microRNA-299, microRNA-376c, microRNA-410, microRNA-494, microRNA-380-5p, microRNA-369-3p, microRNA-300, microRNA-541, microRNA-329, microRNA-381, microRNA-411, microRNA-134, microRNA-379, microRNA-154, microRNA-382, microRNA-376b, microRNA-496, microRNA-409-5p, microRNA-543, microRNA-377, microRNA-380-3p, and/or microRNA-495.

The sequence of the nucleic acid that inhibits the microRNA for treating diabetic nephropathy is complementary to the microRNA sequence, or complementary to a transcript that includes the targeted microRNA and binds downstream of the transcription start site.

Human microRNAs targeted for treating diabetic nephropathy are listed in Table 2.

TABLE 2

Human microRNAs

| Name | Sequence | SEQ ID NO: |
|---|---|---|
| microRNA-376 a | UGCACCUAAAAGGAGAUACUA | 83 |
| microRNA-299-3p | UAUGUGGGAUGGUAAACCGCUU | 84 |
| microRNA-376c | UGCACCUUAAAGGAGAUACAA | 85 |
| microRNA-410 | UGUCCGGUAGACACAAUAUAA | 86 |
| microRNA-494 | CUCCAAAGGGCACAUACAAAGU | 87 |
| microRNA-380-5p | AUGGUUGACCAUAGAACAUGCG | 88 |
| microRNA-369-3p | AAUAAUACAUGGUUGAUCUUU | 89 |
| microRNA-300 | UCUCUCUCAGACGGGAACAUAU | 90 |
| microRNA-541 | AAAGGAUUCUGCUGUCGGUCCCACU | 91 |
| microRNA-329 | UUUCUCCAAUUGGUCCACACAA | 92 |
| microRNA-381 | UGUCUCUCGAACGGGAACAUAU | 93 |
| microRNA-411 | GCAUGCGAUAUGCCAGAUGAU | 94 |

TABLE 2-continued

Human microRNAs

| Name | Sequence | SEQ ID NO: |
|---|---|---|
| microRNA-134 | GGGGAGACCAGUUGGUCAGUGU | 95 |
| microRNA-379 | GGAUGCAAGGUAUCAGAUGGU | 96 |
| microRNA-154 | UAGGUUAUCCGUGUUGCCUUCG | 97 |
| microRNA-382 | GAAGUUGUUCGUGGUGGAUUCG | 98 |
| microRNA-376b | UUGUACCUAAAAGGAGAUACUA | 99 |
| microRNA-496 | CUCUAACCGGUACAUUAUGAGU | 100 |
| microRNA-409-5p | AGGUUACCCGAGCAACUUUGCAU | 101 |
| microRNA-543 | UUCUUCACGUGGCGCUUACAAA | 102 |
| microRNA-377 | UGUUUUCAACGGAAACACACUA | 103 |
| microRNA-380-3p | UAUGUAAUAUGGUCCACAUCUU | 104 |
| microRNA-495 | UUCUUCACGUGGUACAAACAAA | 105 |

In embodiments, mouse microRNA targeted for inhibition are listed in Table 3.

TABLE 3

Mouse microRNAs:

| Name | Sequence | SEQ ID NO: |
|---|---|---|
| microRNA-299-3p | UAUGUGGGAUGGUAAACCGCUU | 106 |
| microRNA-376c | UGCACUUUAAAGGAGAUACAA | 107 |
| microRNA-410 | UGUCCGGUAGACACAAUAUAA | 108 |
| microRNA-494 | CUCCAAAGGGCACAUACAAAGU | 109 |
| microRNA-380-5p | AUGGUUGACCAUAGAACAUGCG | 110 |
| microRNA-369-3p | AAUAAUACAUGGUUGAUCUUU | 111 |
| microRNA-541 | AAGGGAUUCUGAUGUUGGUCACACU | 112 |
| microRNA-329 | UUUUUCCAAUCGACCCACACAA | 113 |
| microRNA-381 | UGUCUCUCGAACGGGAACAUAU | 114 |
| microRNA-411 | GCAUGCGAUAUGCCAGAUGAU | 115 |
| microRNA-134 | UGUUUUCAACGGAAACACACUA | 116 |
| microRNA-379 | GGAUGCAAGGUAUCAGAUGGU | 65 |
| microRNA-154 | UAGGUUAUCCGUGUUGCCUUCG | 66 |
| microRNA-382 | GAAGUUGUUCGUGGUGGAUUCG | 67 |
| microRNA-376b | UUCACCUACAAGGAGAUACUA | 68 |
| microRNA-496 | CUCUAACCGGUACAUUAUGAGU | 69 |
| microRNA-409-5p | AGGUUACCCGAGCAACUUUGCAU | 70 |
| microRNA-543 | UUCUUCACGUGGCGCUUACAAA | 71 |
| microRNA-377 | UGUUUUCAACGGAAACACACUA | 74 |
| microRNA-380-3p | UAUGUAGUAUGGUCCACAUCUU | 75 |

TABLE 3-continued

Mouse microRNAs:

| Name | Sequence | SEQ ID NO: |
|---|---|---|
| microRNA-495 | UUCUUCACGUGGUACAAACAAA | 76 |
| miR-3072-5p | AGGGACCCCGAGGGAGGGCAGG | 77 |
| miR-3072-3p | UGCCCCUCCAGGAAGCCUUCU | 78 |

In embodiments, the present disclosure includes a method of treating diabetic nephropathy by administering a compound of the present disclosure, which upregulates microRNA target genes and down-regulates expression of profibrotic genes. In embodiments, the compound of the present disclosure up-regulates and down-regulates in kidney mesangial cells.

In embodiments, the compound of the present disclosure up-regulates target genes, for example, Tnrc6, CUGBP2, CPEB4, Pumillio2, BHC80 EDEM3, and any combination(s) thereof. In embodiments, the compound of the present disclosure down-regulates profibrotic genes, for example, pro-fibrotic genes Col1α2, TGF-β1, Col1α4, Plasminogen activator inhibitor-1 (PAI-1), fibronectin, connective tissue growth factor (CTGF), and any combination(s) thereof. In embodiments, the compound of the present disclosure treats diabetic nephropathy at an early stage of the disease. In embodiments, the diabetic nephropathy is characterized as having glomerular lesions including glomerular basement membrane thickening, mild mesangial expansion, severe mesangial expansion, nodular sclerosis (Kimmelstiel-Wilson lesions), or advanced diabetic glomerulosclerosis.

Method of Inhibiting Expression of a Mammalian microRNA-379 Cluster

The present disclosure provides a method of inhibiting expression of a mammalian microRNA-379, the method includes hybridizing a compound of the present disclosure to an RNA sequence 10 to 270 nucleobases downstream of the transcription start site of a mammalian microRNA-379 transcript. In embodiments, the method of inhibiting expression of a mammalian microRNA-370 cluster includes contacting a cell or tissue with a nucleic acid sequence of SEQ ID NOs: 1-24. In embodiments, the method of inhibiting expression of a mammalian microRNA-370 cluster includes contacting a cell or tissue with a nucleic acid sequence having 90-91%, 91-92%, 92-93%, 93-94%, 94-95%, 95-96%, 96-97%, 97-98%, 98-99%, or 99-100% sequence identity with a continuous 10, 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or nucleobase LNA analogs at the 5'- and/or the 3'-ends of the nucleic acid sequence.

In embodiments, the method of inhibiting expression of a mammalian microRNA-370 cluster includes contacting a kidney mesangial cell with a nucleic acid sequence of SEQ ID NOs: 1-24. In embodiments, the method of inhibiting expression of a mammalian microRNA-370 cluster includes contacting a kidney mesangial cell with a nucleic acid sequence having 90-91%, 91-92%, 92-93%, 93-94%, 94-95%, 95-96%, 96-97%, 97-98%, 98-99%, or 99-100% sequence identity with a continuous 10, 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or nucleobase LNA analogs at the 5'- and/or the 3'-ends of the nucleic acid sequence.

Pharmaceutical Composition

The present disclosure provides a pharmaceutical composition including a compound of the present disclosure and a pharmaceutically acceptable diluent, carrier, salt, and/or adjuvant.

In embodiments, the pharmaceutical composition of the present disclosure includes a nucleic acid sequence of SEQ ID NOs: 1-24. In embodiments, the pharmaceutical composition of the present disclosure includes a nucleic acid sequence having 90-91%, 91-92%, 92-93%, 93-94%, 94-95%, 95-96%, 96-97%, 97-98%, 98-99%, or 99-100% sequence identity with a continuous 10, 11, 12, 13, 14, 15, 16, or 17 nucleobase sequence of SEQ ID NO: 1, 2, 3, 4, 5, 6, 7, 8, 9, 10, 11, 12, 13, 14, 15, 16, 17, 18, 19, 20, 21, 22, 23 or 24, with internal internucleotide phosphorothioate linkage between nucleobases and/or nucleobase LNA analogs at the 5'- and/or the 3'-ends of the nucleic acid sequence.

In embodiments, the present includes administering to an individual, a composition of a therapeutically effective amount of a compound including a nucleic acid sequence of SEQ ID NOs: 1-24, alone or in combination with a diabetic and/or diabetic nephropathic agent. The effective dose of the composition may be between about 0.001 mg/kg to about 100 mg/kg of compound. In embodiments, the compositions may have between about 0.1% to about 20% of the pharmaceutical composition. In embodiments, the compositions may include pharmaceutically acceptable diluent(s), excipient(s), and/or carrier(s).

The composition of a compound including a nucleic acid sequence of SEQ ID NOs: 1-24 may be administered with a suitable pharmaceutical carrier. The administration can be local or systemic, including oral, parenteral, intraperitoneal, intrathecal or topical application. The release profiles of such composition may be rapid release, immediate release, controlled release or sustained release. For example, the composition may comprise a sustained release matrix and a therapeutically effective amount. Alternatively, a composition of a compound including a nucleic acid sequence of SEQ ID NOs: 1-24 can be secreted by genetically modified cells that are implanted, either free or in a capsule, at the gut of a subject. In embodiments, a composition of a compound including a nucleic acid sequence of SEQ ID NOs: 1-24 may be administered to a subject via subcutaneous route. In embodiments, the composition may be administered as an oral nutritional supplement.

Oral compositions may include an inert diluent or an edible pharmaceutically acceptable carrier. They can be enclosed in gelatin capsules or compressed into tablets. For the purpose of oral administration, a composition of a compound including a nucleic acid sequence of SEQ ID NOs: 1-24 can be incorporated with excipients and used in the form of tablets, troches, or capsules. Oral compositions can also be prepared using a fluid carrier for use as a mouthwash, wherein the agent in the fluid carrier is applied orally and swished and expectorated or swallowed. Pharmaceutically compatible binding agents or adjuvant materials can be included as part of the composition. The tablets, pills, capsules, troches and the like can contain any of the following ingredients, or agents of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

In embodiments, a composition of a compound including a nucleic acid sequence of SEQ ID NOs: 1-24 in combination with another pharmaceutically active agent (small molecule or a large biological molecule) formulated for parenteral (including subcutaneous, intramuscular, and intravenous), inhalation, buccal, sublingual, nasal, rectal, topical, or oral administration for treating a viral infection, for inducing immune response, for treating neuroinflammation. The compositions may be conveniently presented in unit dosage form, and prepared by any of the methods well known to one skilled in the art.

In embodiments, the composition of the present disclosure may be formulated in dosage unit form for ease of administration and uniformity of dosage. Dosage unit form as used herein refers to physically discrete units suited as unitary dosages for the individual to be treated; each unit containing a predetermined quantity of agent calculated to produce the desired therapeutic effect in association with the required pharmaceutical carrier. The specification for the dosage unit forms are dictated by and directly dependent on the unique characteristics of the agent and the particular therapeutic effect to be achieved.

The following examples are provided as illustrations of various embodiments of the disclosure but are not meant to limit the disclosure in any manner.

EXAMPLES

Figure 2A:
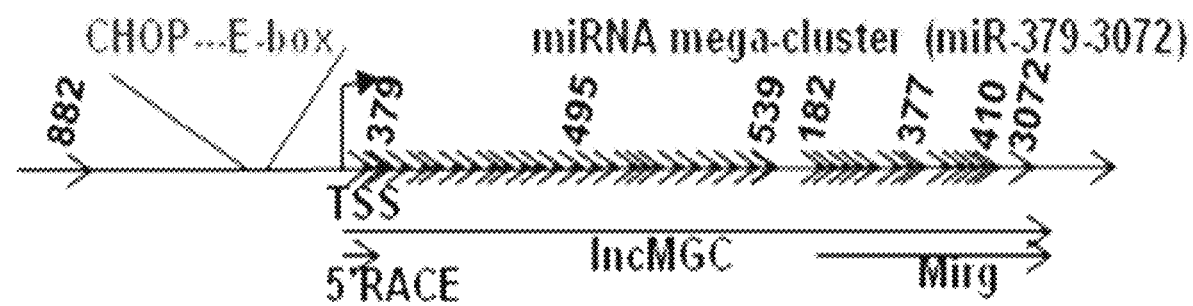
FIGS. 2A-2B are a diagram (2A) and a histogram (2B).
Figure 2B:
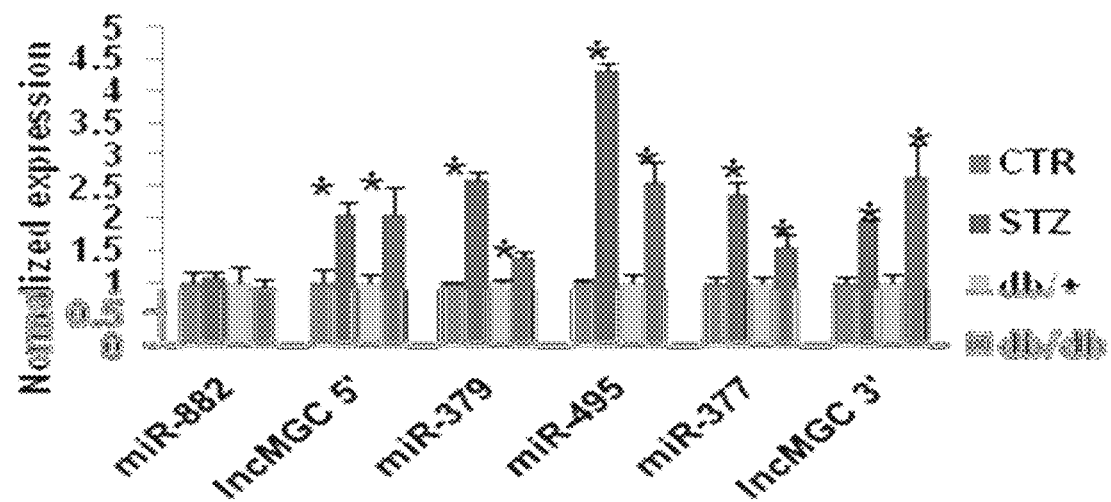

Example 1: Small RNA (miRNA)-Sequencing Revealed Mega Cluster of miRNAs was Up-Regulated Under Diabetic Conditions RNA obtained from the glomeruli of streptozotocin (STZ) diabetic and control mice was profiled by miRNA-sequence and the Illumina sequencing data analyzed. In the diabetic mice glomeruli, a significant increase in the expression of several miRNAs was found (e.g. miR-379, -495, -377) (FIG. 2B) that are among the mega cluster of miRNAs within mouse Chr12 (FIG. 2A). Genome organization showed that the miRNA mega cluster is hosted downstream of the lncRNA termed lnc-MGC, with another reported lncRNA, Mirg, present in this locus (FIG. 2A). Lnc-MGC expression (5' and 3') was also increased under these diabetic conditions (FIG. 2B), p<0.05. Furthermore, apart from the region upstream of lnc-MGC, no clear putative promoter was evident throughout the cluster, indicating that the miRNA cluster and lncRNA may be co-transcribed together as one unit, i.e., lnc-MGC may be induced under diabetic conditions and this up-regulates key miRNAs of the, cluster as one transcript, which encompasses a long ncRNA that functionally serves as host for the mega miRNA cluster.

Figure 3:
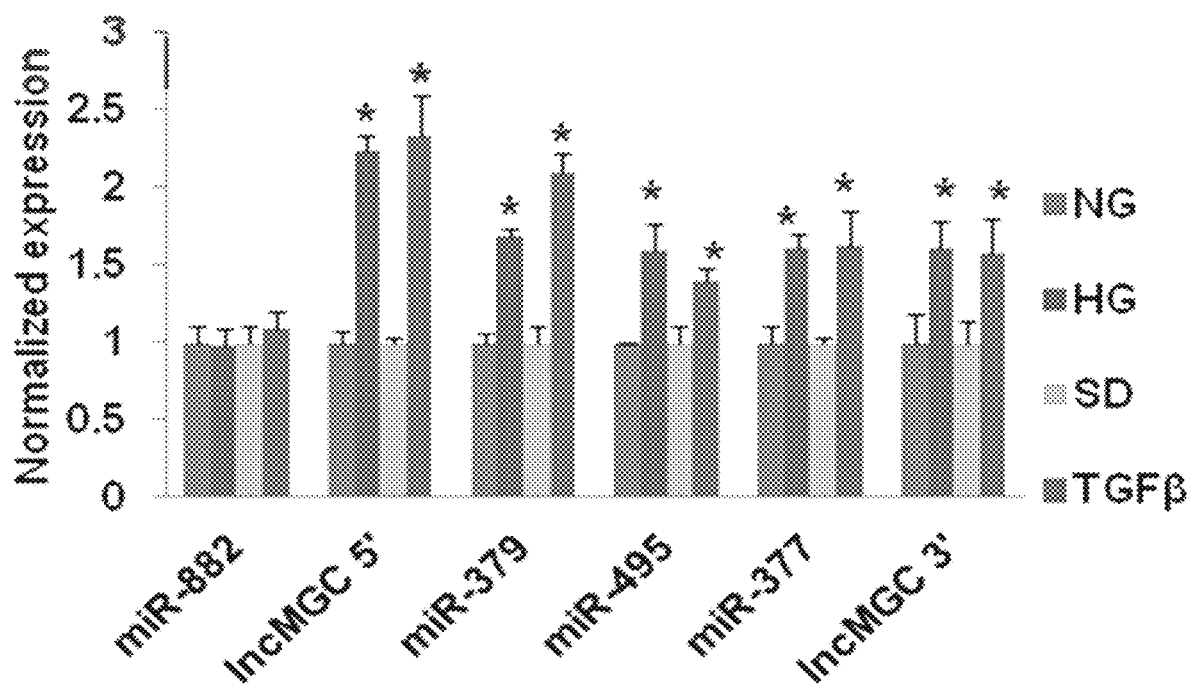
FIG. 3 is a bar graph showing key cluster miRNAs and the host lncRNA-MGC induced in MC treated with high glucose (HG) or transforming growth factor beta (TGFβ1).

Mouse MC (MMC) was treated with high glucose (HG, 25 mM), mannitol or TGF-β1 and several miRNAs within the cluster, (and lnc-MGC), was examined by amplifying these regions with specific PCR primers. TGF-β1 and HG significantly up-regulated the expression of miR-379 (the first miRNA in the cluster), miR-495 (in the middle) and miR-377 (downstream), as well as lnc-MGC (FIG. 3), further supporting the sequencing and in vivo data (*, p<0.05) (NG=normal glucose, SD=serum depletion control for TGF-β1). miR-882 outside the cluster was unaffected. These results indicated that an miRNA mega cluster and its host lncRNA are concomitantly up-regulated in the glomeruli and MCs under diabetic conditions.

Small RNA (sm-RNA) sequencing was performed as previously described. Scatter plot of miRNAs in kidney glomeruli from control (CTR) and diabetic mice (STZ) were generated. The expression of each detectable miRNA in the form of log scaled reads was plotted with x-axis for CTR and y-axis for STZ. Each dot represents one miRNA. All the miRNAs in the miR-379 cluster were presented in red. Among them, the upregulated miRNAs with fold change ≥2) were highlighted with bigger size dots and labeled with the corresponding miRNA names. miR-882 was plotted in blue as a negative control (outside of miR-379 cluster). The expression of each detectable miRNA within the miR-379 cluster in the two samples (CTR and STZ) were ordered by log 2 fold change from low to high, mean-centered and shown in the heatmap. Green represents lower than average expression in the 2 samples and red presents higher than average expression level. The expression of the detected miRNAs in this cluster was higher in STZ than CTR. The mouse miR-379 megacluster is located within the largest miRNA cluster currently identified in the genome. It maps within the DLK-DIO3 genomic region (mouse chr 12, human chr14), which is home to several miRNAs and lncRNAs. TSS, transcription start site. miR-882 is located far-upstream of miR-379 cluster and not covered by lnc-MGC. All the miRNAs detected by smRNA-seq with at least 5 scaled reads in at least one sample are ranked by log 2 fold change between STZ and CTR samples to generate ranked list and all the detectable miRNAs in cluster are considered as a gene set. Pre-ranked gene set analysis (GSEA) applied on the gene set using the ranked list of all the miRNAs revealed that miRNAs in the miR-379 cluster were significantly enriched within the miRNAs upregulated in the STZ diabetic mice, with normalized enrichment score of 1.56 (p=0.004).

Example 2: The Upstream Promoter of the Mega Cluster and lnc-MGC

Figure 4:
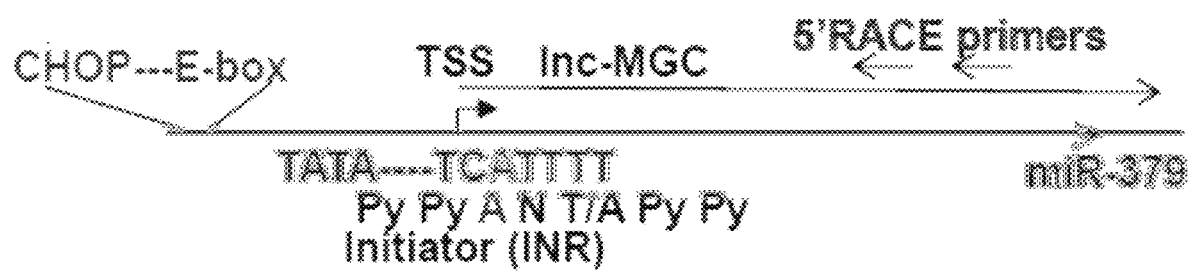
FIG. 4 is a diagram showing 5'RACE (Rapid Amplification of cDNA Ends) to clone the cluster and LncRNA-MGC (lncMGC) upstream region.

To identify a putative promoter that could drive the genomic region, 5' RACE experiments using primers from the miR-379 upstream region were carried out (FIG. 4). Results revealed that this region has promoter-like features with TATA box and an initiator (INR) site. The binding sites for the C/EBP homologous protein (CHOP), a transcription factor (TF) associated with the ER and stress response, and an overlapping E-box was identified. Data for this promoter location was further supported by results showing that this region upstream of miR379 (lncMGC 5' RACE (rapid amplification of cDNA ends)) is up-regulated in vivo in the glomeruli of diabetic mice (STZ-injected and db/db (the db/db mouse is a model of obesity, diabetes, and dyslipidemia wherein leptin receptor activity is deficient because the mice are homozygous for a point mutation in the gene for the leptin receptor)), and in vitro in MMCs treated with HG or TGF-β1 (*, p<0.05). These results identify the promoter of the lnc-RNA-MGC-miRNA cluster but also indicate that CHOP may be a key TF that regulates their coordinate expression.

Regulatory Role of CHOP: CHOP Protein Levels are Up-Regulated in the Glomeruli of Diabetic db/db and STZ-Injected Mice Experiments were performed to test whether CHOP regulates this genomic region. Western blots showed that CHOP protein levels were up-regulated in the glomeruli of diabetic db/db and STZ-injected mice, compared to the respective controls. CHOP was also induced in MMCs treated with TGF-β1, HG or osmotic control, mannitol, indicating that diabetic conditions and cellular stress can upregulate CHOP which in turn, increases transcription of lncRNA-MGC and the miRNA cluster.

CHOP Enrichment at the miR379 Promoter.

Chromatin immunoprecipitation (ChIP) assays were performed to evaluate CHOP enrichment at the miR379 promoter. A significant increase in CHOP occupancy at the CHOP binding site of the miR-379 promoter (arrows) in MMCs treated with HG or TGF-β1, versus control normal glucose (NG) or serum-depleted (SD) was observed.

CHOP-siRNA Effects

Efficacy of CHOP siRNA (relative to a negative control siRNA, NC) for down-regulating CHOP in MMCs was evaluated. CHOP siRNA significantly attenuated HG- and TGF-β1-induced expression of miR-379 and lnc-MGC. Mir-495 and -377 expression were also inhibited. In addition to these miRNAs, similar trends were observed for 29 other cluster miRNAs that were tested, i.e. these 29 were significantly up-regulated in diabetic mice glomeruli and in response to TGF-β1, and increases of the most of them were inhibited by CHOP siRNA in MC. Cumulatively, these results indicate that CHOP is a key transcriptional regulator of the miRNA cluster and related lncRNA-MGC.

Example 3: Targets of miRNA Cluster miRNA target prediction algorithms predicted that numerous miRNAs in the mega cluster collectively targeted similar genes. Therefore, the 3' UTRs of at least 25 genes were similarly targeted by 8-13 cluster miRNAs, with some genes having more than two miRNA target sites. Furthermore, it was found that these target genes had functions already related to DN, namely protein synthesis, ER stress, RNA binding proteins and protein translation (as determined by in silico GSEA (Gene Set Enrichment Analysis), IPA (Ingenuity Pathway Analysis), as well as Gene ontology analyses). This indicated that miRNAs in the mega cluster work in unison to alter the expression of groups of similar genes that can functionally modulate DN progression.

Identification and Validation of Putative Targets of the miR-379 Cluster.

Figure 5:
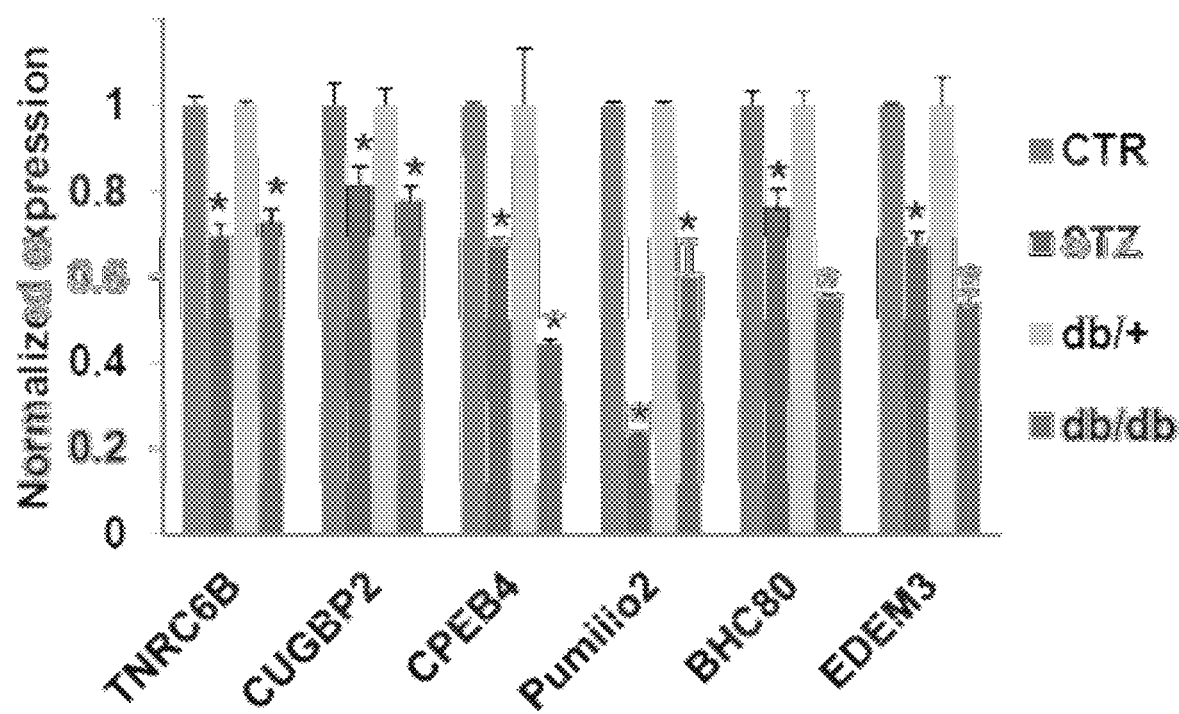
FIG. 5 is a bar graph showing that the expression of key indicated targets of miRNAs of the cluster is down-regulated in glomeruli of diabetic mice.
Figure 10:
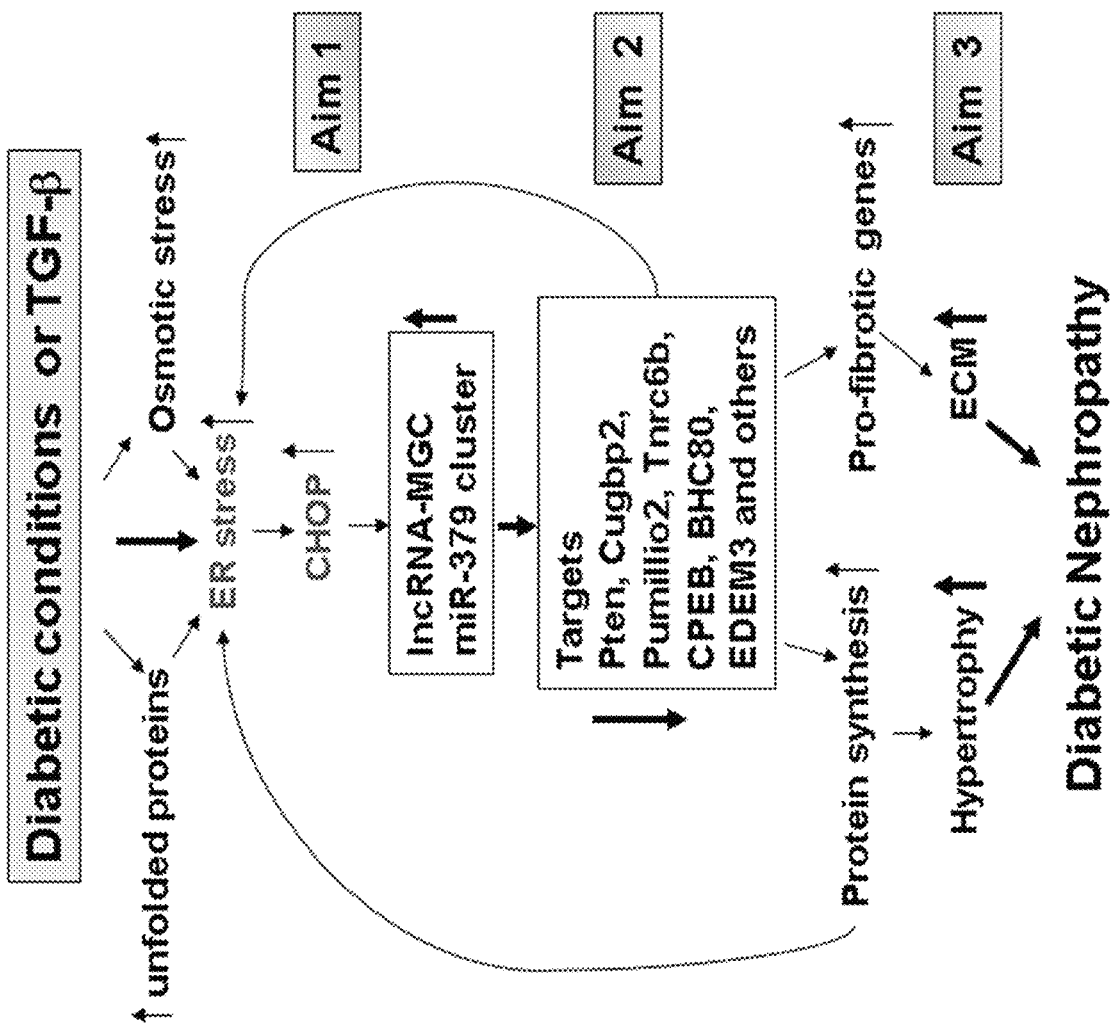
FIG. 10 is a diagram showing the scheme by which microRNA mega cluster and lnc-MGC can promote the progression of diabetic nephropathy (DN).

Several potential targets of key cluster miRNAs that have functions relevant to DN were identified. These included RNA binding proteins and translational regulators (CUGBP2), Pumilio2, Tnrc6b, CPEB4, HuR, TFs and cofactors (Arid2, BHC80), Nf1a/b), an ER stress modulator (EDEM3), and the cell growth gene phosphatase and tensin homolog (Pten). To validate, down-regulation under diabetic condition was evaluated in the target genes. It was found that TGF-β1 or HG can reduce the mRNA expression levels of Tnrc6, CUGBP2, CPEB4, Pumilio2, BHC80 and EDEM3 in MCs in vitro, and in the glomeruli of diabetic mice in vivo (db/db and STZ), relative to controls (FIG. 5; *p<0.05). These genes are known to regulate protein translation, protein synthesis, mRNA stability (e.g., CUGBP2) and miRNA processing (Tnrc6b). BHC80 interacts with histone deacetylases (HDACs) and the Ets TFs to promote chromatin condensation (86). Therefore, it is indicated that these targets mediate the downstream effects of the corresponding miRNAs in a cooperative and synergistic manner, to augment renal hypertrophy and fibrosis, and thereby enhance renal dysfunction in DN (FIG. 10).

Example 4: Effect of CHOP siRNA on Key miRNA Targets, MC Hypertrophy, Protein Synthesis and Fibrotic Genes CHOP siRNA treatment significantly prevented a key miRNA target (TNRC6) from being down-regulated by HG and TGF-β. Furthermore, in parallel, transfection of CHOP siRNA into MMCs also prevented increases in the TGF-β1 induced expression of key pro-fibrotic genes Col1α2, TGF-β1, Col1α4 and PAI-1 which are associated with DN. Consistently, CHOP siRNA also prevented TGF-β1 induced MC hypertrophy and protein content. These data indicate that inducing key mega cluster miRNAs can regulate MC genes and functions associated with DN pathogenesis through CHOP.

miRNAs and siRNAs

Oligonucleotide mimics and inhibitors of miRNAs, and siRNAs and corresponding control oligos were obtained from Integrated DNA technologies (IDT) or Thermo Fisher Scientific Inc. (Waltham, Mass.), as described. Wild-type (WT) MMCs (from WT C57BL/6 mice), MMC transfected with CHOP siRNA, and MMCs from CHOP-KO mice were treated with HG, mannitol and TGF-β1 as described. Briefly, cells (~$10^6$/transfection) were transfected with siRNA or miRNA oligonucleotides using an Amaxa Nucleofector (Lonza, Basel, Switzerland) according to the manufacturer's protocols as described previously. siRNAs (double-stranded oligos of three pairs of sense (S) and antisense (AS) synthesized oligos, S1
[SEQ ID NO: 59]
rCrArUrCrUrGrCrUrUrCrCrCrArCrUrGrCrCrArArArUrCAG and AS1
[SEQ ID NO: 60]
rCrUrGrArUrUrUrGrGrCrArGrUrGrGrGrArArGrCrArGrArUr
GrUrG;

S2
[SEQ ID NO: 61]
rUrCrArGrCrArCrCrGrUrGrCrArArCrCrArUrUrCrArArGGA and

AS2
[SEQ ID NO: 62]
rUrCrCrUrUrGrArArUrGrGrUrUrGrCrArCrGrGrUrGrCrUrGr
ArArA;

S3
[SEQ ID NO: 63]
rCrUrUrCrArUrCrUrGrGrUrArArUrGrUrArCrUrArCrCrUGA and

AS3
[SEQ ID NO: 64]
rUrCrArGrGrUrArGrUrArCrArUrUrArCrCrArGrArUrGrArAr
GrGrC;

(r, ribose) against mouse upstream region of miR-379 were obtained from IDT.

Non-targeting siRNA controls were obtained from Thermo Fisher Scientific Inc. MMC were trypsinized and resuspended in Basic Nucleofection Solution at $1\times10^7$/ml. Subsequently, 100 μl of cell suspension ($1\times10^6$ cells) was mixed with miRNA mimic, hairpin inhibitor oligonucleotides, or ON-TARGET plus siRNA or negative controls (Thermo Fischer Scientific Inc., Waltham, Mass.). Transfected cells were harvested for RNA and protein extraction. RNA was extracted from the cells and the expression of lncRNA-MGC, and all 40 miRNAs within the cluster were systematically examined using primers designed for each of the mature miRNAs. MMCs were transfected with oligonucleotide mimics, siRNAs of candidate miRNAs or negative control (NC) oligos to determine if manipulating their levels can influence TGF-β1 and HG responses. At 48-72 hr post-transfection, the expression of miRNA target genes, fibrosis and hypertrophy related genes, and proteins induced by TGF-β1/HG were determined by RT-qPCR and Western blotting using our published methods.

EDEM3 as a Direct Target of miR-379

Figure 6:
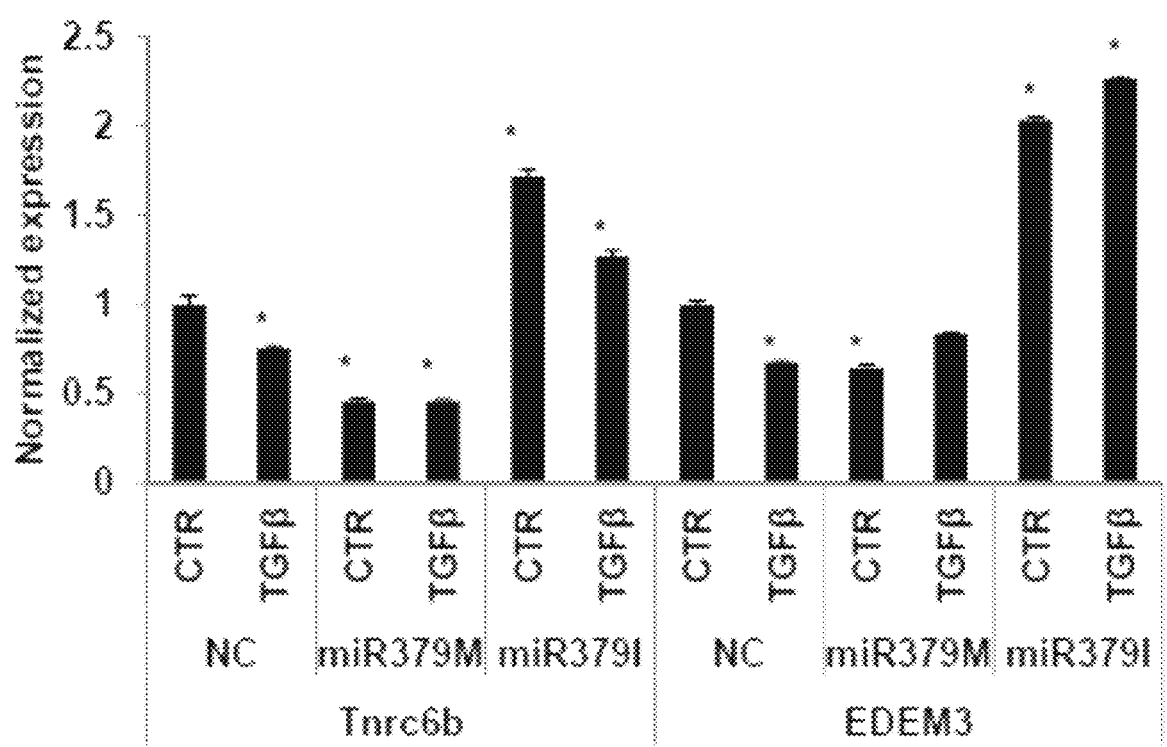
FIG. 6 is a bar graph showing that Tnrc6b and ER (endoplasmic reticulum) degredation-enhancing alpha-mannosidase-like 3 (EDEM) expression levels are decreased by miR-379 mimic (M) and increased by miR-379 inhibitor (I) oligos in MMCs.

Oligo mimics of miR-379 directly decreased the mRNA levels of its predicted targets Tnrc6b and EDEM3 in MMCs, whereas miR-379 inhibitor oligos (miR-379I) enhanced their mRNA levels in MMCs (FIG. 6). Protein levels of EDEM3 were also decreased in MMCs treated with TGF-β1 or transfected with miR-379 mimic, indicating that direct effects of a key cluster miRNA (miR-379) on MC gene expression.

Whether EDEM3 is a direct target of miR-379 was tested. 3'UTR of mouse EDEM3 gene was cloned into psiCheck2 vector and co-transfected to MMC with miR-379 mimic. miR-379 inhibited luciferase activity of this reporter, which suggested EDEM3 is a direct target of miR-379. A potential target site of miR-200b/c was found in the 3'UTR of EDEM3. miR-200b inhibited the reporter activity. Because miR-200b/c are also known to be upregulated in glomeruli from diabetic mouse and MMC treated with TGF-β1, miR200 family and miR-379 cluster may collaborate to inhibit EDEM3 expression. Because miR-379 and miR-200b had no effect on the reporter with partial deletion of region which includes miR-379 and miR-200b/c sites from 3'UTR of EDEM3, those sites are real targets of miR-379 and miR-200b. Those results also suggest that miR-379 cluster and miR-200b upregulated in diabetic conditions induces DN through hypertrophy and fibrosis mediated by EDEM3 (ER stress).

Figure 15A:
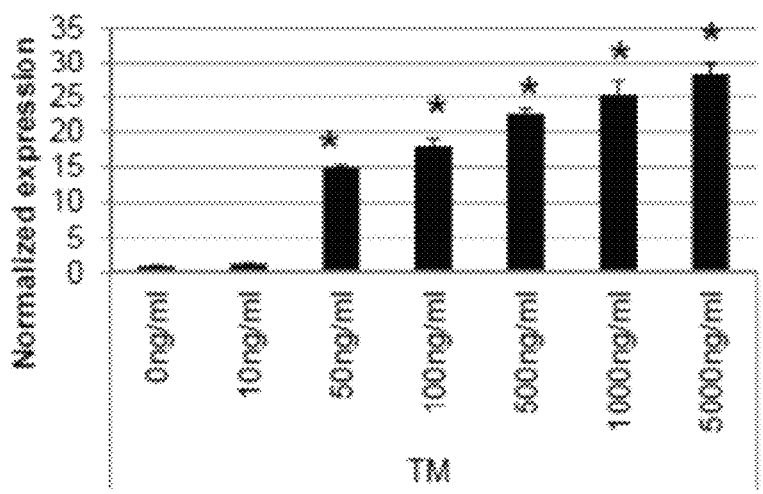
FIGS. 15A-15W are bar graphs of normalized RNA expression.
Figure 15B:
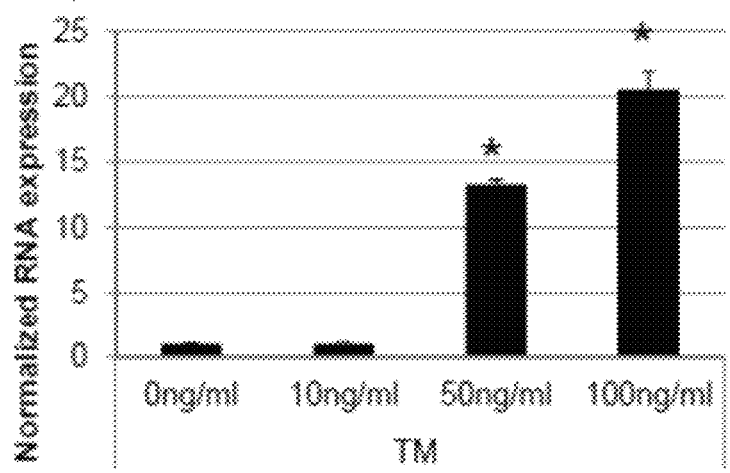
FIGS. 15C, 15K, and 15O depict western blots. MMC was treated with Tunicamycin™, a known ER stress inducer, and the expression of miR-379 cluster was tested.
Figure 15C:
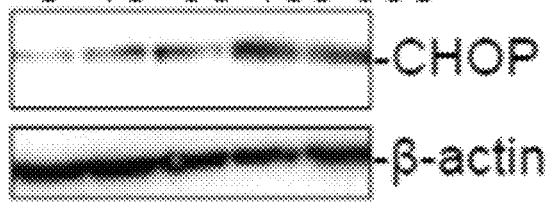
Figure 15D:
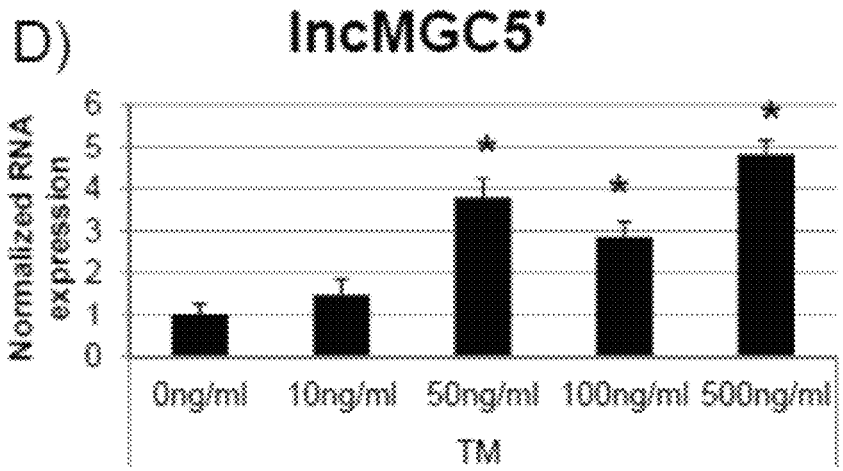
Figure 15E:
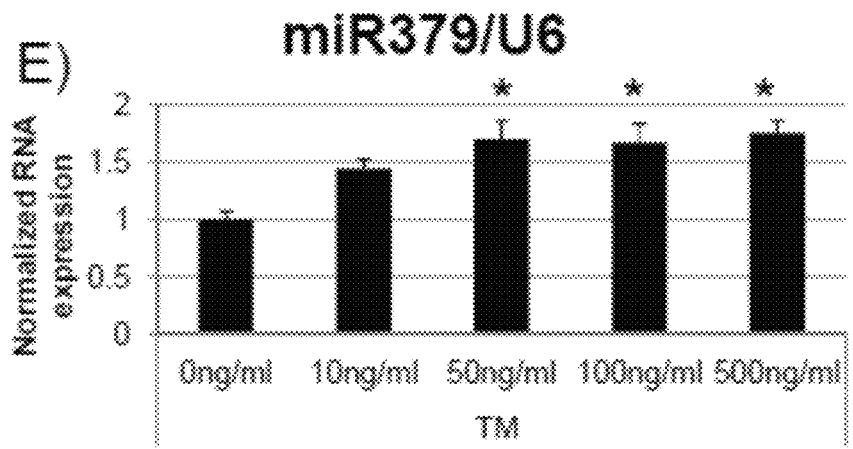
Figure 15F:
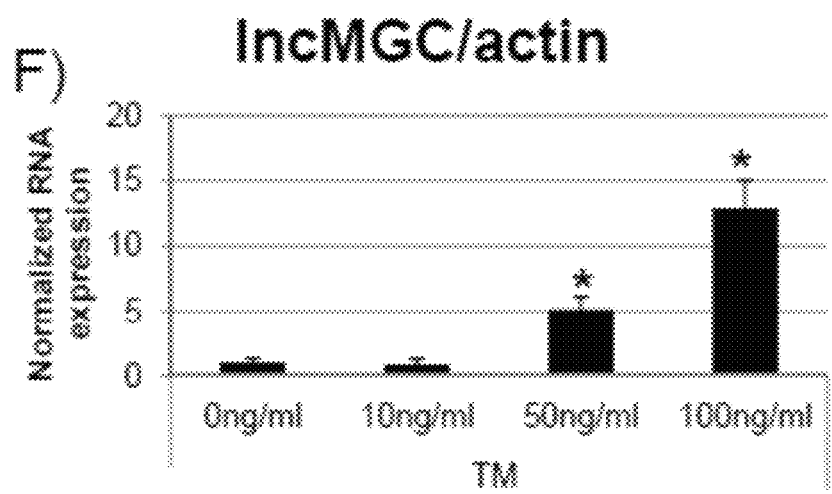
Figure 15G:
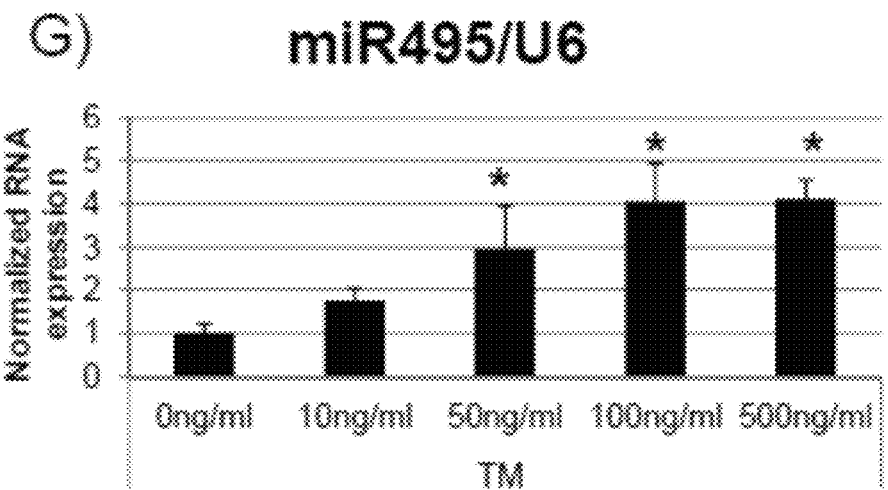
Figure 15H:
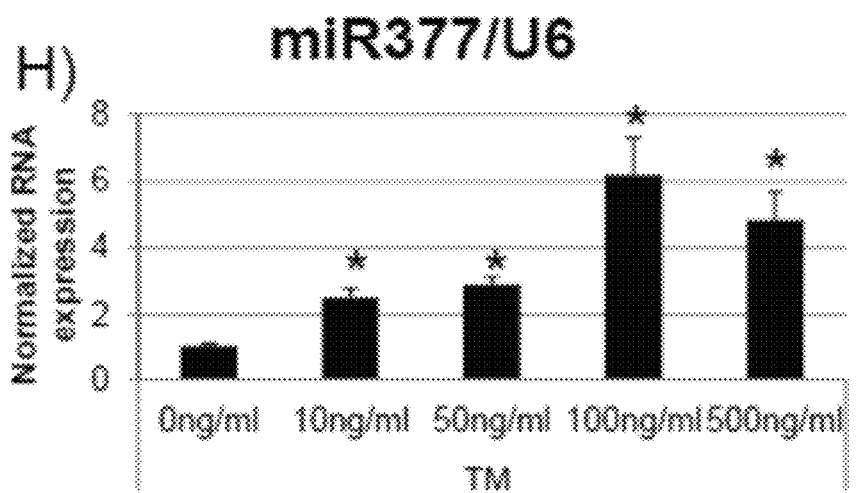
Figure 15I:
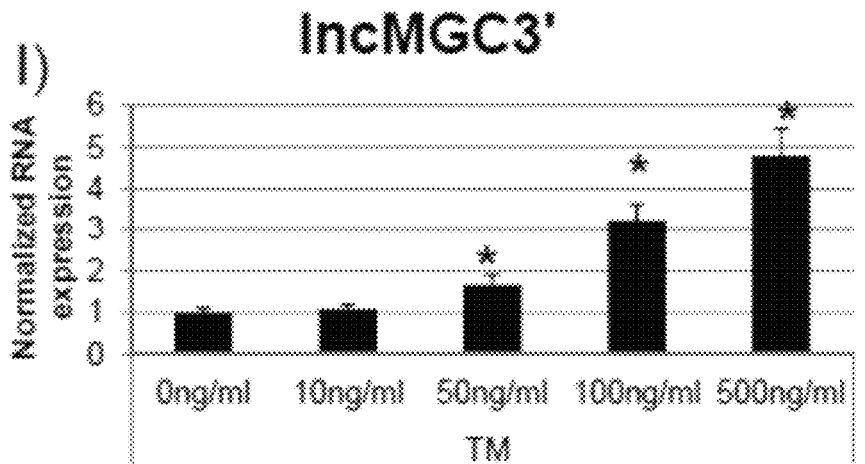
Figure 15J:
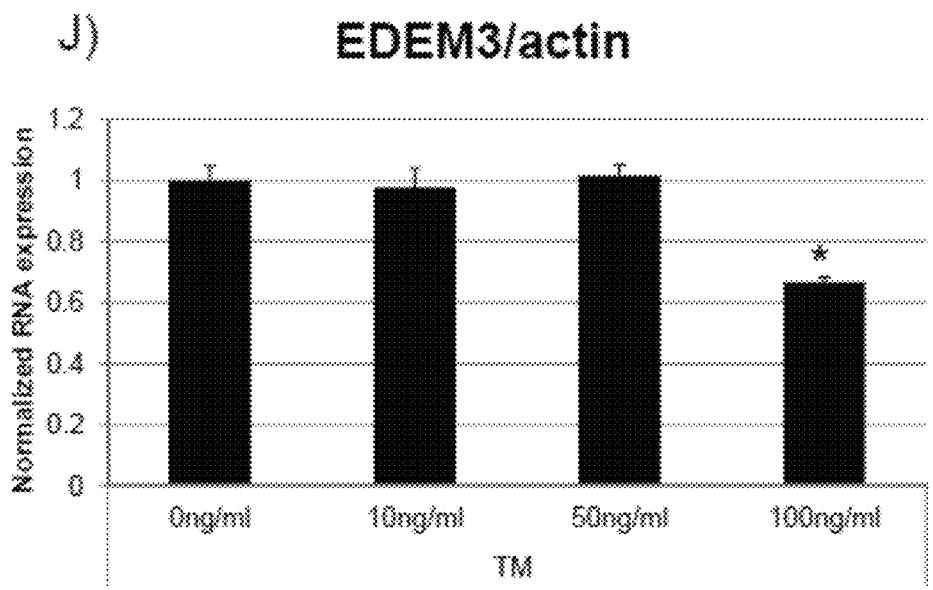

To confirm if ER stress is involved in the upregulation of miR-379 cluster, MMC was treated with Tunicamycin™, a known ER stress inducer, and the expression of miR-379 cluster was tested. Initially, to test what dose of TM is best, the expression of HSPA5 (heat shock 70 kDa protein 5), also known as GRP78 (glucose-regulated protein, 78 kDa), in MMC after treatment of TM (FIG. 15A). 50 ng/ml was the minimum and significant dose to induce the expression of HSPA5 and similar induction of CHOP was observed (FIGS. 15A-15C).

Figure 15K:
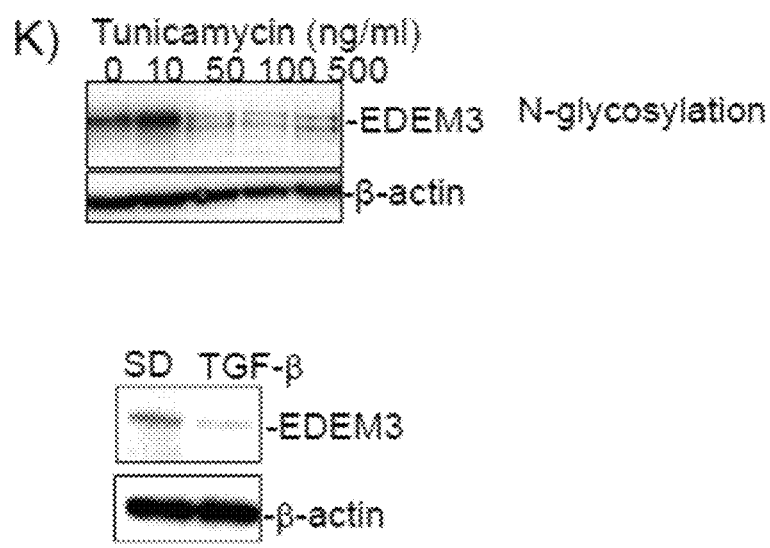
Figure 15L:
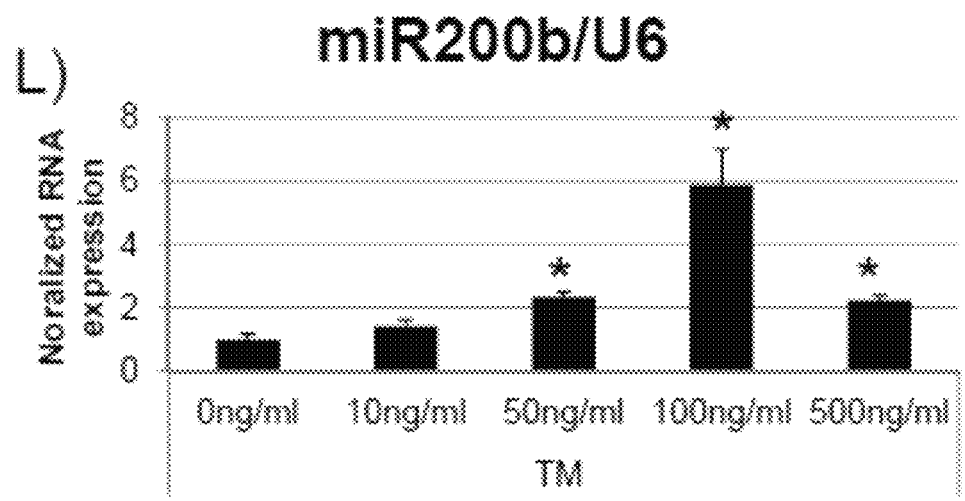
Figure 15M:
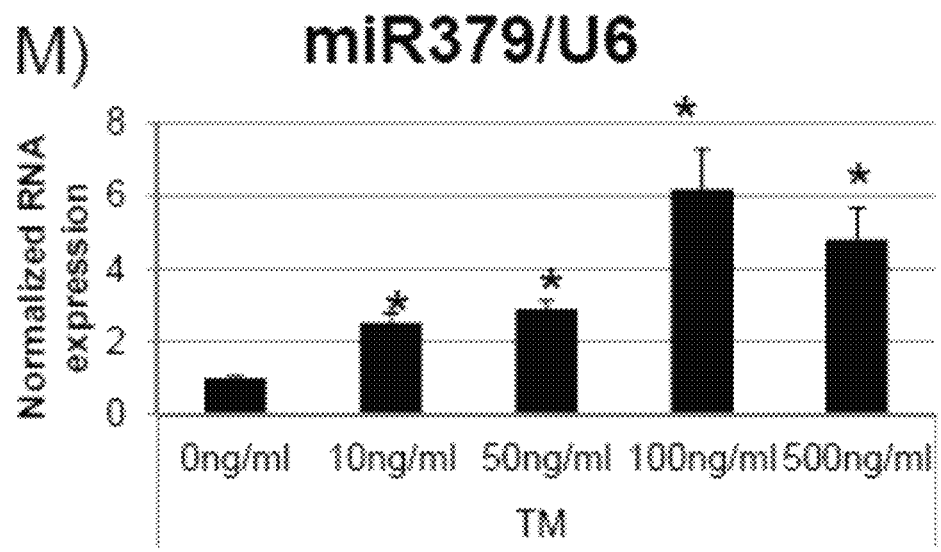
Figure 15N:
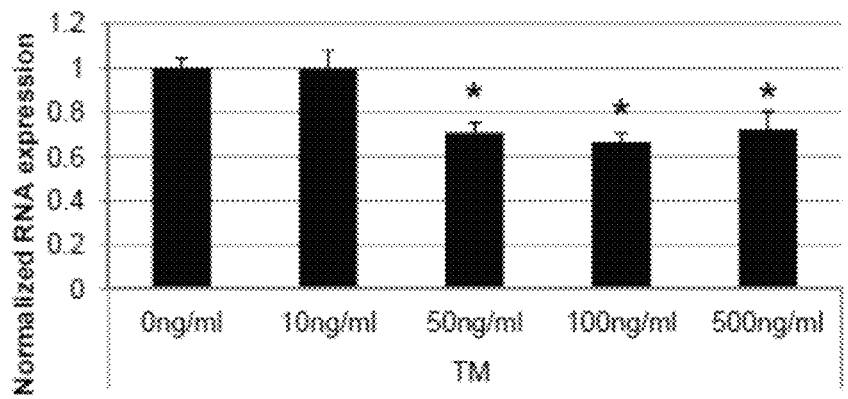
Figure 15O:
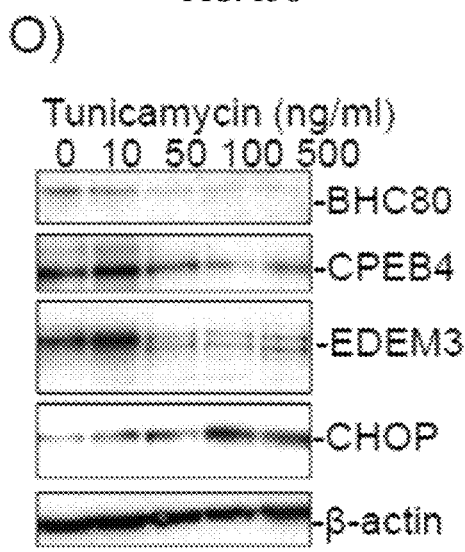
Figure 15P:
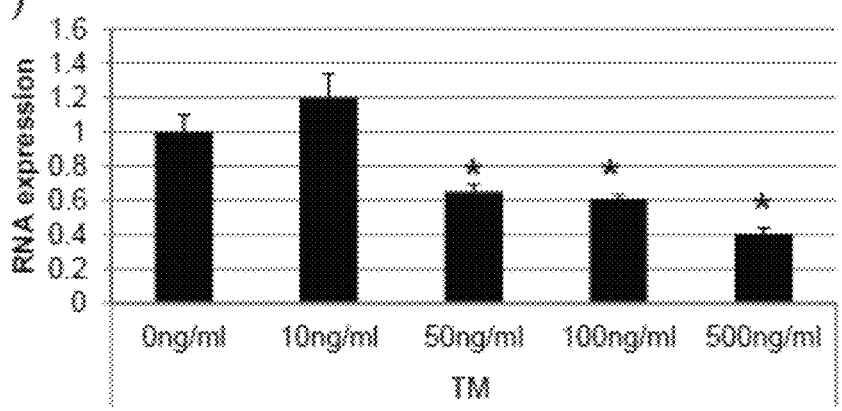
Figure 15Q:
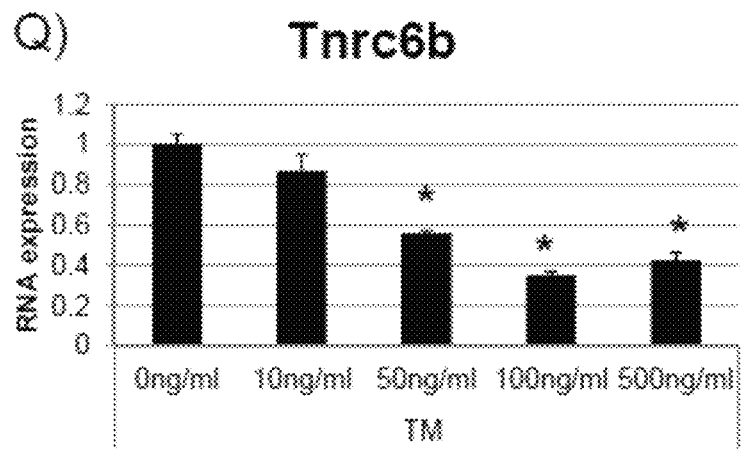
Figure 15R:
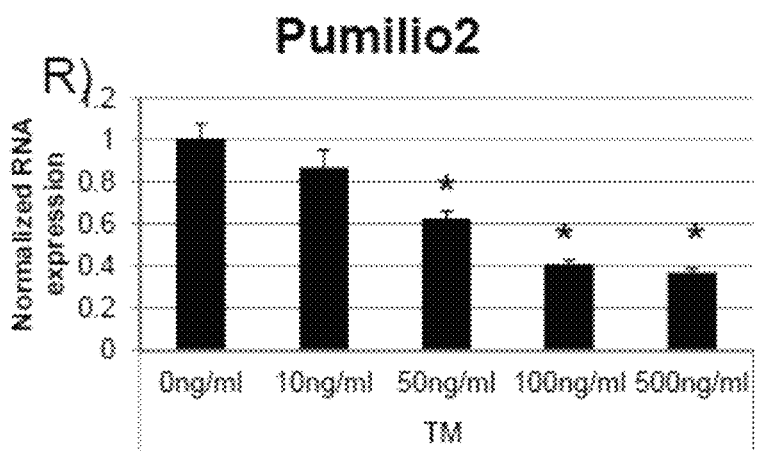
Figure 15S:
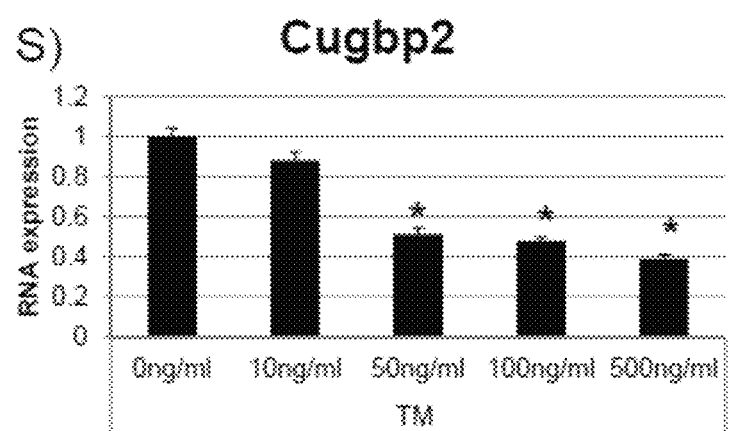
Figure 15T:
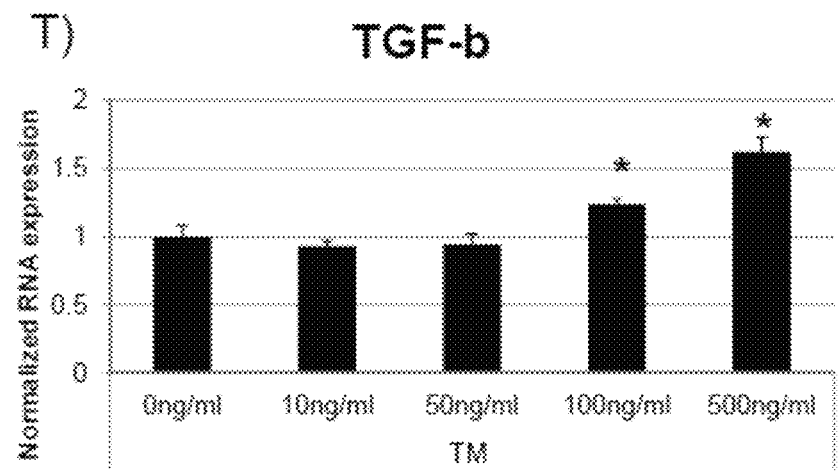
Figure 15U:
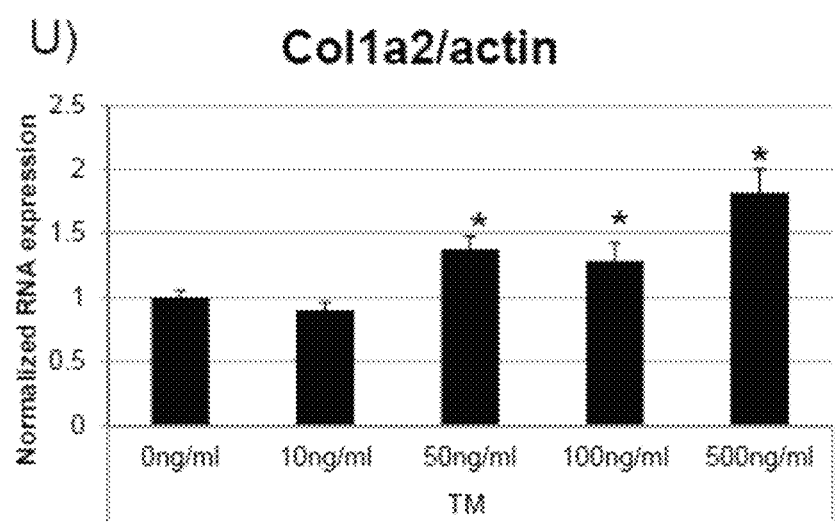
Figure 15V:
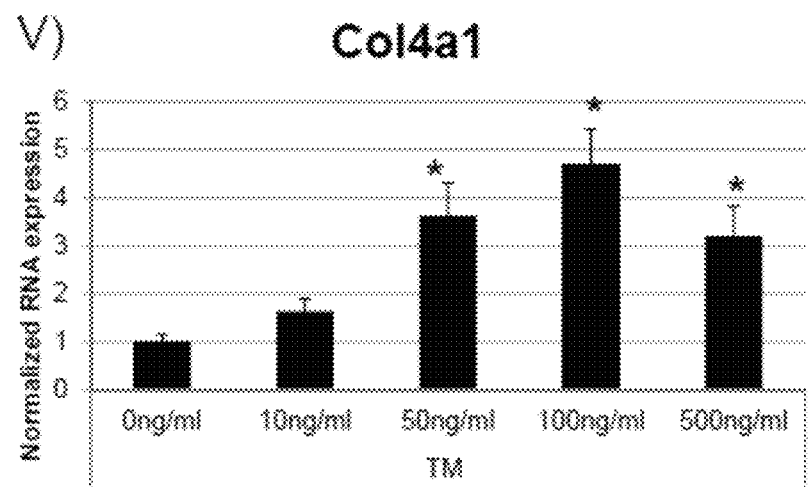
Figure 15W:
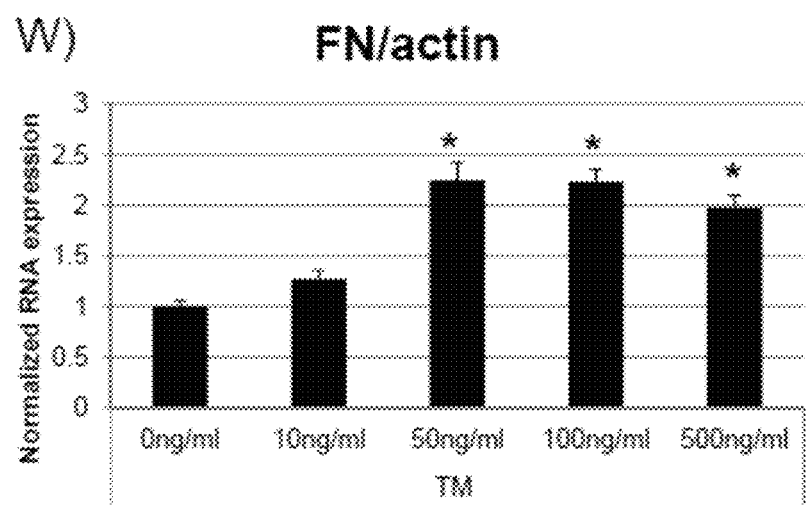

The expression of lncMGC and miRNAs in the cluster was increased by the TM (~50 ng/ml) (FIGS. 15D-15I), suggesting that TM (ER stress) induces this cluster expression in MMC. Targets of miR-379 cluster including EDEM3, a target of miR-379, were decreased by TM as expected (FIGS. 15J-15R). Faster migrating isoform of EDEM3 protein was detected in TM-treated cells by western blot while no such isoform was detected in MMC treated with TGF-β (FIG. 15K). TM is an inhibitor of N-glycosylation and faster-migrating form is an un-glycosylated form of EDEM3 which loses the activity to protect the cells from ER stress (FIG. 15K). TGF-β treatment decreased the expression of EDEM3 through induction of miR-379 and miR-200b (FIG. 15K). Thus, there are two independent regulations of EDEM3, loss of N-glycosylation and decrease of expression through miR-379 (miR-200b) induction by TM treatment (FIGS. 15K-15M). Other potential targets were down-regulated by TM (FIGS. 15N-15S). Pro-fibrotic genes, such as Col1α2, Col4α1, FN and TGF-β1 were also upregulated by TM treatment in MMC (FIGS. 15T-15W). These results suggest that TM (ER stress) induces miR-379 cluster expression and enhances ER stress and DN phenotypes (hypertrophy and fibrosis) by inhibiting the miR-379 cluster targets.

Approach to Interrupt lnc-MGC Expression

Figure 7:
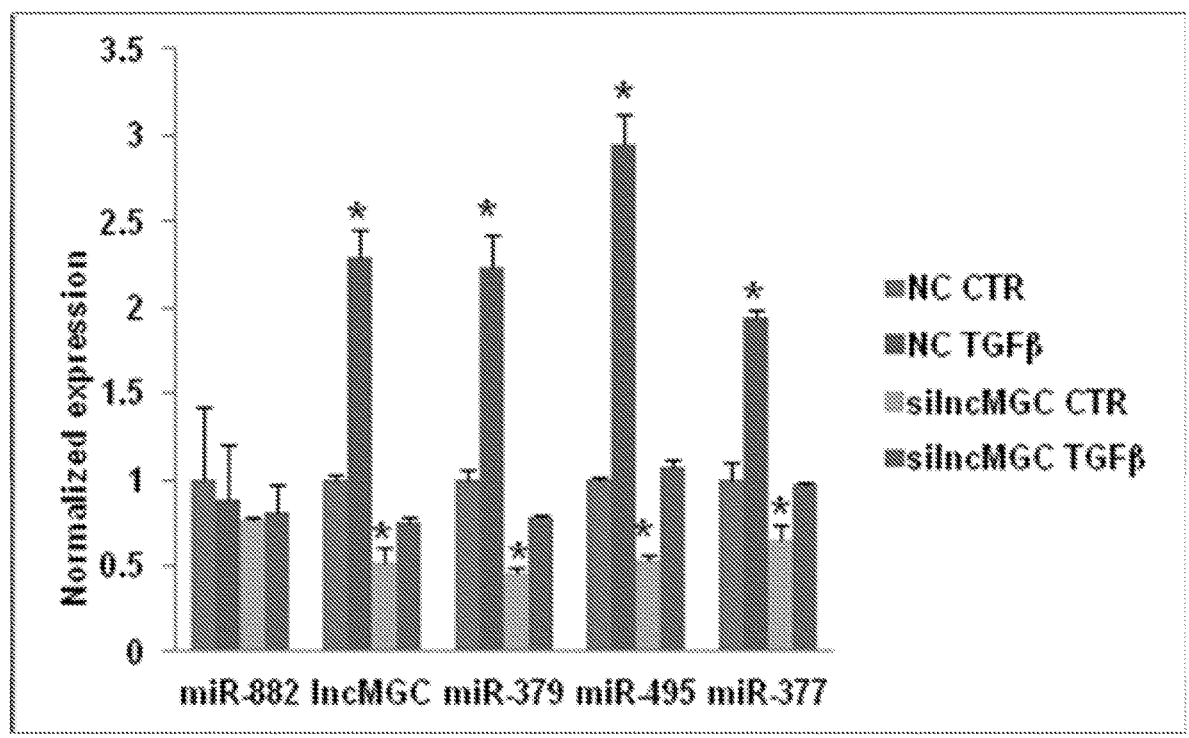
FIG. 7 is a bar graph showing that the expression levels of lnc-MGC and key cluster miRNAs are reduced in MMC transfected with an siRNA mixture targeting the lncMGC (silnc-MGC).

To inhibit the expression of lnc-MGC, a mixture of siRNAs to target lnc-MGC, which are located upstream of miR-379 was designed. Notably, transfecting this silnc-MGC into MMCs decreased both basal and TGF-β-induced expression not only of lncRNA-MGC, but also of the key cluster miRNAs 379, -495 and -377, without affecting miR-882, located outside the cluster (FIG. 7 p<0.05). This indicated that silnc-MGC RNAs down-regulate lnc-MGC, and thereby down-regulate the component cluster miRNAs and their functions.

Genome-Wide miRNA Target Identification

MCs were serum starved and tested with or without TGF-β1 for 24 hours. Cells were then UV crosslinked, sonicated and immunoprecipitated using an Ago2 antibody. Ago-associated RNA was purified then sequenced for RNA and miRNA on the Illumina Hiseq platform. The levels of 3' UTR RNAs of the Col1α1 gene, which were enriched in control Ago2-IP samples (CTR), were decreased by TGF-β1. The results indicate that, under CTR conditions, Ago2 miRNA complexes bind to the 3' UTR of Col1α1 RNAs. This is attenuated by TGF-β, which decreases specific miRNAs such as miR-29 to up-regulate Col1α1. These data suggest the feasibility of CLIP-seq experiments.

Example 5: Inhibition of lncMGC by Gapmers In Vivo

Figure 16A:
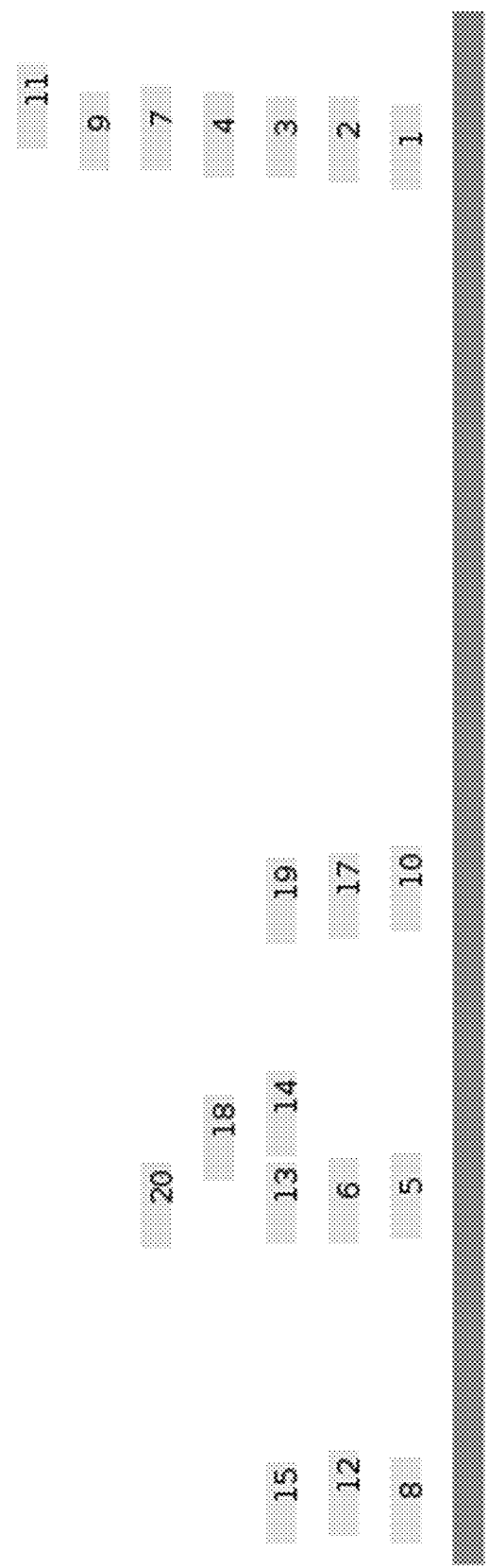
FIGS. 16A-16B depict schematics of representative Gapmer designs. The basic design of the Gapmers is three LNAs at both 5' and 3' ends of oligonucleotides and backbone is phosphorothioated. Sequence legend (FIG. 16B, in order of appearance): SEQ ID NOS: 52-54.
Figure 16B:
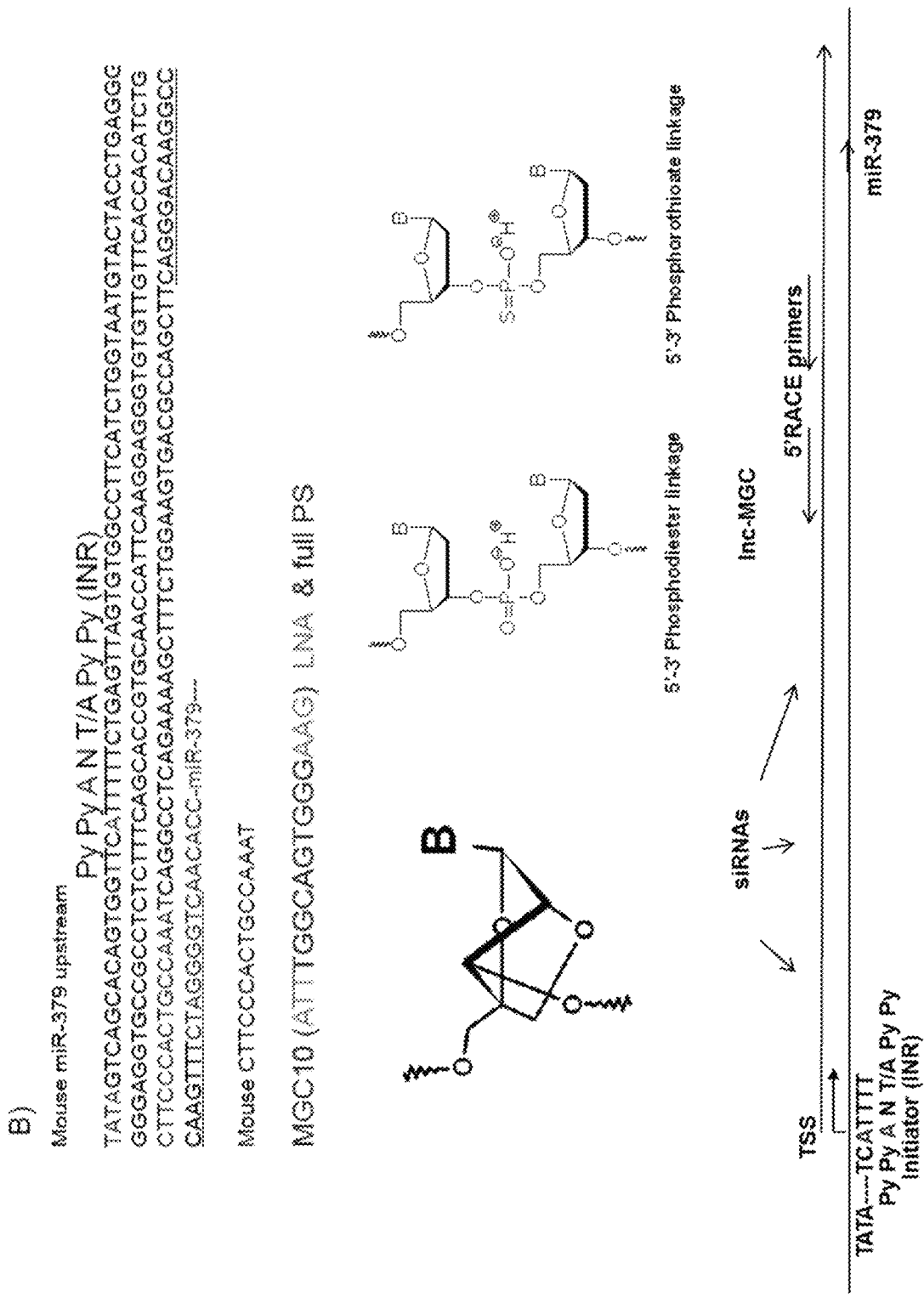
Figure 16G:
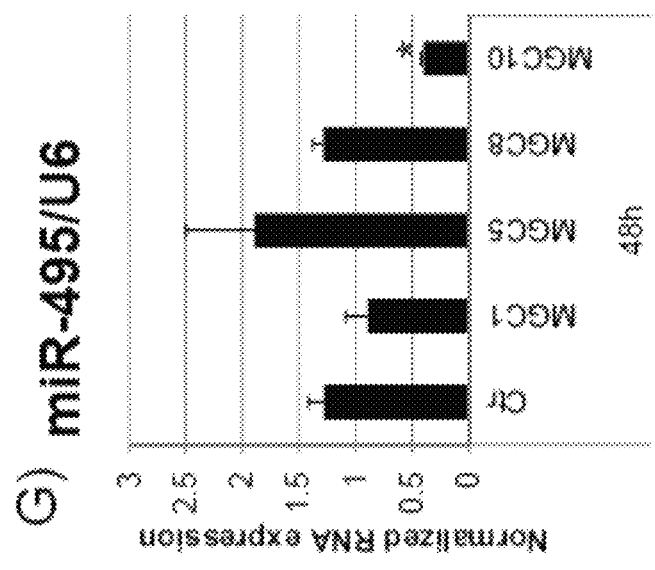
Figure 16H:
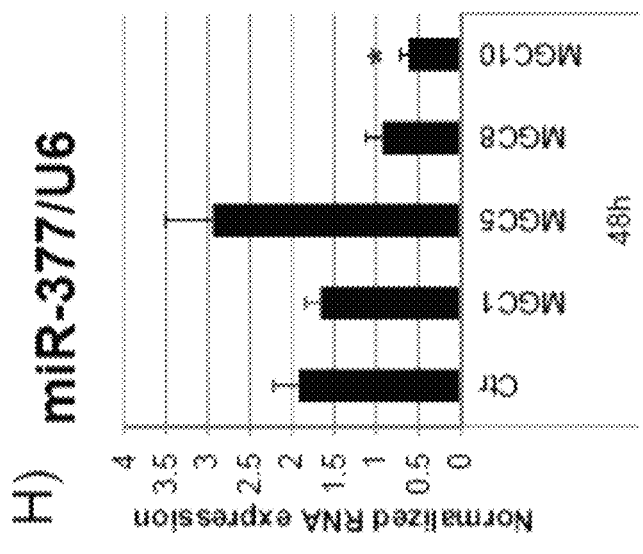
Figure 16I:
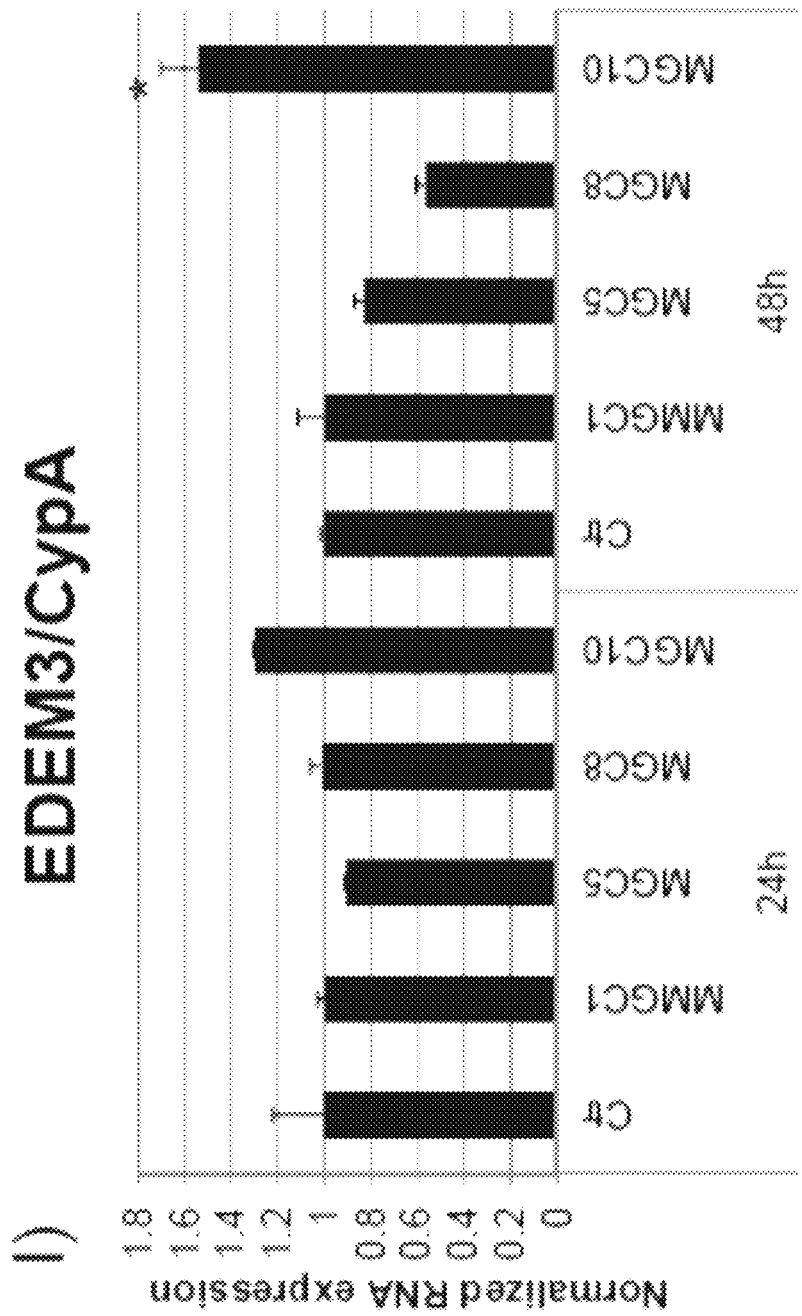
Figure 16J:
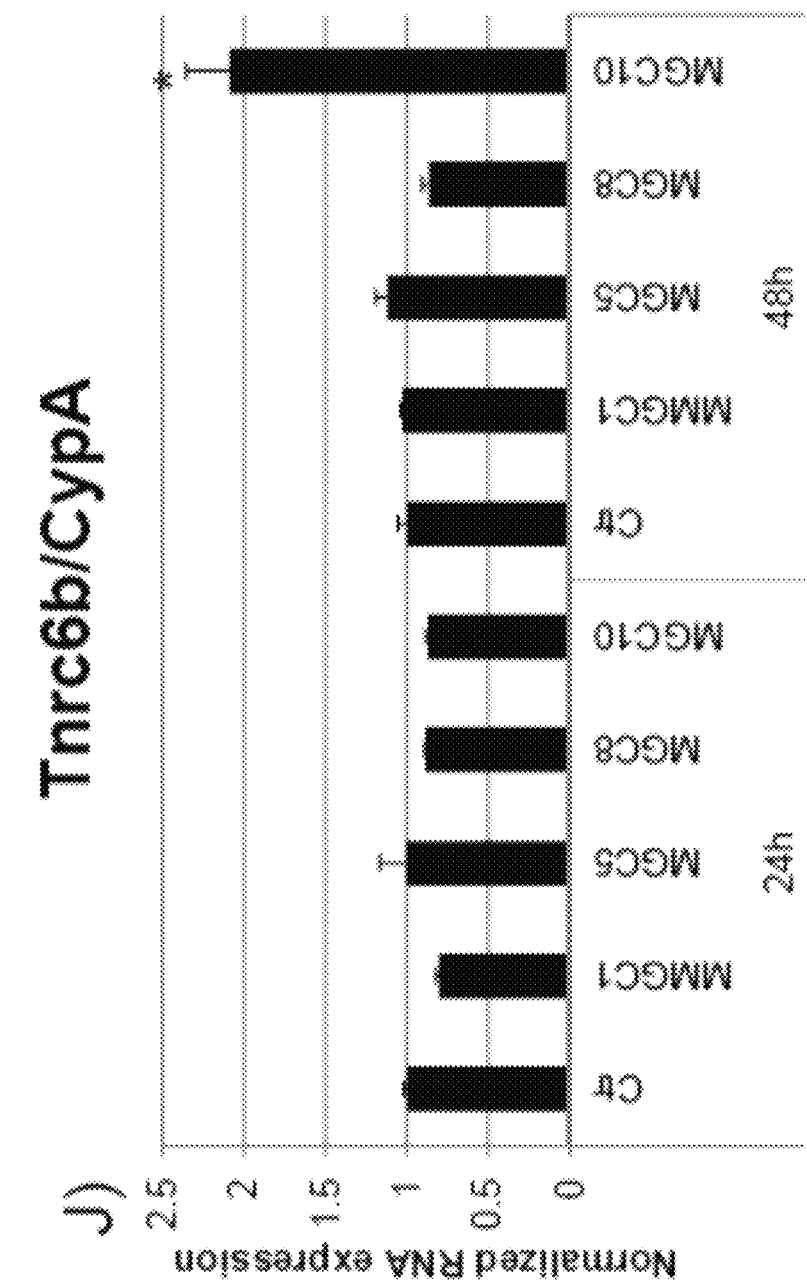
Figure 16K:
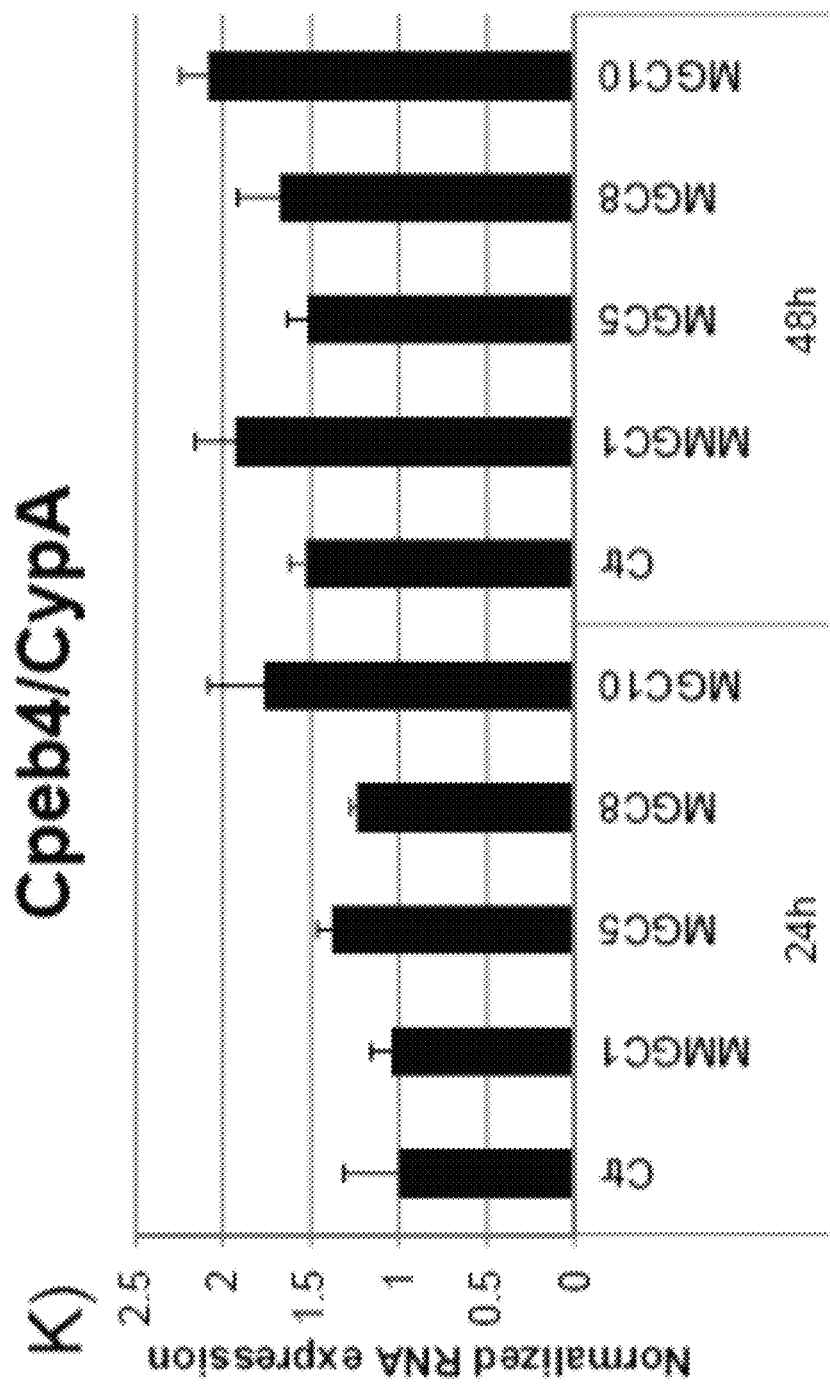
Figure 16L:
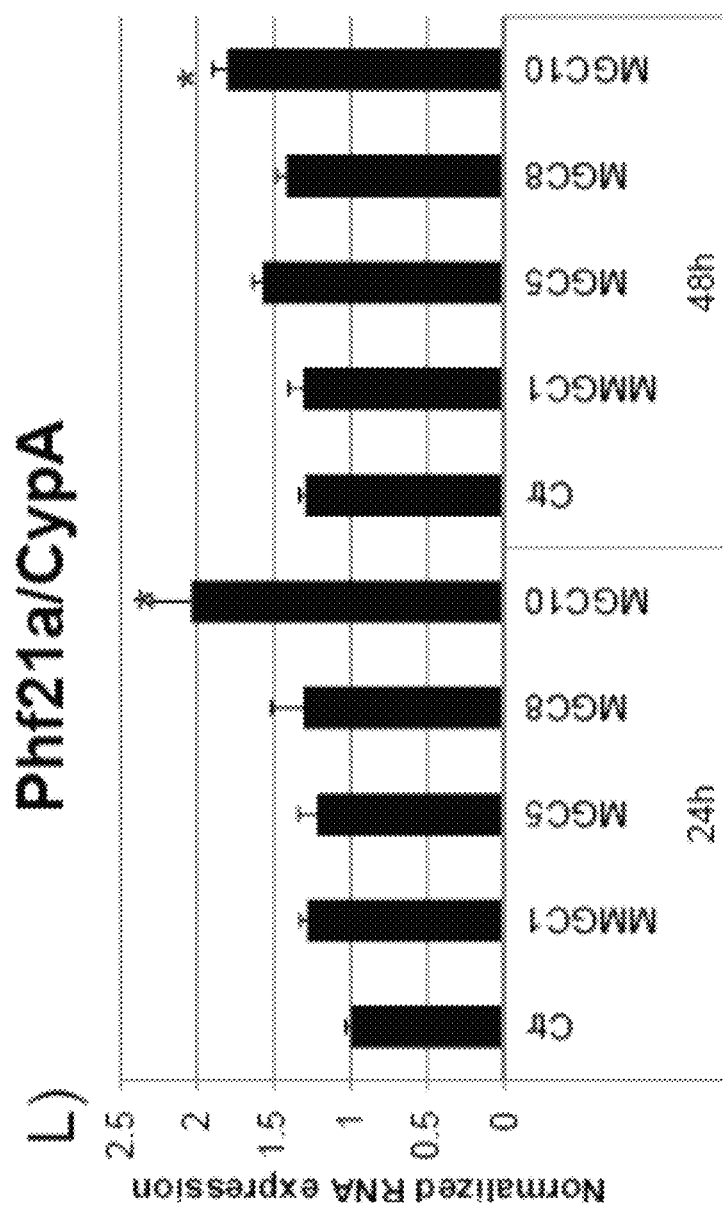
Figure 17A:
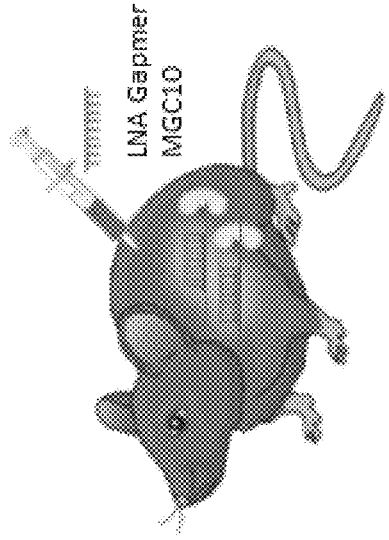
FIGS. 17A-17F demonstrates that MGC10 inhibits miR-379 cluster miRNAs in the mouse kidney in vivo.
Figure 17B:
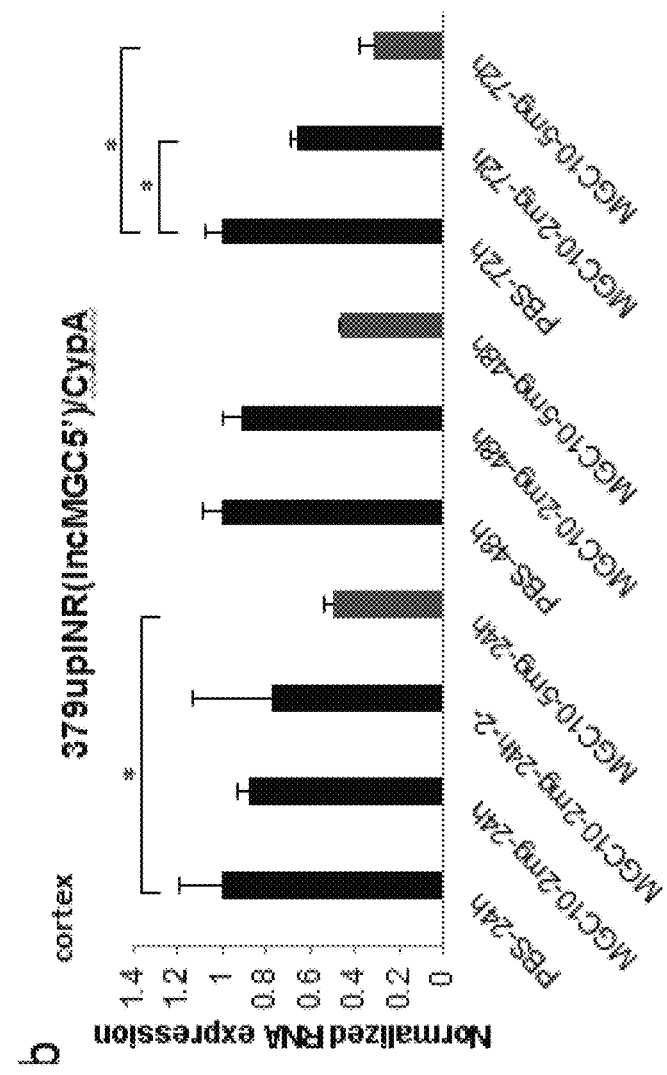
Figure 17C:
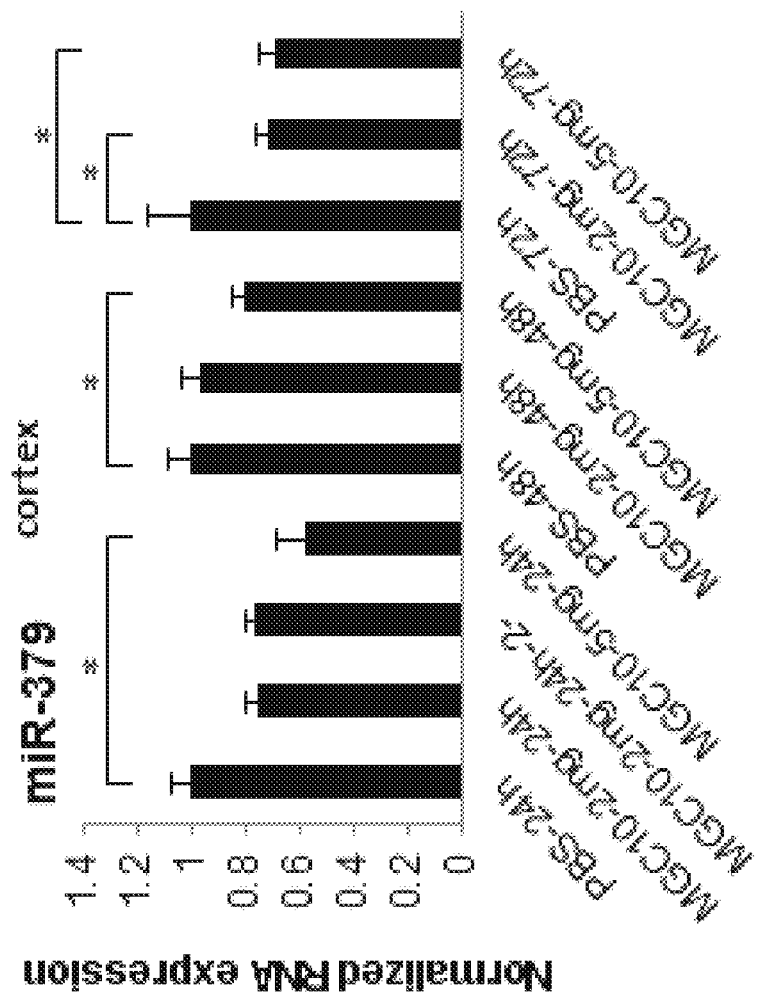
Figure 17D:
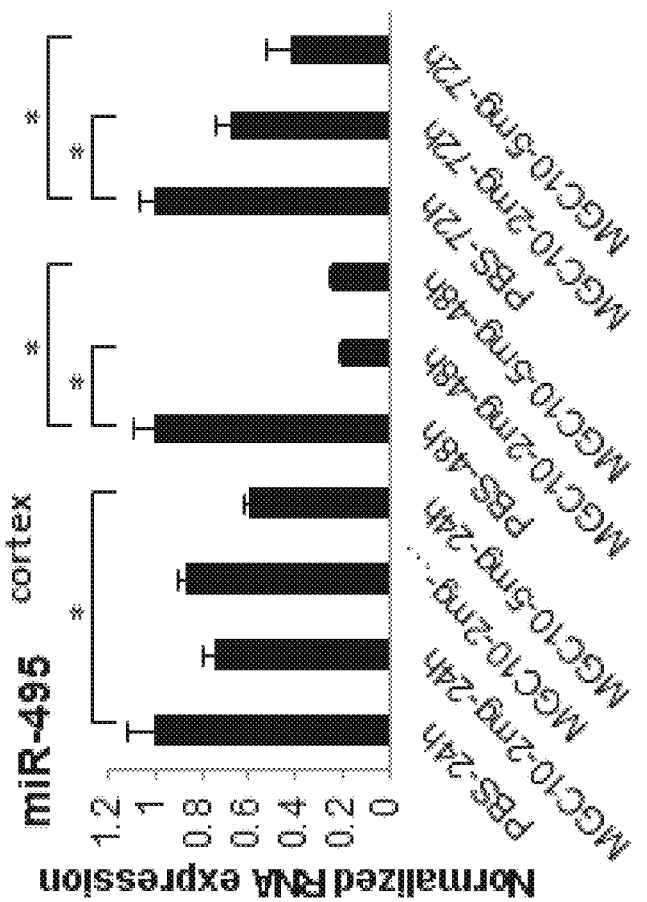
Figure 17E:
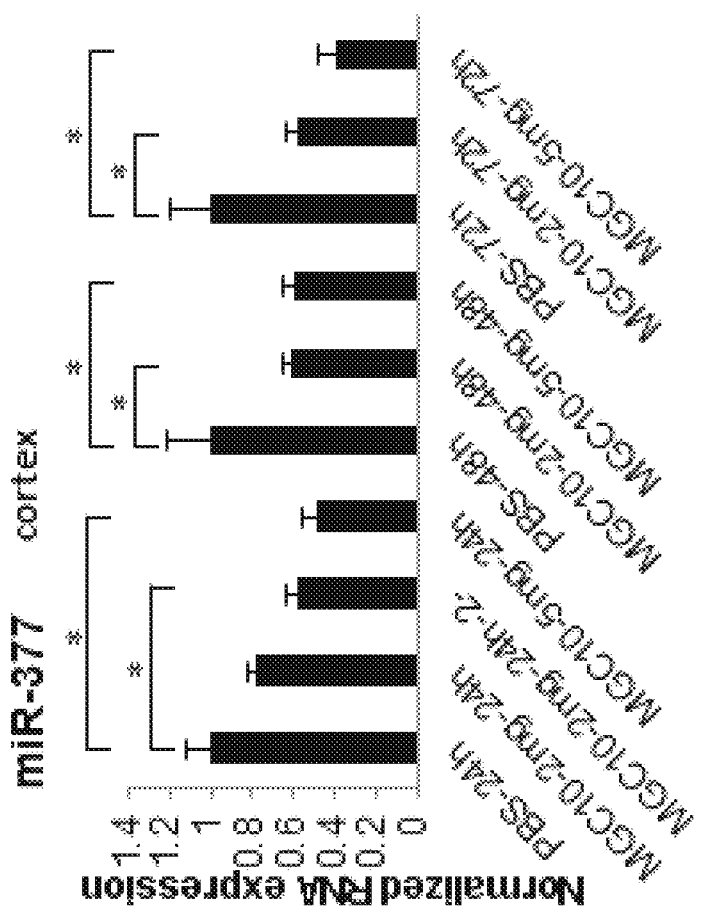
Figure 17F:
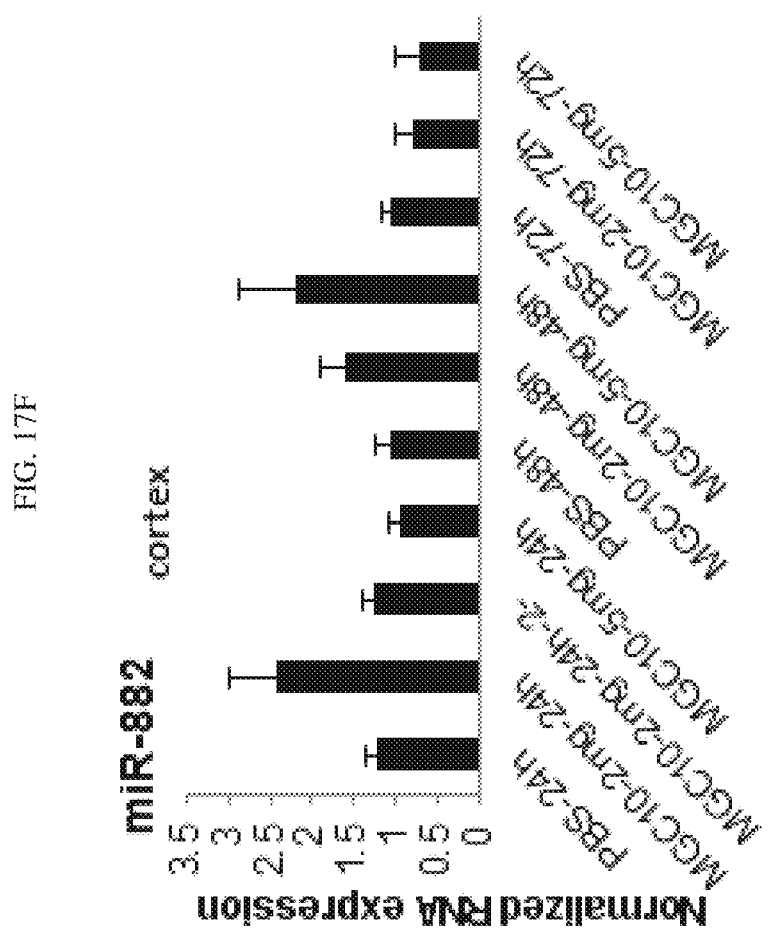

To knockdown the expression of lnc-MGC in vivo (mouse kidney), four LNA-modified Gapmers (MGC1, MGC5, MGC8 and MGC10) were designed (FIG. 16A). GapmeRs were synthesized and obtained from Exiqon (Vedbaek, Denmark) according to the following design strategy: MGC1, TCAaaaacataacGCC [SEQ ID NO:55]; MGC5, CACggtgctgaaaGAG [SEQ ID NO:56]; MGC8, TGAaggccacactAAC [SEQ ID NO:57]; MGC10, ATTtggcagtgggAAG [SEQ ID NO: 58], (uppercase: LNA; lowercase: DNA, full phosphorothioate). LNA modification has several advantages, including less toxicity, lower dosing and efficient targeting. Basic design of these Gapmers is three LNAs at both 5' and 3' ends of oligonucleotides and backbone is phosphorothioated (FIG. 16B). MMC were transfected with those Gapmers and the expression of lnc-MGC was examined. MGC10 consistently inhibited expression of lnc-MGC significantly at 48 hours after MGC10 transfection in two independent experiments although others did not with that consistency (FIGS. 16C-16D). MGC10 also reduced the expression of lnc-MGC even after TGF-β treatment (FIG. 16E). Some miRNAs in miR-379 cluster were confirmed to be reduced by MGC10 in MMC (FIGS. 16F-16H). Several targets (EDEME3, Tnrc6b and Phf21a) of miR-379 cluster were also upregulated by MGC10 (FIGS. 16I-16L), suggesting that down-regulation of miR-379 cluster restores the target expression.

Because MGC10 was effective to reduce the expression of miR-379 cluster in MMC in vitro, it was also tested in mouse kidney in vivo (FIGS. 17A-17F). Subcutaneous injection of 5 mg/kg MGC10 significantly reduced expression of lnc-MGC in the mouse kidney (24-72 hours) (FIG. 17B). miRNAs in the cluster (miR-379, miR-495, and miR-377) were also reduced in the same samples (FIGS. 17C-F). Those results suggest that MGC10 is effective in vivo in mouse kidney to reduce the expression of lnc-MGC and miR-379 cluster. To confirm the delivery of MGC10, the antisense in situ LNA modified probe was designed. Clear accumulation of MGC10 was observed in the kidney injected with MGC10 although very week background in the kidney injected with vehicle (PBS). Phosphorothioated oligonucleotides can be transported into nucleus by a protein complex (TCP1 complex). Because MGC10 is fully phosphorothioated, it may be efficiently transported into nucleus and cleaved lncMGC RNA and suppressed the expression of miR-379 cluster.

Next, MGC10 was tested in STZ injected diabetic mice. Five non-diabetic mice, five diabetic without injection, six diabetic mice with injection of negative control oligonucleotides and six diabetic mice with MGC10 injection were examined. lnc-MGC expression was higher in the kidney from diabetic mice than that from non-diabetic mice and interestingly, its expression was reduced in kidney from diabetic mice injected with MGC10, suggesting that MGC10 is effective even in diabetic mice. miRNAs in the miR-379 cluster behaved the similar patterns to lnc-MGC while no significant change of the expression of miR-882 (outside of miR-379 cluster) was observed. Targets (EDEM3, TRNC6B, CPEB4, Pumilio2) of miR-379 cluster were reduced in kidney from diabetic mice and it was restored in the kidney from diabetic mice injected with MGC10. Profibrotic genes, TGF-β1, Col1α2, Col4α1, CTGF, which were upregulated in the kidney from diabetic mice, were reduced in the kidney from diabetic mice injected with MGC10. These results show that MGC10 is effective to reduce the expression of lnc-MGC and miR-379 cluster miRNAs and restore targets and inhibits profibrotic genes even in diabetic mice.

Figure 18A:
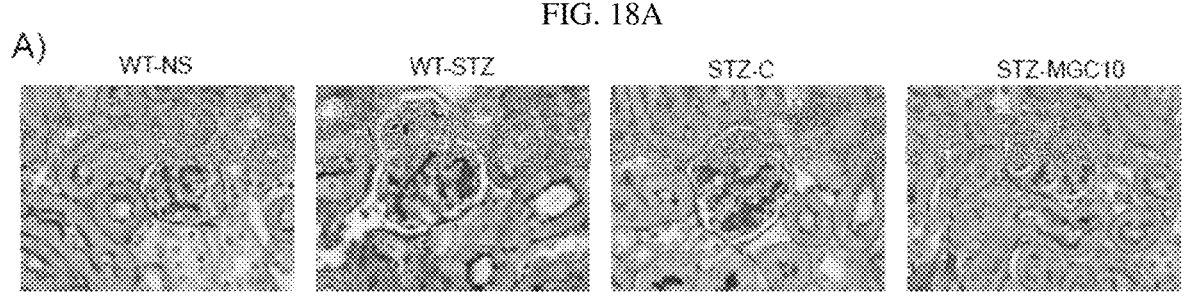
FIG. 18A shows PAS staining images of WT-NS, WT-STZ, STZ-C and STZ-MGC10. PAS staining showed mesangial expression and increased glomerular size in diabetic mice compared to that in non-diabetic mice and those were reduced in diabetic mice injected with MGC10.
Figure 18B:
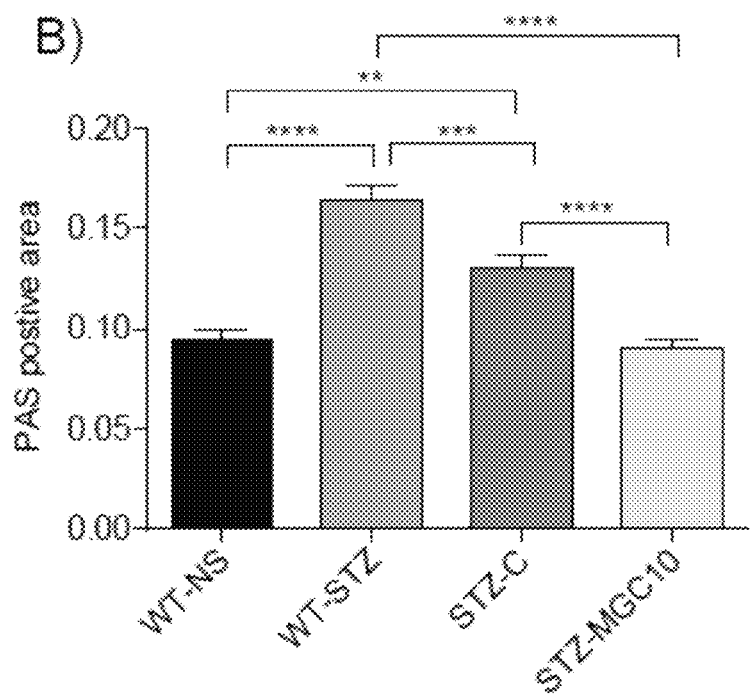
FIG. 18B is a bar graph of PAS positive area.
Figure 18C:
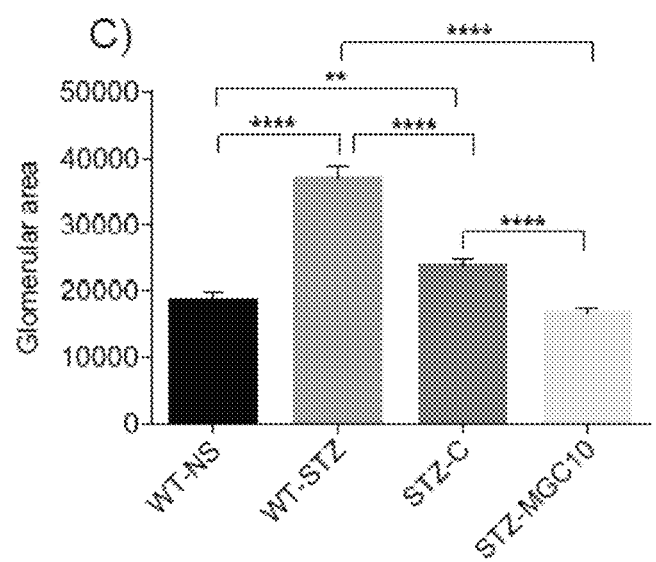
FIG. 18C is a bar graph of glomerular area.
Figure 18D:
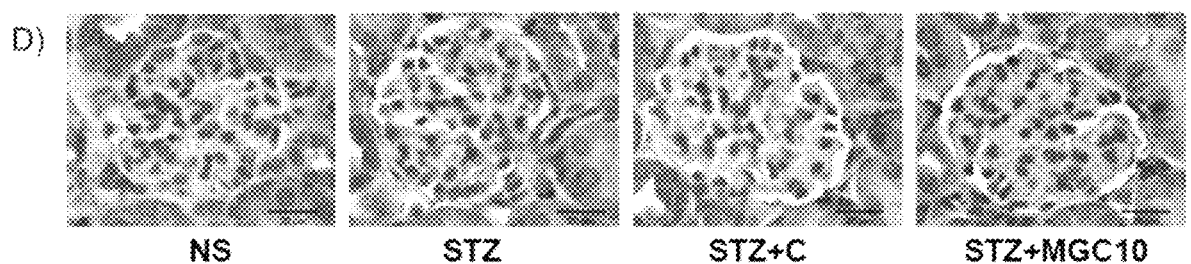
FIG. 18D is an image of NS, STZ, STZ+C and STZ+MGC10.
Figure 18E:
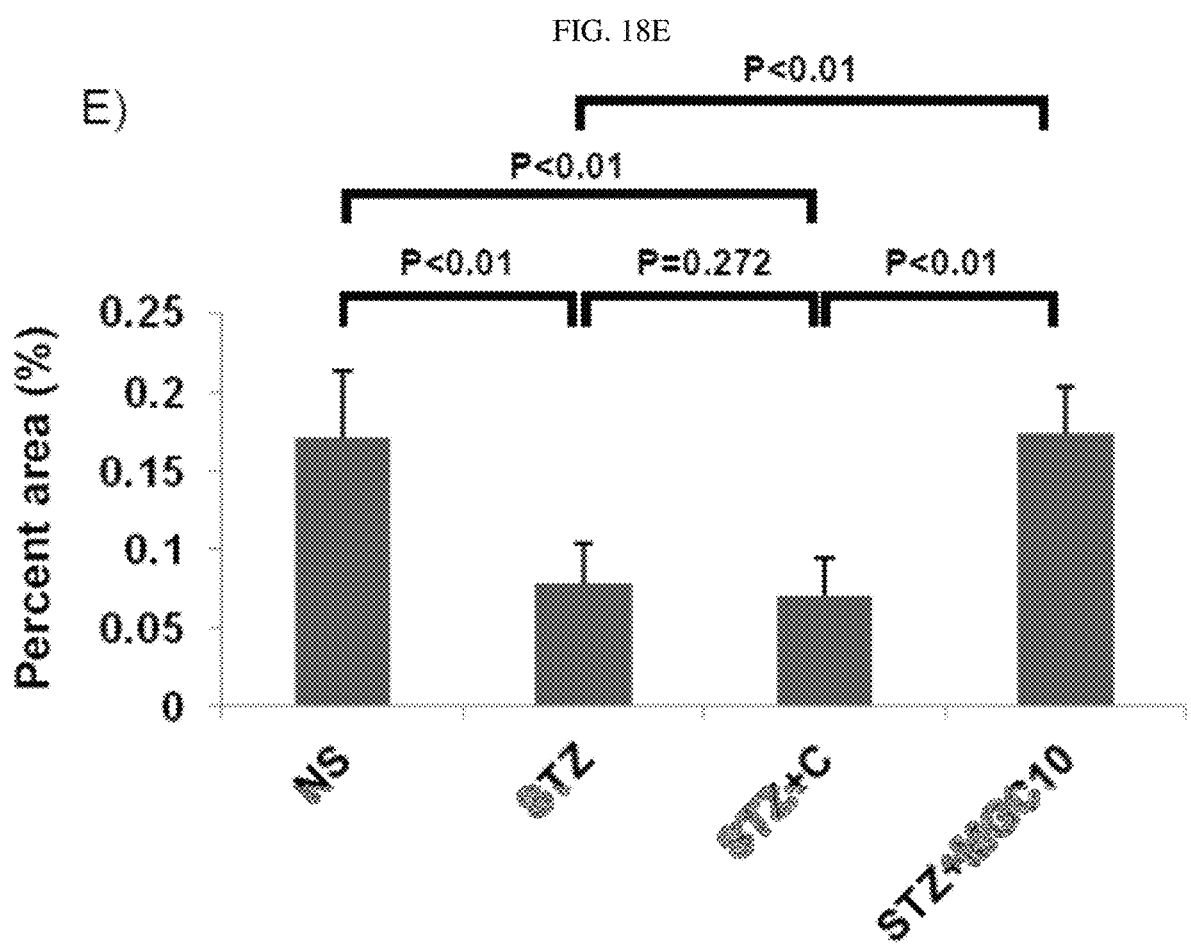
FIG. 18E is a bar graph of percent area. These results showed that MGC10 inhibits miR-379 and restore the EDEM3 and suppress the ER-stress in diabetic kidney.

PAS staining showed mesangial expansion and increased glomerular size in diabetic mice compared to that in non-diabetic mice and those were reduced in diabetic mice injected with MGC10 (FIGS. 18A-18C). Those results suggest that MGC10 can prevent glomerular fibrosis and hypertrophy in diabetic mice. Regarding to ER stress, IHC of EDEM3, a target of miR-379, showed the significant decrease in kidney glomeruli from diabetic mice and that was restored in that from diabetic mice injected with MGC10 (FIGS. 18D-18E). Those results demonstrate that MGC10 inhibits miR-379 and restore the EDEM3 and suppress the ER-stress in diabetic kidney. Serum profiling of those mice showed no significant difference in liver or kidney toxicity by MGC10 injection.

Example 6: Human Version of lncMGC and miRNA-379 Cluster and the Inhibition by Humanized Gapmer HMGC10

To test if miR-379 cluster is regulated by the same way even in human cells, human mesangial cells (HMC) was purchased from Lonza and treated with TGF-β or HG. Although genomic sequence of the miR-379 cluster region is conserved from human to mouse, because there are some minor mismatches in the genomic sequences, the expression of human version of lnc-MGC (hlnc-MGC) was examined in HMC by PCR using human specific primers. Similar to MMC, the expression of hlnc-MGC and miRNA-379 cluster miRNAs was increased by TGF-β or HG even in HMC although miR-882 (outside of miR-379 cluster) showed no significant difference. Decrease of some targets and increase of pro-fibrotic genes were confirmed in HMC.

Because target sequence in human of MGC10 has two base mismatches, human version of MGC10 (HMGC10) was designed based on human sequence. Basic chemistry was the same as mouse version of MGC10. The condition of transfection was optimized and D33 was the best (regarding viability and transfection efficiency). hlnc-MGC and miR-379 cluster miRNAs were reduced by transfection of HMGC10 in HMC, suggesting that the same strategy can be useful to suppressed cluster miRNAs in human cells and may be useful to treat DN patients.

Figure 19A:
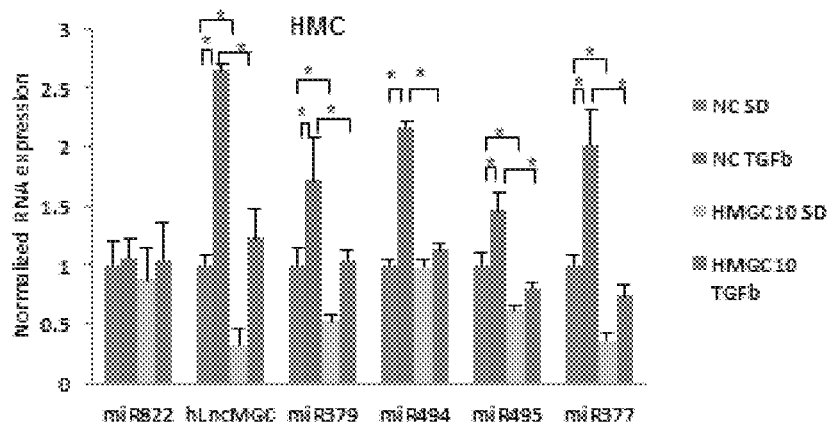
FIGS. 19A-19F are bar graphs of normalized RNA expression showing HMGC10 inhibiting the effects of HG or TGFβ.
Figure 19B:
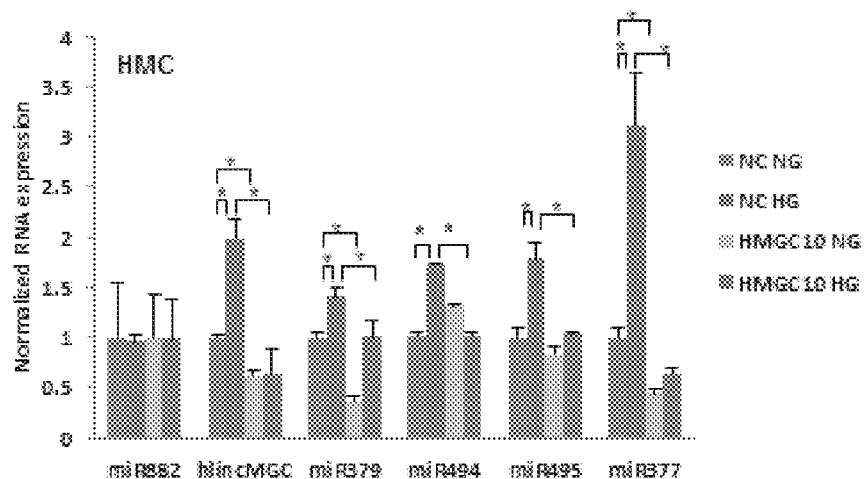
Figure 19C:
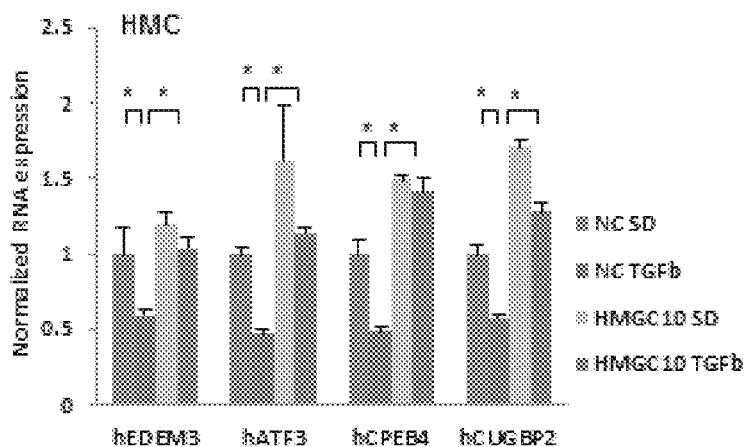
Figure 19D:
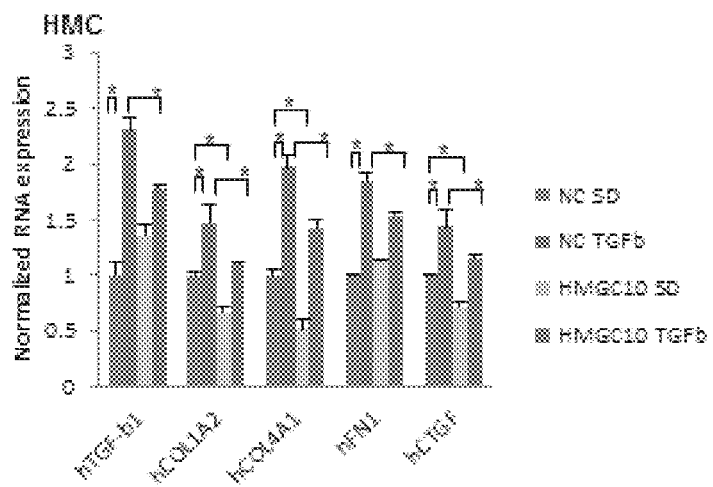
Figure 19E:
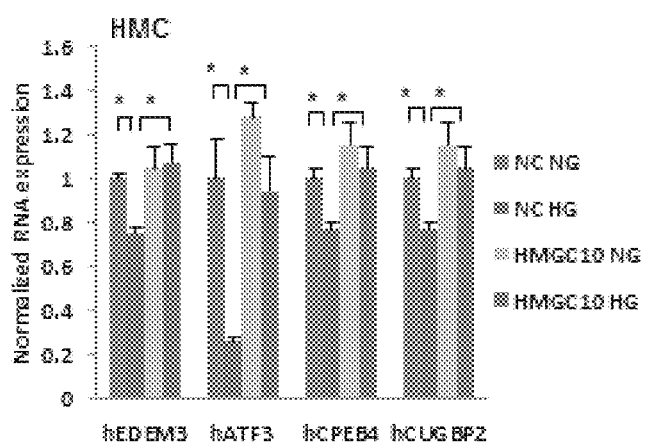
Figure 19F:
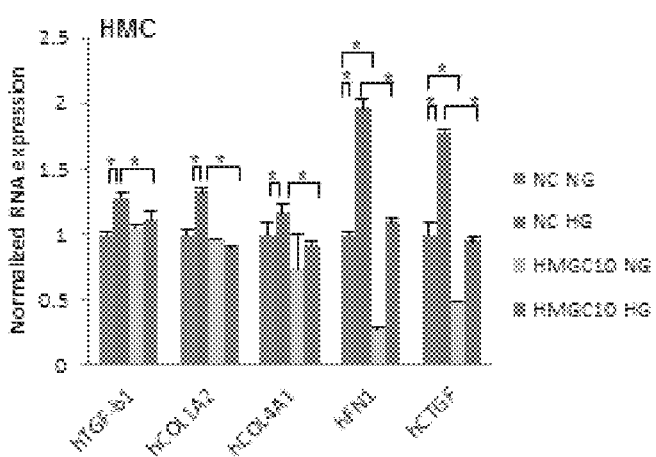

Next, whether HMGC10 can inhibit the effects by HG or TGF-β in HMC was tested. Human lncMGC expression was significantly inhibited by HMGC10 even after TGF-β treatment (FIG. 19A). Similar trends were observed in the expression of miR-379, miR-495 and miR-377 but not miR-822 which is out of miR-379 cluster, suggesting that inhibition of hlncMGC (host RNA) by HMGC10 resulted in reduction of the expression of miRNAs in the cluster in HMC treated with TGF-β (FIGS. 19A-19B). Targets (EDEM3, CPEB4, Pumilio2 and CUGBP2) of the cluster miRNAs were also examined and reduction of target expression was attenuated by HMGC10 treatment in HMC treated with TGF-β (FIGS. 19C and 19E). Induction of profibrotic genes (TGF-b1, COL1A2, COL4A1, FN1 and CTGF) by TGF-β was also attenuated by HMGC10 in HMC (FIGS. 19D and 19F). Those results suggest that reduction of hlncMGC by HMGC10 suppressed the expression of miR-379 cluster miRNAs and restored the expression of targets and also inhibited the expression of profibrotic genes in HMC even after treatment of TGF-β. Similar to TGF-β results, hlncMGC expression was significantly inhibited by HMGC10 in HMC treated with HG. The expression of miR-379, miR-495 and miR-377 but not miR-822 was inhibited by HMGC10 in HMC treated with HG. The reduction of target expression (EDEM3, CPEB4 and CUGBP2) was attenuated by HMGC10 treatment in HMC treated with HG. Induction of profibrotic genes (TGF-b1, COL1A2, COL4A1, FN1 and CTGF) by HG was also attenuated by HMGC10 in HMC. Again, those results suggest that reduction of hlncMGC by HMGC10 suppressed the expression of miR-379 cluster miRNAs and restored the expression of targets and also inhibited the expression of profibrotic genes in HMC even after treatment of HG. These results demonstrated that inhibition of lncMGC by Gapmer is useful also in human cells, which could be applied for human patient therapy.

Expression of miR-379 Cluster miRNAs in Human Kidney Tissue

Glomeruli of patients with diabetic kidney disease were studied for cluster miRNA expression. Several cluster miRNAs were examined by qRT-PCR and small RNA-sequencing in RNA isolated from micro-dissected glomeruli of kidney biopsies from 46 Southwestern American (Pima) Indians with documented type-2 diabetes. Total RNA was isolated using spin-columns; miRNA expression was quantified using qRT-PCR performed using TaqMan Array Human MicroRNA Card (Applied Biosystems) and small RNA-sequencing. Samples were normalized to geometric mean of reference RNAs. Expression of miRNA precursors was determined in micro-dissected glomeruli of nephrectomy samples using Affymetrix Human Gene 2.1 ST 24-Array. The cluster miRNAs were expressed robustly in these diabetic patient samples with read frequency comparable to miR-192, which are highly enriched in the kidney and mediate important mechanisms in diabetic nephropathy (DN).

In humans, DN is associated with glomerular hypertrophy, mesangial expansion and loss of podocytes leading to glomerulosclerosis. As described herein, increased expression of the precursors of some of the cluster miRNAs is associated with morphometric parameters of increased glomerular damage in micro-dissected glomeruli of human nephrectomy tissue samples that showed various stages of glomerular pathology similar to early stages diabetic glomerulopathy. These include decreased podocyte density and increased podocyte and glomerular volume as well as mesangial index, suggesting that cluster miRNA expression increases with glomerular damage. These associations suggest that inhibition of cluster miRNAs may also ameliorate human glomerular diseases including DN.

The experiments in this example show that diabetic conditions (HG) induces TGF-β1 which upregulates miR-379 cluster targeting ER stress regulators and protein synthesis that resulted in hypertrophy and ER stress in mouse kidney related to DN (FIG. 10). A host noncoding RNA (lnc-MGC) is regulated by CHOP which is activated by ER stress. The expression of miRNA-379 cluster depends on the expression of lnc-MGC from its promoter. CHOP siRNA inhibited the induction of lnc-MGC and miR-379 cluster miRNAs and the early features (ECM expression and cellular hypertrophy) of DN. miRNAs in this cluster target several groups of genes, transcription factors, RNA binding proteins regulating gene expression and protein synthesis and ER stress, which results in hypertrophy by increased protein synthesis and fibrosis by accumulation of ECM (profibrotic genes). Induction of those miRNAs was inhibited in the kidney from diabetic CHOPKO mice compared to those from WT mice. Similarly induction of those miRNAs and profibrotic genes by TGF-β was prevented in MMC from CHOPKO mice. A known ER stress inducer TM also induces lnc-MGC and miR-379 cluster miRNAs in MMC through reduction of N-glycosylation of EDEM3. Therefore, induction of lnc-MGC in diabetes may also be mediated by ER stress. Inhibition of those miRNAs by gapmer (MGC10) knocking down lnc-MGC ameliorated DN features (ECM accumulation and glomerular hypertrophy) in the early stage of mouse model of DN. This is the one of the critical mechanisms in DN and potential target to prevent DN. Gapmer inhibiting lnc-MGC (MGC10) can be developed as new drugs to prevent or treat the early stage of DN.

Figure 23A:
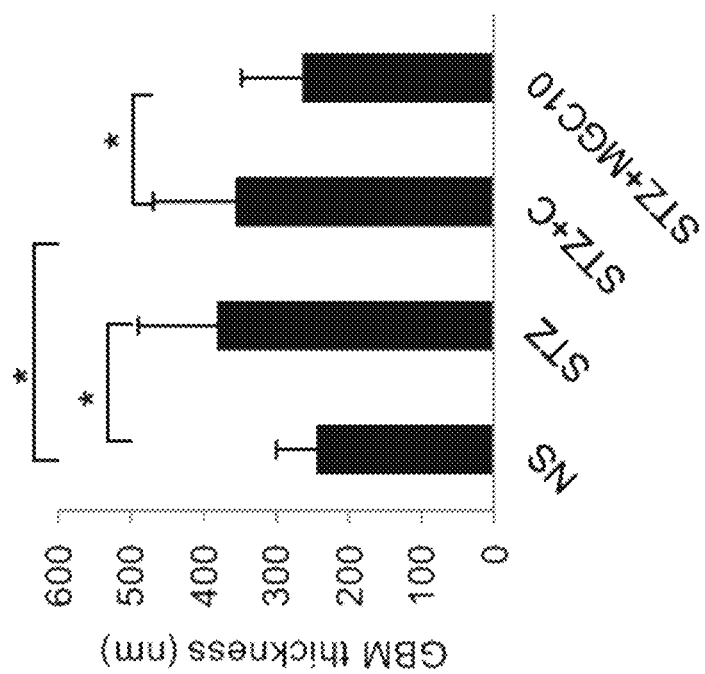
FIG. 23A depicts a bar graph of glomerular basement membrane (GBM) thickness, showing that the GMB thickness was significantly increased in diabetic mice (STZ and STZ-C) compared to non-diabetic mice (NS), and this was attenuated in diabetic mice injected with MGC10 (STZ-MGC10). *, P<0.05.
Figure 23B:
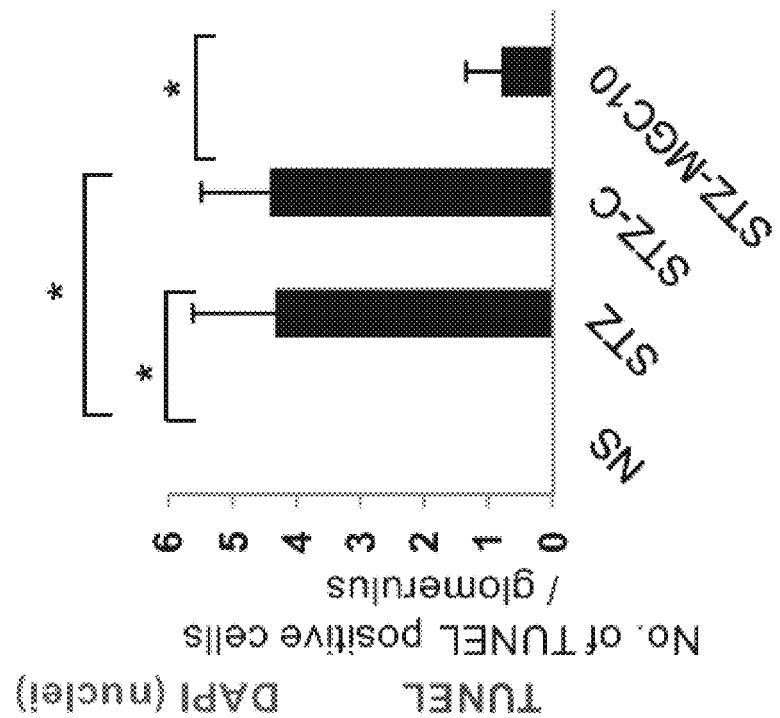
FIG. 23B depicts a bar graph of cell death measured by Terminal deoxynucleotidyl transferase (TdT) dUTP Nick-End Labeling (TUNEL) assay, showing that cell death was significantly increased (increase in TUNEL positive cells) in diabetic mice (STZ and STZ-C) compared to non-diabetic mice (NS), and this was attenuated in diabetic mice injected with MGC10 (STZ-MGC10). *, P<0.05.

TGF-β or diabetic conditions (as well as ER stress) induce glomerular podocyte dysfunction and death. In order to determine whether MGC10 confers any protection on podocytes in diabetes, podocyte effacement and glomerular basement membrane (GBM) thickness using electron microscopy was assessed (summarized in the bar graph depicted in FIG. 23A). Clear protection from diabetes induced podocyte effacement and GBM thickening was observed in diabetic mice treated with the MGC10 compared to control oligo. Cell death measured by Terminal deoxynucleotidyl transferase (TdT) dUTP Nick-End Labeling (TUNEL) assay was increased in glomeruli of diabetic mice compared to non-diabetic mice, which was attenuated by MGC10 (summarized in the bar graph depicted in FIG. 23B). These results indicate that MGC10 is effective in reducing the expression of not only lnc-MGC and miR-379 cluster miRNAs in vivo in diabetic mice, but also restores the expression of the cluster miRNA target genes, inhibits profibrotic genes, and prevents glomerular fibrosis, podocyte death, and hypertrophy in diabetic mice.

Example 7: Expression of Key miRNAs and lncRNA-MGC in CHOP KO Mice

Figure 8:
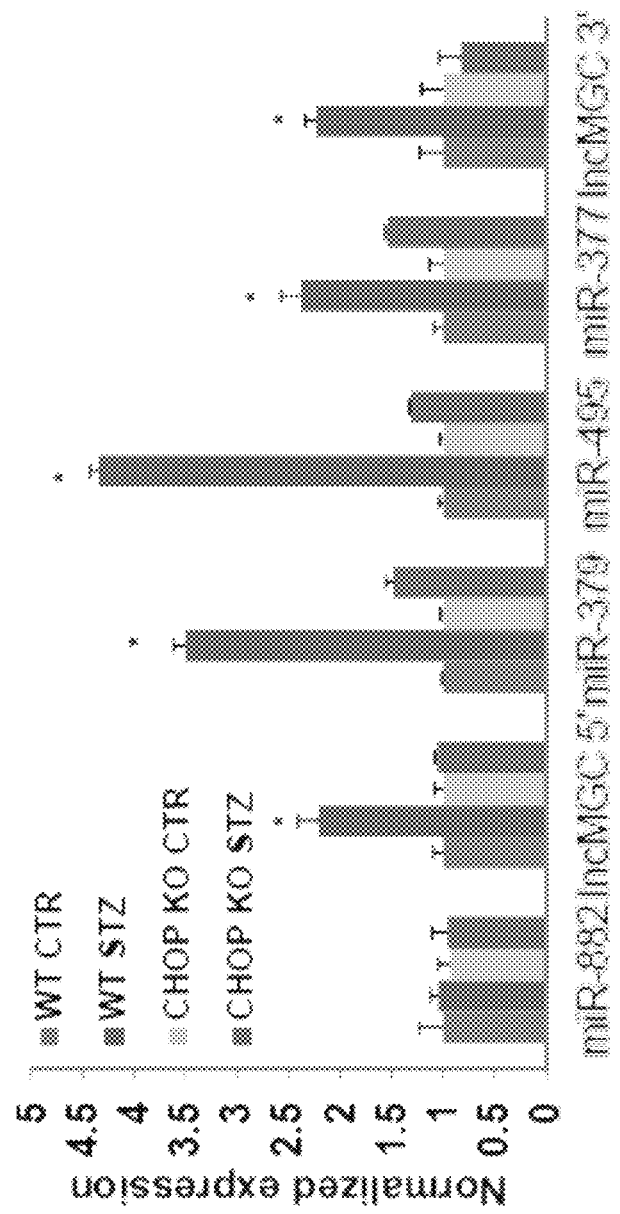
FIG. 8 is a bar graph depicting that diabetes induced increase in expression of key miRNAs and the lnc-MGC in mice glomeruli is ameliorated in CHOP knockout (KO) mice relative to wild type (WT).
Figure 9:
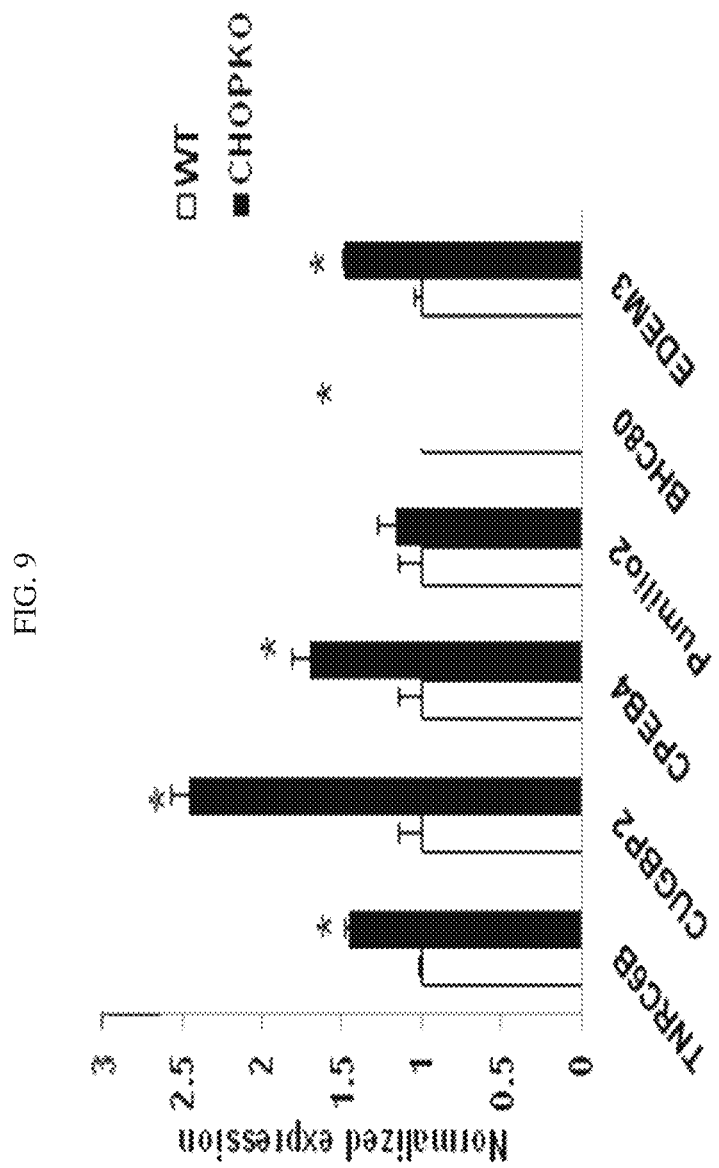
FIG. 9 is a bar graph depicting that expression levels of key miRNA target genes are higher in the glomeruli of CHOP KO mice versus WT mice.

Diabetes was induced in CHOP KO and control WT mice by administering STZ injections following standard protocols. CHOP KO mice developed diabetes at the same rates as WT mice. Four weeks after diabetes induction, mice were sacrificed. Diabetes-induced mice increased in the key cluster miRNAs, as well as in the lnc-MGC, which occurred in the glomeruli of WT mice, were abrogated in the glomeruli of diabetic CHOP KO mice (FIG. 8). The expression of profibrotic genes Col1αα2, Col4α1 and TGF-β1 were also attenuated in glomeruli from diabetic CHOP KO mice compared to diabetic WT mice. Histological analysis showed that PAS staining and glomerular hypertrophy were clearly reduced in diabetic CHOP KO mice compared to diabetic WT. Conversely, glomeruli of CHOP KO mice showed increased expression of key target genes of the cluster miRNAs compared to WT (FIG. 9).

MMCs were cultured from non-diabetic WT and CHOP KO mice, with or without TGF-β1. TGF-β1 induced increases in cellular hypertrophy were also ameliorated in MMCs from CHOP KO compared to WT mice. In addition, both the basal and TGF-β1 induced expression of fibrotic genes, Col1α1, Col4α1 and TGF-β1 (relevant to DN) were significantly decreased in MMC from the CHOP KO mice compared to WT. Under these conditions, both the basal and TGF-β1-induced increases in tree key cluster miRNAs and the lnc-RNA-MGC were also ameliorated in MMC derived from CHOP KO mice, compared to MMCs from WT mice.

Use of TALENs (Transcription Activator-Like Effector Nuclease) to Target the Cluster miRNAs TALENs designed and generated to target and delete two genomic regions in the miRNA cluster are used. The first is knockout of miR-379 and the upstream promoter, aimed to interrupt both miR-379 and lnc-MGC expression. The second is to delete the entire mega cluster region. These TALENs are tested in vitro for their readiness to inject directly into mouse embryos, for the rapid and efficient generation of KO mice.

Example: 8: Identify the Molecular Mechanisms by which Diabetic Conditions (HG and TGF-β1) Upregulate the miRNA Mega Cluster and its Host Transcript, lncRNA-MGC Diabetic Conditions Lead to Increased Transcription of the Promoter for the miRNA Cluster and Host Gene lncRNA-MGC The CHOP binding sites are cloned and nearby regions of the promoter into luciferase reporters. These constructs are transfected into MMC and treated with or without HG (25 mM), mannitol (19.5 mM) and incubated for 24-72 hours; TGF-β (10 ng/mL is added, and is incubated for 6-24 hours). MMCs pre-treated with or without CHOP specific siRNAs or negative control siRNAs, or MMC from WT versus CHOP KO mice is treated with HG, mannitol or TGF-β1 to determine if losing CHOP reduces promoter transactivation. Chromatin immunoprecipiation (ChIP) assays with a CHOP antibody are used to evaluate CHOP occupancy at the promoter regions in response to TGF-β1 and HG in MMCs. ChIP-qPCRs amplify the desired promoter genomic region and an unrelated control region. Western blots are used to determine CHOP protein levels.

Diabetic Conditions Increase the Expression of Multiple Mega Cluster Component Key miRNAs, and are Regulated by CHOP Wild type (WT) MMCs, MMC transfected with CHOP siRNA and MMCs from CHOP KO mice are treated with HG, mannitol and TGF-β1. RNA is extracted from the cells and the expression of lncRNA-MGC, and all 40 miRNAs within the cluster are systematically examined using primers designed for each of the mature miRNAs. This is supported by data indicating nearly 30 of the cluster miRNAs were induced in MMCs by TGF-β1 but inhibited by CHOP siRNAs.

Chromatin Features of this Genome Region

Known and novel transcripts, including miRNAs and many lncRNAs, can be identified by combining RNA-seq with ChIP-seq to identify domains marked with H3K4me3

(promoter mark), H3K36me3 (gene body), and enhancers (H3K4me1). Therefore, antibodies for these three chromatin marks are used to perform ChIP, and then use the ChIP-enriched DNA to sequence (ChIP-seq) this specific genomic region. The results verify whether the lncRNA and miRNAs within the cluster have their own promoters, or if they are transcribed as one unit. Initial observations indicate the presence of an H3K4me1 mark at the promoter start site, but nowhere else along the cluster, and lack of H3K4me3 marks, supporting the hypothesis, there is a single transcription unit. If the ChIP-seq data indicates potential intermediate promoters/transcription, it will be verified by cloning longer transcripts that include the majority of the miRNAs.

Influence of the Host lncRNA-MGC

MMCs are pre-treated with a mixture of siRNAs designed to target the lnc-MGC, and then treat them ±TGF-β1 or HG. Determining expression levels for all 40 miRNAs reveals if some or all are down regulated by the siRNAs.

Example 9: Determine the Functional Significance of MCs Up-Regulating Key Component miRNAs of the Mega Cluster and Down-Regulating their Key Targets in Response to HG and TGF-β

Validate Targets of miRNAs within the Mega Cluster that are Upregulated by TGF-β1 Predicted Computationally Putative target genes that are targeted by multiple miRNAs within the cluster and have functions related to DN include TNRC6B, CUGBP2, CPEB4, Pumilio2 (RNA binding proteins that regulate translation) and BHC80 (a transcription factor) and are common targets of multiple miRNAs including miR-379. Others, including HuR (RNA binding proteins), FoxP2, NF1A, Arid2 (TFs and co-factors) have binding sites in their 3' UTRs for 9 to 18 of the cluster miRNAs. EDEM3, a protein related to ER-associated degradation, is a miR-379 target with interesting functions. Decreasing EDEM3 through miR-379 will cause unfolded proteins to accumulate resulting in glomerular hypertrophy. Hence ER stress may induce further ER stress through the miR-379-EDEM3 pathway (FIG. 10).

3'UTRs of the genes listed above are cloned downstream of a luciferase reporter gene. MMCs are transfected with the constructs (sense and antisense), and negative control oligos, and treated with or without TGF-β1, or with mimics or inhibitors of key selected miRNAs that target the genes discussed above (including miR-379, -377 and -495). It is expected that miRNA mimics will decrease, and inhibitors will increase, the luciferase activity of reporters that contain 3'-UTRs from bona fide target genes. The miRNA binding sites in the 3' UTRs of targets identified experimentally are mutated to verify that the inhibitory effects of the mimics are lost. The protein and mRNA levels of these genes are also determined by Western blotting and RT-qPCR, respectively, as described.

In Silico Analysis of the Biological Functions of the Predicted Targets of the Mega Cluster miRNAs Select candidate megacluster miRNAs is selected, whose expression, according to miRNA-seq, is increased at least 1.5-2-fold under diabetic conditions, e.g., the 28-30 miRNAs identified in the studies. mRNA expression profiles induced by TGF-β1 in MMCs is compared (transcriptome profiling by RNA-seq) with the micro RNA profiles, to identify genes whose mRNA expression patterns inversely correlate with miRNA expression. The 3'-UTRs of these mRNAs (in the USCS and ENSEMBLE genome browsers) is aligned with the differentially expressed miRNAs to identify potential targets. The results are compared with publically available miRNA target prediction sites in TargetScan, miRBase, PicTar and DIANA-microT 3.0. Targets predicted by two or more databases and conserved among rat, human and mouse species are pooled. Particular attention is paid to those miRNA, whose predicted targets have functions related to MC dysfunction and DN. These targets are imported into GO, Pathway analyses software (IPA) and GSEA to determine their potential biological functions, and changes they cause in functional disease networks, which are supported by initial data showing that multiple miRNAs target the same genes related to MC dysfunction.

Ago-2-CLIP-Seq Based miRNA Target Profiling

The ClIP-seq (HITS-CLIP) method can generate sequencing data for both miRNAs and their complementary (target) mRNAs bound to Ago2 in RISCs (RNA-inducing silencing complex), genome-wide. Ago2-CLIP-Seq coupled with bioinformatics is used to identify specific megacluster miRNAs and their targets bound to Ago2 in control and TGF-β1-treated MMC. The results reveal mechanisms of action and the in vivo functional roles of the miRNA cluster. MMCs are treated with and without TGF-β1 for 24 hours, then UV crosslinked and immunoprecipitated with Ago2 antibody. Ago2 associated mRNAs and miRNAs are isolated, transcribed into cDNAs, and libraries prepared for small and regular RNAs for sequencing (Iluminia). From the smRNA-seq CLIP data, the abundance of each mouse miRNA (miRBase v20) in each sample is determined by processing the raw reads. For target mRNA-seq CLIP data, reads in each sample are first aligned to the mouse genome assembly (NCBI GRCm38) using TopHat2.

Ago2-binding clusters (containing reads that are significantly greater than background signal) are identified using the pooled, uniquely-aligned reads from all samples. Reads are summarized and normalized to obtain Ago2-binding cluster levels in each sample. Ago2 binding clusters across all the samples and replicates for each condition, and regions that differentially bind Ago2 between the two conditions are identified. The CLIP data and potential miRNA target sites predicted using base pair searches and existing tools like TargetScan are analyzed together to identify bona fide miRNA-mRNA interactions in control and TGF-β1-treated MCs.

In addition, the abundance of each Refseq mRNA is determined by regular RNA-seq of the MC samples without IP, summarized, normalized and compared between the two conditions using Bioconductor package "edgeR." The miRNA-mRNA interactions are integrated and identified by CLIP assays with the related changes in gene expression to further verify the interactions and reveal the potential effects of up-regulating cluster miRNAs on target gene expression levels. Furthermore, the potential functions of target mRNAs is determined with respect to DN using in silico analyses, including GO, IPA, network and motif analysis of the identified targets. Mega cluster miRNAs whose expression was co-modulated, or mega cluster target genes that contain multiple, closely related miRNA binding sites, are also identified by comparing data obtained under the two conditions. The expression levels of target mRNAs and corresponding proteins is assessed by qPCR and Western blots respectively.

Functional Roles of Candidate Megacluster miRNAs Tat Respond to TGF-β1/HG and their Targets in MC Dysfunction "Gain of function" and "loss of function" approaches are used. MMCs are transfected with oligonucleotide mimics, inhibitors of candidate miRNAs (miR-379, -495, -377), or NC oligos to determine whether manipulating the levels of their putative target genes can influence TGF-β1 and HG responses. At 48 to 72 hours post-transfection, the expression of miRNA target genes, fibrosis and hypertrophy related genes and proteins induced by TGF-β1/HG is determined by RT-qPCR and Western blotting. Cellular hypertrophy, oxidant and ER stress markers are assayed. Similarly, the gain and loss of function of key target genes (including EDEM3, CUGB2, Tnrc6, BHC80) are tested.

Role of CHOP and lncRNA-MGC on the Expression of miRNA Targets

The down-regulating of target genes, which augments DN pathogenesis is tested by determining that CHOP and lncRNA-MGC drive the expression of the miRNA cluster. The effect of CHOP siRNA and lncRNA-MGC siRNAs on the expression of the same miRNA targets, and potential new targets identified by CLIP-seq is determined in control and TGF-β1-treated MMCs. Targets are also examined in glomeruli and MMC derived from CHOP KO and WT mice.

Example 10: Functional Roles of the miRNA Cluster and lnc-MGC in DN Progression In Vivo Dysregulation of Key Megacluster miRNAs and their Targets in Mouse Models of DN miRNAs and their targets identified in MCs in vitro are regulated in mouse models of T1D- and T2D-associated DN in vivo using: 1) STZ-injected T1D mouse models of DN in which increases in expression f 30 of the cluster miRNAs was observed, 2) Male T2D leptin receptor deficient db/db mice (Strain BKS. CG-m+/+lepr db/J) at 10-14 weeks of age (101-103). db/db mice are obese, insulin resistant and diabetic by 6-8 weeks, and develop renal dysfunction by 10-12. After confirming hyperglycemia (glucose>300 mg/dL), db/db mice are compared with age-matched controls (db/+, glucose<150 mg/dL). 3) Akita T1D mice in the DBA2J background, which develop features of DN that are more overt than the STZ model. 4) Mice diet-induced obese (DIO) mice (C57BL/6J) on 14 week high fat diets (60 kcal percent fat), and controls on standard diets. DIO mice are insulin resistant, have mild hyperglycemia, elevated triglycerides and fibrosis/inflammation in glomeruli. Blood pressure, changes in physiology (blood glucose, urinary protein, albumin, creatinine), and the histology and morphology of the renal cortex are monitored regularly and at sacrifice. At the end of the indicated time periods, kidneys are dissected from all the mice, and cortical tissues and glomeruli isolated, then either flash frozen for RNA/protein extraction, or used to prepare MMCs. RT-QPCR is used to compare the basal levels of the miRNAs and their candidate target genes in glomeruli.

Reduced Levels of Mega Cluster miRNAs and lnc-MGC in CHOP-KO Mice; Protection (CHOP KO Mice) from DN Development CHOP KO mice and their controls are made diabetic by STZ injections. At 4, 12 and 16-20 weeks post-diabetes development, key features of DN are assessed in these mice. The expression levels of fibrotic genes, TGF-β1, 40 of the mega cluster miRNAs, and lnc-MGC, in glomeruli are determined at each time point. At least 10 mice per group are studied per time point and experiments are performed in triplicate.

Treating T1D Mice with LNA Anti-miR-379 Alters Course of DN, and LNA-Gapmers that Target the lnc-MGC LNA modification has several advantages, including less toxicity, lower dosing and efficient targeting. LNA-modified anti-miR-379 is designed, and the control LNAs target miR-239b, which is expressed in *Caenorhabditis elegans*.

To target lnc-MGC in vivo Gapmer technology is adopted/used. LNA™ longRNA GapmeRs are newly available antisense oligos that are used to functionally analyze mRNAs and lncRNAs. They contain a central stretch (gap) of DNA monomers flanked by blocking of LNA-modified nucleotides (http://www.exiqon.com/gamper). The LNA blocks increase the oligos' target affinity and nuclease resistance and the DNA gap induces RNase H cleavage of the target RNA after binding. The gapmers are 14-16 nucleotides in length and are fully phosphorothioated. Exiqon's advanced design algorithms design the most potent LNA™ longRNA GapmeRs that have minimal off-target effects and high success rates. LNA-anti-miR-379 or LNA-anti-lnc-MGC are injected subcutaneously twice weekly into control and STZ-injected DBA2J mice, which develop more sever DN than C57BL6 mice. The progression of key structural, histological and molecular features of DN is followed for up to 20 weeks as described. The anti-miR-379 and anti-lnc-MGC are evaluated in these in vivo translational studies.

Example 11: Genetic Knockout of the Megacluster miRNA379

To study the function of miR-379 in vivo, miR-379 knockout (KO) mouse was generated. The genome editing using the RNA-guided Cas9 nucleases from the microbial CRISPR (clustered regularly interspaced short palindromic repeat)-Cas systems was used to generate gene knockout mouse. A paired nickase strategy was used for engineering a system to ameliorate off-target activity. Paired nicking method can reduce off-target activity by 50- to 1,500-fold in cell lines and to facilitate gene knockout in mouse zygotes without sacrificing on-target cleavage efficiency.

Figure 11A:
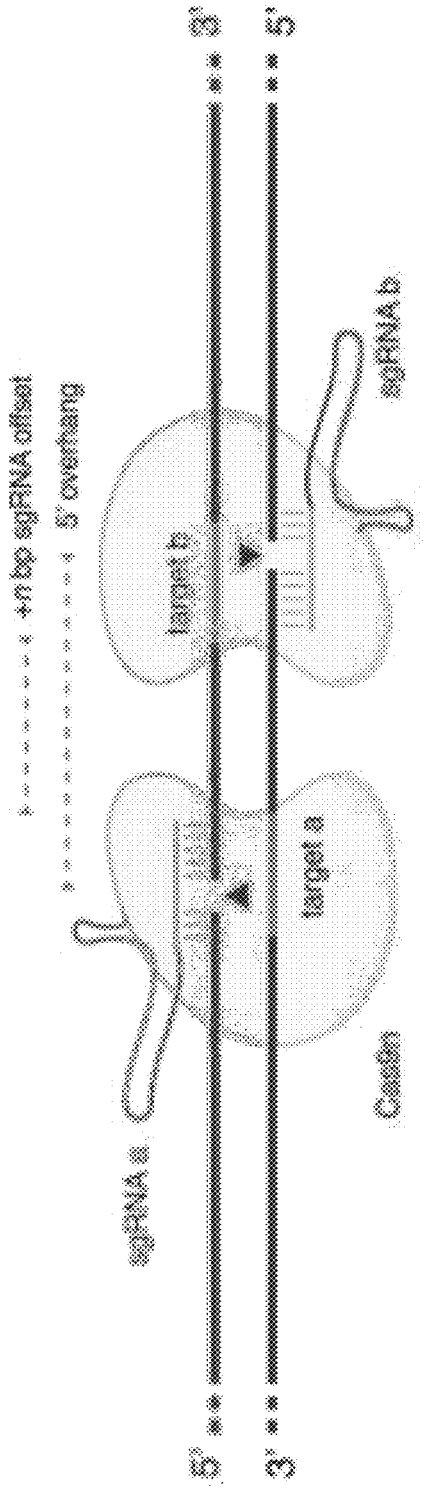
FIG. 11A is a schematic of genome editing using the RNA-guided Cas9 nucleases from the microbial CRISPR (clustered regularly interspaced short palindromic repeat)-Cas systems for generating miR-379 knock-out mouse.
Figure 11B:
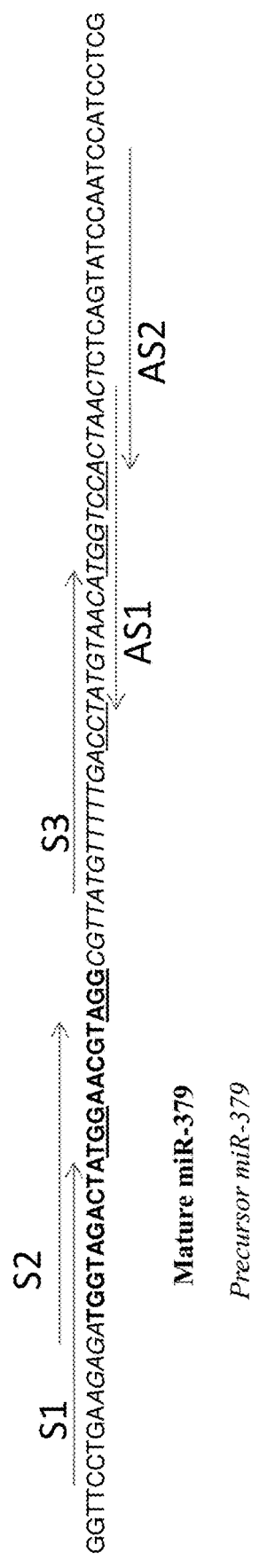
FIG. 11B depicts the miR-379 genomic region (SEQ ID NO: 45) complementary regions of five guide RNAs. S1, S2, and S3 are sense guide RNAs; and AS1 and AS2 are antisense guide RNAs.
Figure 13A:
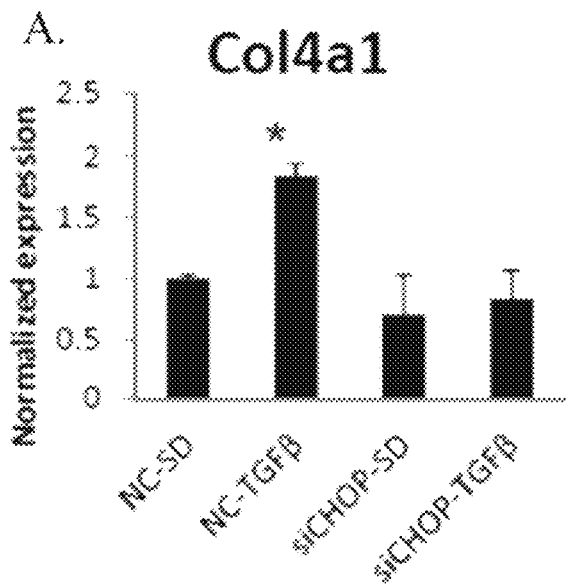
FIGS. 13A-13D are graphs of normalized mRNA expression of the putative target genes under different treatment conditions.
Figure 13B:
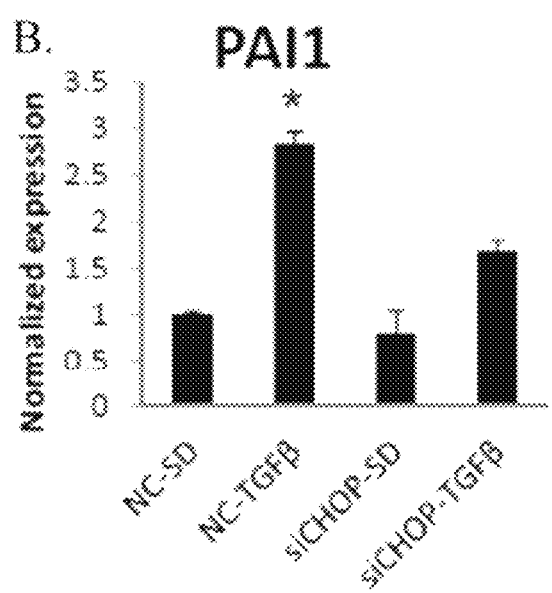
Figure 13C:
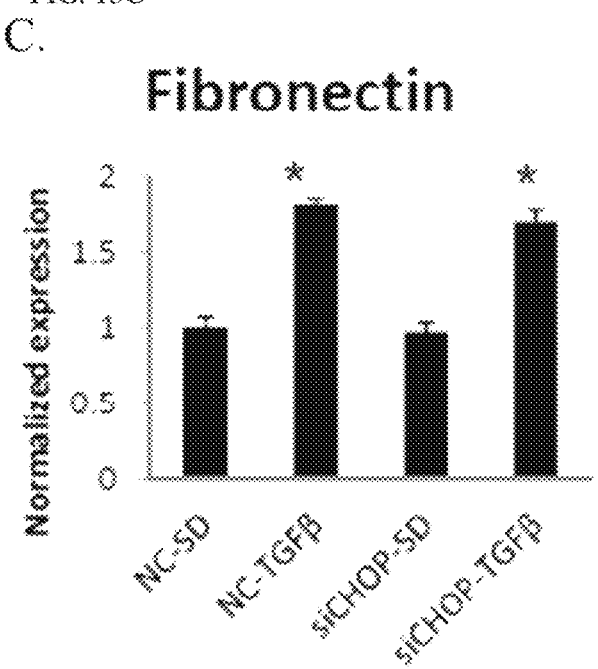
Figure 13D:
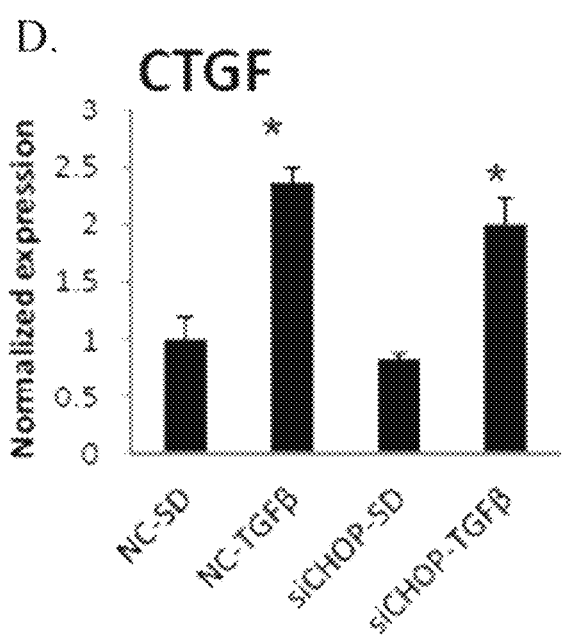
Figure 14A:
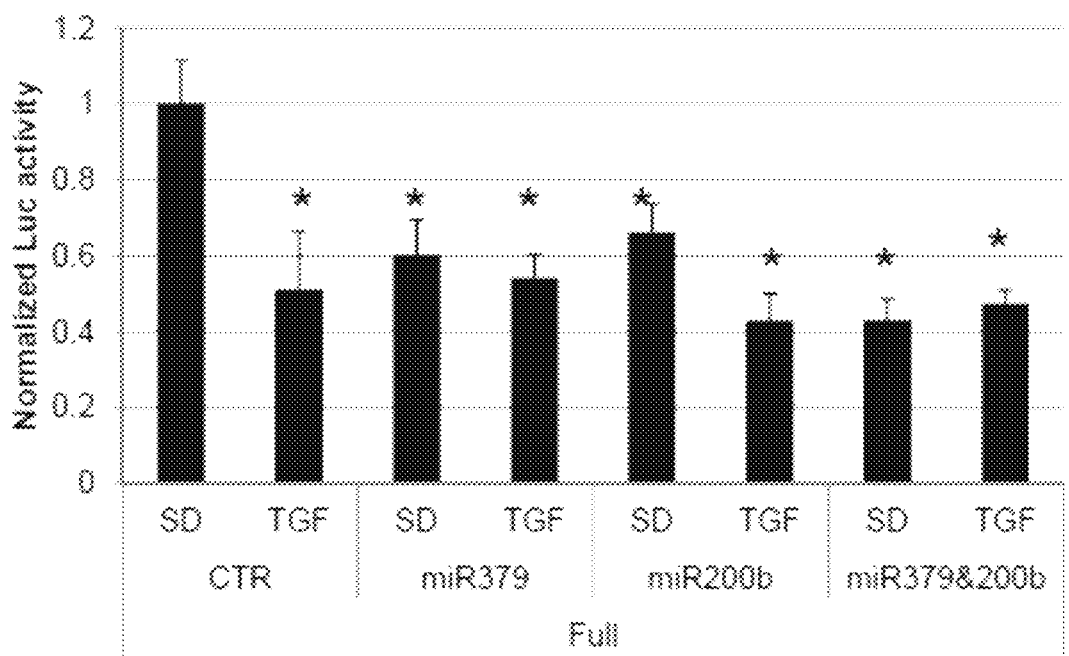
FIGS. 14A-14B are bar graphs of normalized Luciferase (Luc) activity of the EDEM3 expression vectors after cotransfection to MMC with miR-379 mimic. The data suggests that miR200 family and miR-379 cluster may collaborate to inhibit EDEM3 expression. The data also suggests that miR-379 cluster and miR-200b upregulated in diabetic conditions induces DN through hypertrophy and fibrosis mediated by EDEM3 (ER stress).
Figure 14B:
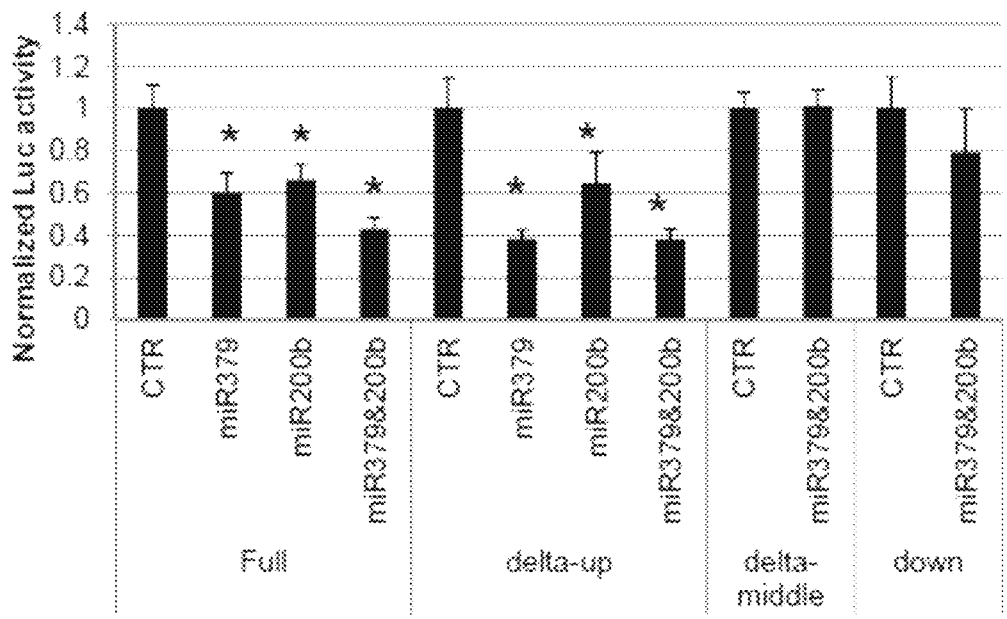

A double nickase strategy was used to delete mouse miR-379 genomic region with less off-target. Five guide RNAs, three sense (S1, S2, and S3) and two antisense (AS1 and AS2) were designed (shown in FIG. 11B). Positions and actual sequences of oligonucleotides to construct expression vectors (e.g., PX461, EGFP; PX462, or Puromycine (PX461 and PX462 are plasmid names; the double strand DNA made from designed and synthesized sense and antisense oligos were cloned into the plasmid vectors. The guide RNAs are expressed from the plasmids. PX461 has EGFP gene to monitor the transfection by GFP. PX462 has Puromycine resistance gene to select the cells by drug (Puromycine) resistance) are listed below.

Potential Targets

S1

(SEQ ID NO: 27)

CCTGAAGAGATGGTAGACTATGG

S1S (SEQ ID NO: 28)

CACCgCCTGAAGAGATGGTAGACTA

S1AS (SEQ ID NO: 29)

AAACTAGTCTACCATCTCTTCAGGc

S2

(SEQ ID NO: 30)

GATGGTAGACTATGGAACGTAGG

S2S (SEQ ID NO: 31)

CACCgGATGGTAGACTATGGAACGT

```
S2AS
                                             (SEQ ID NO: 32)
AAACACGTTCCATAGTCTACCATCc

S3
                                             (SEQ ID NO: 33)
TGTTTTTGACCTATGTAACATGG

S3S
                                             (SEQ ID NO: 34)
CACCgTGTTTTTGACCTATGTAACA

S3AS
                                             (SEQ ID NO: 35)
AAACTGTTACATAGGTCAAAAACAc

AS1
                                             (SEQ ID NO: 36)
CCTATGTAACATGGTCCACTAAC

AS1S
                                             (SEQ ID NO: 37)
CACCgGTTAGTGGACCATGTTACAT

AS1AS
                                             (SEQ ID NO: 38)
AAACATGTAACATGGTCCACTAACc

AS2
                                             (SEQ ID NO: 39)
CCACTAACTCTCAGTATCCAATC

AS2S
                                             (SEQ ID NO: 40)
CACCgGATTGGATACTGAGAGTTAG

AS2AS
                                             (SEQ ID NO: 41)
AAACCTAACTCTCAGTATCCAATCc
```

In the above sequences, S1 is one of the target sequences. S1s is synthesized oligonucleotides for sense strand with extra 5'overhang (CACC) for cloning. S1AS is synthesized oligonucleotides for antisense strand with extra 5'overhang (AAAC) for cloning. S1S and S1AS are complimentary and annealed double strand DNA (S1S/S1AS) has 5'overhang for cloning. Small "g" is transcription start site in the expression vector. Likewise, in the remaining target sequences listed above.

Using TCMK cells (mouse kidney cell line) in vitro, activity of genome editing at miR-370 locus was tested with several combinations of those guide RNAs (sense and antisense). Since the combination S2 and AS1 showed the best activity, this combination was injected into fertilized eggs to make mutant mice.

Two strategies are used to inject guide RNAs. First, guide RNAs are injected into pronuclei of fertilized eggs with plasmids expressing guide RNAs and nickase. Second, the guide RNA is transcribed in vitro and nickase RNA is injected into cytoplasm of fertilized eggs. The first strategy required injecting the same plasmids used for cell line transfection in vitro. For the second strategy, T7-transcribed guide RNAs were made. For this purpose, guide RNA part in the plasmids was amplified with primers with T7-promoter and reverse primer for guide RNA (below).

```
T7-S2
                                             (SEQ ID NO: 42)
TTAATACGACTCACTATAGGGATGGTAGACTATGGAACGT

T7-AS1
                                             (SEQ ID NO: 43)
TTAATACGACTCACTATAGGGTTAGTGGACCATGTTACAT gRNA-R
                                             (SEQ ID NO: 44)
AAAAGCACCGACTCGGTGCC
```

The amplified PCR products were used as template for in vitro transcription of guide RNAs using T7 in vitro transcription kit. Seven mice were obtained from plasmid injection and fourteen mice were obtained from RNA injection experiments. The short deletion of miR-379 genomic region was tested by fragment analysis in the PCR fragment amplified from tail DNA.

Deletion found in 8F was 36 bp at miR-379 locus. FIG. 20A-B shows the 36 base-pair deletion in the miR-379 locus of a mouse generated using the CRISPR/CAS9 system described in this disclosure.

Figure 21A:
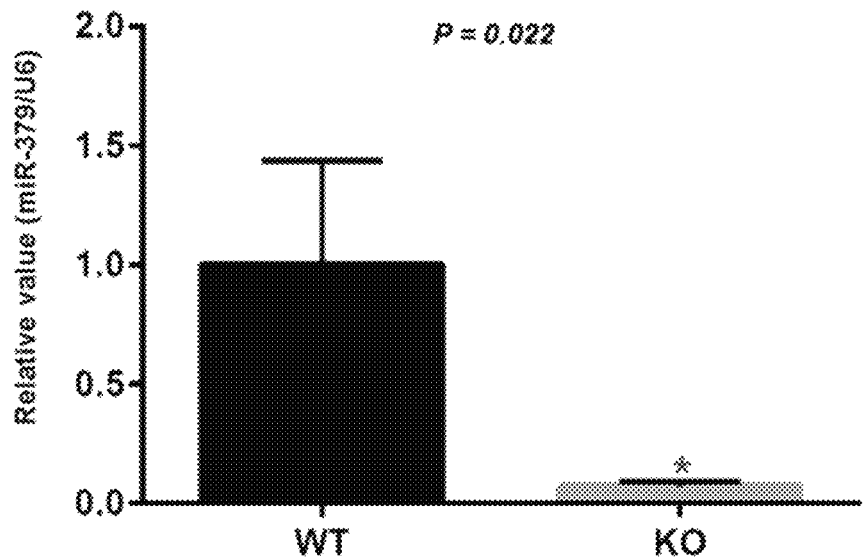
FIGS. 21A-21B are bar graphs depicting expression levels of miR-379 (FIG. 21A) and EDEM3 (FIG. 21B) from miR-379 knockout (miR-379KO) mice.
Figure 21B:
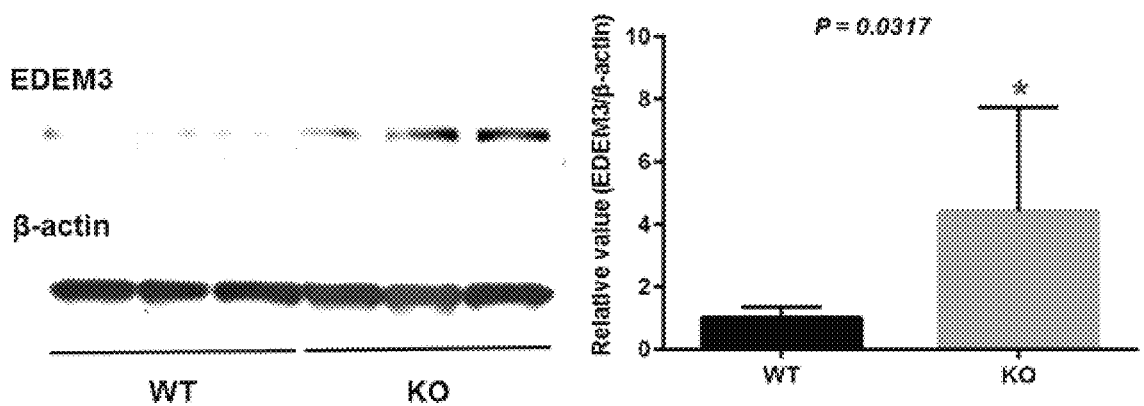

A colony of mice possessing the 8F deletion was generated by crossing heterozygotes to produce homozygotes. The colony was expanded and mice were used for characterization of miR-379 knockout as well as for experiments of type 1 diabetes (STZ-induced) and high fat diet (HFD). Kidney mesangial cells (MC) from three miR-379 KO mice were cultured in vitro and expression of miR-379 was significantly reduced compared to MC from wild type mice (FIG. 21A). One of the targets of miR-379 was confirmed significantly increased in miR-370K0 mice compared to MC from wild type mice (FIG. 21B). These mice were also used for in vitro experiments in diabetic conditions (high glucose, TGF-β, and other treatments.

Example 12: Replacement of miR-379 Region with Poly(A) Signal (to Terminate Transcription)

Figure 22:
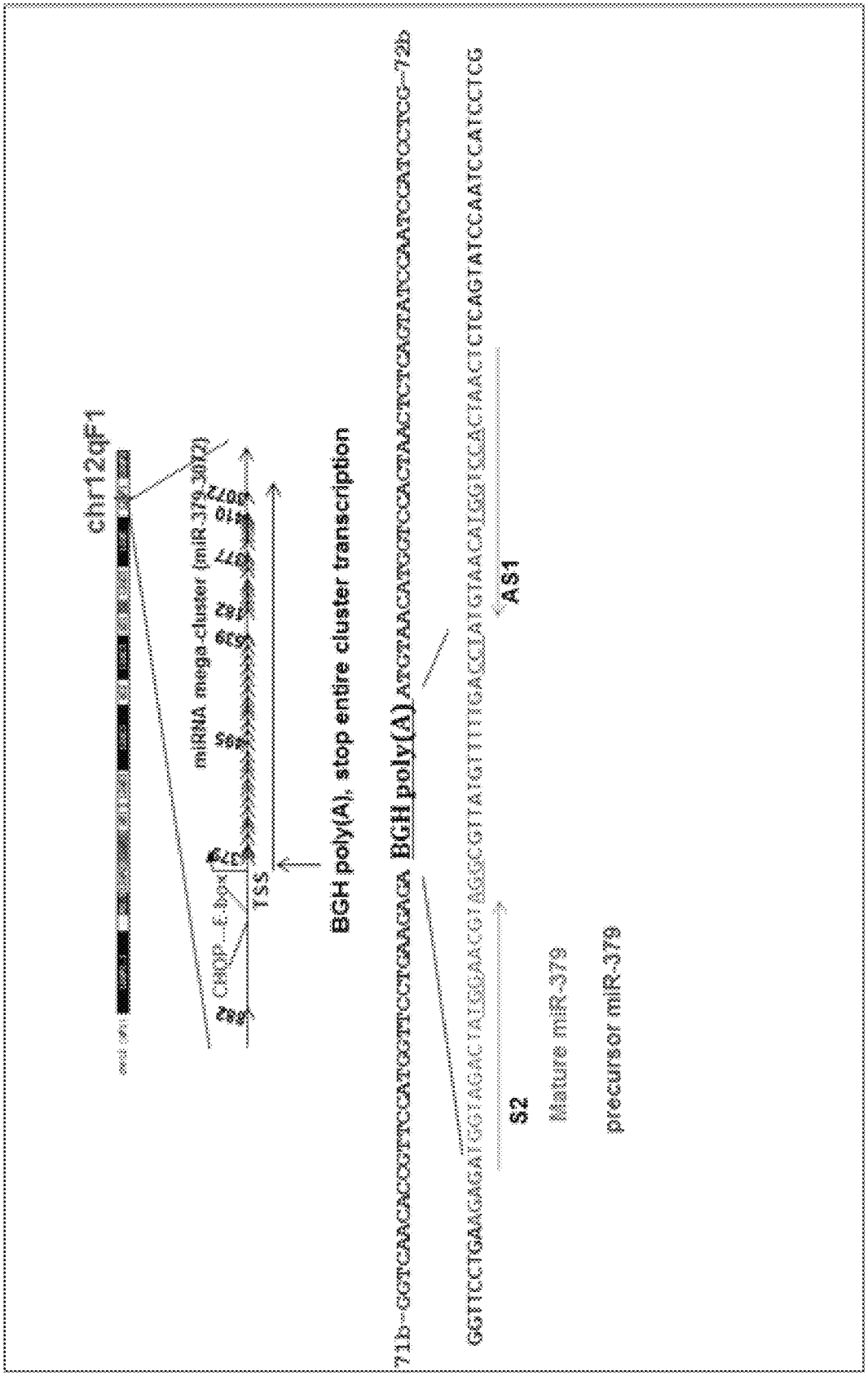
FIG. 22 depicts a schematic of the strategy for replacing a human miR-379 region with a poly(A) signal to terminate transcription of the human miR-379. Sequence legend: SEQ ID NO: 117.

Another method to stop the transcription of lnc-MGC (miR-379 cluster) was also established, as depicted in FIG. 22. For replacement of miR-379 region with poly(A) signal sequence, ~200 bases oligonucleotide was designed (below) which includes 5' and 3' homologous sequences to miR-379 region (underline) and minimum BGH poly(A) sequence in the middle (italics). DNA ligase inhibitor (SCR7) was also used to enhance recombination.
Minimum bGH polyA (52 Bases)

```
                                             [SEQ ID NO: 72]
GTCCTTTCCTAATAAAATGAGGAAATTGCATCGCATTGTCTGAGTAGGT
GTC
```

Any available poly(A) sites from any of the mammalian transcripts can be used as well.
Synthesized oligonucleotide (single stranded DNA) for targeting

```
                                             [SEQ ID NO: 73]
AAGTGACGCCAGCTTCAGGGACAAGGCCCAAGTTTCTAGGGGTCAACACC

GTTCCATGGTTCCTGAAGAGAGTCCTTTTCCTAATAAAATGAGGAAATTG

CATCGCATTGTCTGAGTAGGTGTCGACATGTAACATGGTCCACTAACT

CTCAGTATCCAATCCATCCTCGGAGGGCACCCCGGAGGTGTTACCAACA

GC
```

For the replacement, ~100 eggs were injected with Cas9 nickase mRNA, two guide RNAs (S2 & AS1) and SCR7 (ligase inhibitor inhibiting end joining and enhancing replacement). Twenty two (22) mice were born and twenty-one (21) mice survived. By PCR screening, five founders were identified as four full insertion (7F, 9M, 10M, 18M)

and one partial insertion (8F). These mice were crossed with wild-type B6 mice and confirmed replacement. The line with partial insertion was designated as S1536 and full insertion was S1543. These lines were expanded for further experiment. The method to insert poly(A) signal are applicable to stop any kinds of transcripts (coding or noncoding) if guide RNAs are designed for specific targets.

Example 13: Strategy for Treating Human Patients

Because the disclosed CRSPR-CAS system works to delete (inhibit) miR-397 cluster in mouse tissue, miR-379 cluster in human patients is inhibited by the same strategy. Therefore, human versions of guide RNAs for miR-379 region were designed (below). Six guide RNAs (4 sense (S) and 2 antisense (AS)) were designed. Positions and actual sequences of oligonucleotides for guide RNAs on human miR379 [SEQ ID NO: 79] are shown below:

>human miR379

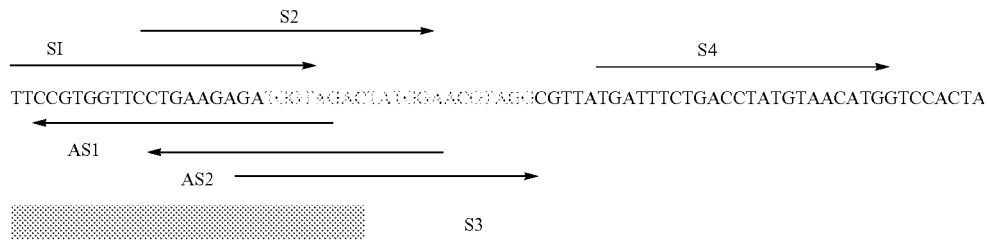

Design of Human miR379 Guide RNAs

Sequences of potential targets (e.g., S1 below) and sequences of oligos for cloning (e.g., S1S and S1AS) are listed below (the oligos for cloning are listed below the target sequences):

```
S1:
                                    [SEQ ID NO: 80]
TTCCGTGGTTCCTGAAGAGATGG

S1S:
                                    [SEQ ID NO: 120]
CACCgTTCCGTGGTTCCTGAAGAGA

S1AS:
                                    [SEQ ID NO: 121]
AAACTCTTCAGGAACCACGGAAc

S2:
                                    [SEQ ID NO: 27]
CCTGAAGAGATGGTAGACTATGG (same as mouse S1)

S2S:
                                    [SEQ ID NO: 28]
CACCgCCTGAAGAGATGGTAGACTA

S2AS:
                                    [SEQ ID NO: 29]
AAACTAGTCTACCATCTCTTCAGGc

S3:
                                    [SEQ ID NO: 30]
GATGGTAGACTATGGAACGTAGG (same as mouse S2)

S3S:
                                    [SEQ ID NO: 31]
CACCgGATGGTAGACTATGGAACGT

S3AS:
                                    [SEQ ID NO: 32]
AAACACGTTCCATAGTCTACCATCc

S4:
                                    [SEQ ID NO: 82]
GATTTCTGACCTATGTAACATGG

S4S:
                                    [SEQ ID NO: 122]
CACCgGATTTCTGACCTATGTAACA

S4AS:
                                    [SEQ ID NO: 123]
AAACTGTTACATAGGTCAGAAATCc

AS1:
                                    [SEQ ID NO: 81]
CCGTGGTTCCTGAAGAGATGGTA

AS1S:
                                    [SEQ ID NO: 124]
CACCgTACCATCTCTTCAGGAACCA

AS1AS:
                                    [SEQ ID NO: 125]
AAACTGGTTCCTGAAGAGATGGTAc

AS2:
                                    [SEQ ID NO: 27]
CCTGAAGAGATGGTAGACTATGG (same target as S2)

AS2S:
                                    [SEQ ID NO: 126]
CACCgCCATAGTCTACCATCTCTTC

AS2AS:
                                    [SEQ ID NO: 127]
AAACGAAGAGATGGTAGACTATGGc
```

S1, S2, S3, S4, AS1, and AS2 are sequences of potential targets. Sequences of oligos for cloning are under the each target sequences. For example, S1S is sequence of sense oligo for S1 and S1AS is sequence of antisense oligo for S1. They are designed for constructing expression vectors for miR-379 target genes (e.g., PX461, EGFP; PX462, or Puromycine (PX461 and PX462 are plasmid names; the double strand DNA made from designed and synthesized sense and antisense oligos were cloned into the plasmid vectors. The guide RNAs are expressed from the plasmids. PX461 has EGFP gene to monitor the transfection by GFP. PX462 has Puromycine resistance gene to select the cells by drug (Puromycine) resistance). Possible combinations include: S1-AS2, S2-AS1, S3-AS1, S3-AS2, and S4-AS2. Additional sets of possible combinations include S1S-S1AS, S4S-S4AS, AS1S-AS1AS, AS2S-AS2AS. Delivery of plasmids expressing these guide RNAs and CAS9 nickase (or other CAS9 derivatives, for example, fusion with repressor) into human kidney reduces human lnc-MGC and miRNA-379 cluster and prevents DN.

OTHER EMBODIMENTS

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure within known or customary practice within the art to which the disclosure pertains and may be applied to the essential features hereinbefore set forth, and follows in the scope of the appended claims.

What is claimed is:

1. An isolated compound comprising a nucleic acid sequence, wherein:
   (a) said nucleic acid sequence (i) is perfectly complementary to at least 15 continuous nucleobases from nucleobases 11 to 27, or 115 to 139 of SEQ ID NO: 25, 118, 26 or 119, or (ii) is selected from SEQ ID NOs: 10-21;
   (b) said nucleic acid sequence comprises at least one nucleobase analog or at least one modified internucleotide linkage; and
   (c) said nucleic acid is 15 to 20 nucleobases in length.

2. The compound of claim 1, wherein said nucleobase analog is at the 5'-end or the 3'-end of said nucleic acid sequence.

3. The compound of claim 2, wherein said nucleic acid sequence comprises three nucleobase analogs at the 5'-end or the 3'-end of said nucleic acid sequence.

4. The compound of claim 3, wherein said nucleobase analogs are independently selected from the group consisting of a Locked Nucleic Acid (LNA), a 2'-O-alkyl nucleobase, a 2'-Fluoro nucleobase, and a 2'-OMe nucleobase.

5. The compound of claim 1, wherein said nucleic acid sequence is perfectly complementary to at least 16 continuous nucleobases from nucleobases 11 to 27, or 115 to 139 of SEQ ID NO: 25, 118, 26 or 119.

6. The compound of claim 1, wherein said modified internucleotide linkage is a phosphorothioate linkage.

7. The compound of claim 1, wherein said nucleic acid sequence is selected from SEQ ID NO: 10, 11, 12, 13, 14, 15, 16, 17, 18, 19, 20, and 21.

8. The compound of claim 1, wherein said nucleic acid sequence is perfectly complementary to at least 15 continuous nucleobases from nucleobases 11 to 27, or 115 to 139 of SEQ ID NO: 25, 118, 26 or 119.

9. The compound of claim 1, wherein said nucleic acid sequence is perfectly complementary to a sequence that is at least 90% identical to the entire length of at least 18 continuous nucleobases from nucleobases 11 to 27, or 115 to 139 of SEQ ID NO: 25, 118, 26 or 119.

* * * * *

UNITED STATES PATENT AND TRADEMARK OFFICE
CERTIFICATE OF CORRECTION

PATENT NO. : 10,787,664 B2
APPLICATION NO. : 15/163816
DATED : September 29, 2020
INVENTOR(S) : Rama Natarajan and Mitsuo Kato It is certified that error appears in the above-identified patent and that said Letters Patent is hereby corrected as shown below:

In the Specification

Delete the text in Column 1, Lines 17-21, under the heading "STATEMENT AS TO RIGHTS TO INVENTIONS MADE UNDER FEDERALLY SPONSORED RESEARCH AND DEVELOPMENT," and insert the following:
--This invention was made with government support under R01 DK081705 awarded by the National Institutes of Health. The government has certain rights in the invention.--

Signed and Sealed this
Twenty-eighth Day of May, 2024

Katherine Kelly Vidal
*Director of the United States Patent and Trademark Office*